US007718171B2

(12) United States Patent
Flambard

(10) Patent No.: US 7,718,171 B2
(45) **Date of Patent: *May 18, 2010**

(54) **REDUCING HEART RATE IN MAMMALS USING MILK DERIVED FERMENTATION PRODUCTS PRODUCED USING *LACTOBACILLUS HELVETICUS***

(75) Inventor: Bénédicte Flambard, Frederiksberg (DK)

(73) Assignee: Chr. Hansen A/S, Horsholm (DK)

( * ) Notice: Subject to any disclaimer, the term of this patent is extended or adjusted under 35 U.S.C. 154(b) by 1300 days.

This patent is subject to a terminal disclaimer.

(21) Appl. No.: 10/819,275

(22) Filed: Apr. 7, 2004

(65) Prior Publication Data

US 2005/0031602 A1 Feb. 10, 2005

Related U.S. Application Data

(60) Provisional application No. 60/460,880, filed on Apr. 8, 2003.

(30) Foreign Application Priority Data

Apr. 7, 2003 (EP) ................................ 03076018

(51) Int. Cl.
*A61K 35/00* (2006.01)

(52) U.S. Cl. .......................... 424/115; 435/41; 424/439

(58) Field of Classification Search .................. 424/115
See application file for complete search history.

(56) References Cited

U.S. PATENT DOCUMENTS

| | | | | |
|---|---|---|---|---|
| 4,607,023 | A | 8/1986 | Thibault et al. | |
| 5,695,796 | A | 12/1997 | Yamamoto et al. | |
| 6,054,151 | A | 4/2000 | Kwon et al. | |
| 6,498,177 | B2 | 12/2002 | Jeon et al. | |
| 6,596,301 | B1 * | 7/2003 | Masuyama et al. | 424/439 |
| 6,746,671 | B2 | 6/2004 | Steidler et al. | |
| 7,029,670 | B2 | 4/2006 | Yamamoto et al. | |
| 2002/0182301 | A1 | 12/2002 | Draaisma et al. | |
| 2004/0106171 | A1 | 6/2004 | Flambard | |
| 2005/0142166 | A1 | 6/2005 | Flambard | |

FOREIGN PATENT DOCUMENTS

| | | | |
|---|---|---|---|
| EP | 0 058 074 | | 8/1982 |
| EP | 0 583 074 | | 2/1994 |
| EP | 0 737 690 | | 10/1996 |
| EP | 0 821 968 | A2 | 2/1998 |
| EP | 0 966 969 | A1 | 12/1999 |
| EP | 1 016 709 | A1 | 7/2000 |
| EP | 1 142 481 | | 10/2001 |
| JP | 08-099994 | | 4/1996 |
| WO | WO 01/32836 | A1 | 5/2001 |
| WO | WO 01/32905 | | 5/2001 |
| WO | WO 01/85984 | A1 | 11/2001 |
| WO | WO 03/082019 | A2 | 10/2003 |

OTHER PUBLICATIONS

St. -Onge et al "Consumption of fermented and nonfermented dairy products:effects on cholesterol concetration and metabolism", Am. J. Clinical Nutrition, vol. 71, 2000, p. /674-81.*

Takano, Antonie van Leewenhoek vol. 82, p. 333-340, 2002 "Anti-hypertensive activity of fermented dairy products containing biogenic peptides".*

Seppo et al "A fermented milk high in bioactive peptides has a blodd pressure-lowering effect in hypertensive subjects" Am. J. of CLinical Nutrition, vol. 77, 2003.*

Siezen, R.J., "Multi-domain, cell-envelope proteinases of lactic acid bacteria" (1999) Antonie van Leeuwenhoek, vol. 76, p. 139-155.*

Fuglsang et al., "*Cardiovascular Effects of Fermented Milk Containing Angiotensin-Converting Enzyme Inhibitors Evaluated in Permanently Catheterized, Spontaneously Hypertensive Rats*," Applied and Environmental Microbiology, Jul. 2002, p. 3566-3569, American Society for Microbiology.

Hata et al., "*A placebo-controlled study of the effect of sour milk on blood pressure in hypertensive subjects*," Am. J. Clin. Nutr., 1996:64:767-71, American Society for Clinical Nutrition, USA.

Pederson et al., "*Genetic Characterization of a Cell Envelope-Associated Proteinase from Lactobacillus helveticus CNRZ32*," Journal of Bacteriology, Aug. 1999, vol. 181, No. 15, pp. 4592-4597, American Society for Microbiology.

Feinberg et al., "*A Technique for Radiolabeling DNA Restriction Endonuclease Fragments to High Specific Activity*," Analytical Biochemistry, 132, 6-13 (1983), Academic Press, Inc.

Needleman et al., *A General Method Applicable to the Search for Similarities in the Amino Acid Sequence of Two Proteins*, J. Mol. Biol. (1970) 48, 443-453.

Altschul et al., "*Gapped BLAST and PSI-BLAST: a new generation of protein database search programs*," Nucleic Acids Research, 1997, vol. 25, No. 17, 3389-3402, Oxford University Press.

Zaza et al., "*Heart rate reduction: optimism with some caveats*," [online] [retrieved on Jun. 15, 2004]. Retrieved from the Internet <URL: http://ftp.escardio.org/newscast/stock2001/sipido.htm>.

EPO Search Report dated Oct. 1, 2003 for Application No. EP 03076018.5, Filed Apr. 7, 2003.

Yamamoto, et al., "Molecular cloning and sequence analysis of a gene encoding an extracellular proteinase from *Lactobacillus helvecticus* CP790," Biosci. Biotechnol. Biochem. 64(6):1217-1222 (2000).

Ferreira, et al., "Isolation of bradykinin-potentiating peptides from *Bothrops jararaca* venom," Biochemistry, 9(13):2583-2593 (1970).

Fitzgerald, et al., "Milk protein-derived peptide inhibitors of angiotensin-I-converting enzyme," British Journal of Nutrition 84:S33-S37 (Suppl. I 2000).

(Continued)

*Primary Examiner*—Jon P Weber
*Assistant Examiner*—Tiffany M Gough
(74) *Attorney, Agent, or Firm*—Hunton & Williams LLP

(57) ABSTRACT

Use of a composition obtainable by a process comprising fermenting a food material, comprising animal milk or vegetable proteins, with a lactic acid bacterium to obtain a fermented food material which comprises active components with heart rate reducing properties for the manufacture of a product for reducing the heart rate and/or the fluctuations in the heart rate of a mammalian.

19 Claims, 2 Drawing Sheets

OTHER PUBLICATIONS

Figure 1:
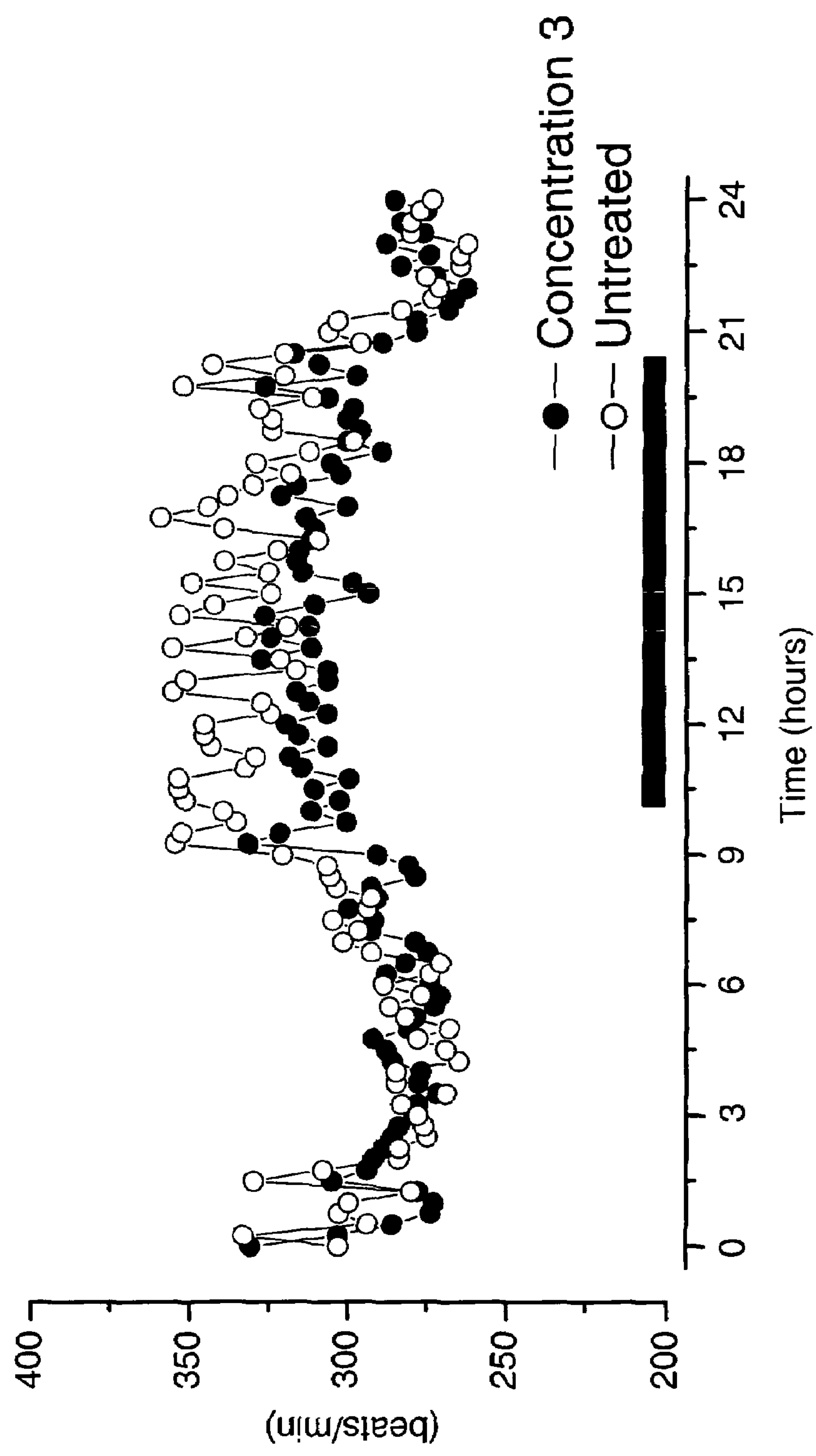

Gobbetti, et al., "Production of angiotensin-I-converting-enzyme-inhibitory peptides in fermented milks started by *Lactobacillus delbreuckii* subsp. *bulgaricus* SS1 and *Lactococcus lactis* subsp. *cremoris* FT4," Applied and Environmental Microbiology 66(9):3898-3904 (2000).

Nakamura, et al., "Antihypertensive effect of sour milk and peptides isolated from it that are inhibitors to angiotensin-I-converting enzyme," J. Dairy Sci. 78:1253-1257 (1995).

Yamamoto, et al., "Antihypertensive effect of the peptides derived from casein by an extracellular proteinase from *Lactobacillus helveticus* CP790," J. Dairy Sci. 77:917-922 (1994).

Meisel, et al., "Bioactive peptides encrypted in milk proteins: proteolytic activation and thropho-functional properties," Antonie van Leeuwenhoek 76:207-215 (1999).

Law, et al., "Review Article: Proteolytic enzymes of lactic acid bacteria," Int. Dairy Journal 7(1):1-11 (1997).

Yin, et al., "Effect of lactic acid bacterial fermentation on the characteristics of minced mackerel," Journal of Food Science 67(2):786-792 (2002).

Flambard, "Role of bacterial cell wall proteinase in antihypertension," Sciences Des Aliments 22:209-222 (2002).

International Search Report mailed Sep. 11, 2003 for International Application No. PCT/DK03/00212.

Lowery, et al., "Protein measurement with the folin phenol reagent," J. Biol. Chem. 193:265-275 (1951).

Shin, et al., "His-His-Leu, an angiotensin I converting enzyme inhibitory peptide derived from Korean soybean paste, exerts antihypertensive activity in vivo," J. Agric. Food Chem. 49:3004-3009 (2001).

International Search Report dated Dec. 30, 2002 for International Application No. PCT/DK03/00522.

Maeno, et al., "Identification of an antihypertensive peptide from casein hydrolysate produced by a proteinase from *Lactobacillus helveticus* CP790," J. Dairy Sci. 79:1316-1321 (1996).

Yamamoto, et al., "Purification and characterization of an antihypertensive peptide from a yogurt-like product fermented by *Lactobacillus helveticus* CPN4," J. Dairy Sci. 82(7):1388-1393 (1999).

Pridmore, et al., GenEmbl Database Accession No. CQ759881 (Mar. 3, 2004) alignment with SEQ ID No. 1.

Danish Search Report dated Mar. 20, 2003 for Danish Patent Application No. PA 2002 01195.

Deutsche Sammlung von Mikroorganismen und Zellkulturen GmbH, Search results for lactic acid bacteria, German collection of microorganisms and cell cultures, at http://www.dsmz.de/dsmzhome.htm (Jul. 12, 2004).

National Center for Biotechnology Information, "What does NCBI do?," at http://www.ncbi.nlm.nih.gov (Jul. 12, 2004).

Aimutis, "Challenges in developing effective probiotic functional foods, including scientific and regulatory considerations," Dairy Nutrition for a Healthy Future: Bulletin of the IDF 363, pp. 30-38.

Magboul, et al., "Purification and characterization of an x-prolyl-dipeptidyl aminopeptidase from *Lactobacillus curvatus* DPC2024," Lait 80(4):385-396 (2000).

Altschul, et al., "Basic Local Alignment Search Tool" J. Mol. Biol. 215:403-410 (1990).

McGinnis, et al., "BLAST: at the core of a powerful and diverse set of sequence analysis tools," Nucleic Acids Research 32:W20-W25 (Web Server issue 2004).

Teo, et al., "Clinical Investigation and Reports: Long-term effects of cholesterol lowering and angiotensin-converting enzyme inhibition on coronary atherosclerosis," Circulation 102:1748-1754 (2000).

Marmur, "A procedure for the isolation of deoxyribonucleic acid from micro-organisms," J. Mol. Biol. 3:208-218 (1961).

International Search Report dated Aug. 31, 2004 for International Application No. PCT/DK2004/000239, filed Apr. 5, 2004.

* cited by examiner

REDUCING HEART RATE IN MAMMALS USING MILK DERIVED FERMENTATION PRODUCTS PRODUCED USING *LACTOBACILLUS HELVETICUS*

CROSS-REFERENCE TO RELATED APPLICATION

This application claims the benefit of U.S. Provisional Application No. 60/460,880, filed Apr. 8, 2003, and European Patent Application No. EP 03076018.5, filed Apr. 7, 2003, the disclosures of each of which are herein incorporated by reference in their entireties.

FIELD OF INVENTION

The present invention relates to the use of a composition obtainable by a process comprising fermenting a food material, comprising animal milk or vegetable proteins, with a lactic acid bacterium to obtain a fermented food material which comprises peptides or other active components with heart rate reducing properties for the manufacture of a product for reducing the heart rate in a mammalian.

TECHNICAL BACKGROUND AND PRIOR ART

Several studies clearly support the notion that a lower resting heart rate is linked to improved survival. In the general population, several studies have shown a strong positive correlation between higher resting heart rate and increased mortality. A two- to three-fold increase in mortality is observed for males with a resting heart rate higher than 88 beats pr. minutes (bpm) compared to a group of males with less than 65 bpm. The heart rate is not only related to cardiovascular mortality but seem also to relate to death from other causes such as cancer. It has even been hypothesized that there is a relation between low heart rate and life expectancy in general (Zaza et al., 2001).

The most common form of cardiovascular disease in the industrialized countries today is coronary artery disease (CAD) or coronary heart disease (CHD) which is the leading cause to heart attacks. CAD and CHD is a "hardening" of the arteries on the surface of the heart, where the term "hardening" refers to a condition that causes the arteries to become so narrowed and stiff that the block the free flow of blood.

Lower heart rate is related with better outcome and in particular with a reduced risk of arrhythmias. Higher heart rate may reflect a higher metabolic rate and lower vagal tone thus increasing ischemic risk. Furthermore higher heart rates may also deteriorate ventricular function (Lombardi, F in Zaza et al., 2001). Thus it is not surprising that it has been reported that an important risk factor associated with CAD or CHD is a high heart rate. CAD or CHD is frequently treated with medications. These medications fall into different categories such as:

1. Beta blockers that reduce the workload of the heart by blocking certain chemicals from binding to beta-receptors in the heart.
2. Nitrates that work directly on the blood vessels, causing them to relax and allowing more oxygen-rich blood to reach the heart.
3. Calcium channel blockers that increase blood flow through the heart and may reduce the workload of the heart by blocking calcium ions from signalling the blood vessels to constrict or tighten.

4. Anti platelets (e.g. aspirin) that inhibit the formation of blood clots by decreasing the ability of platelets (microscopic particles found in the blood) to bind together and form a blood clot.

The prevention of a high heart rate in the early stage of the development of the disease can be an alternative to treatment of high heart rate with drugs. A large number of food derived bioactive compounds are currently considered as beneficial for general well being or as health promoting.

It is known that milk fermented by lactic acid bacteria (LAB) may produce anti-hypertensive effects due to the liberation of peptides from casein in the milk by the proteolytic activity of the lactic acid bacteria. This is for instance described in EP821968 (Calpis Food Industry), EP1016709 (Calpis Food Industry) and WO0132836 (Valio Ltd.).

The article of Yamamoto et al. (1996) discloses that milk fermented with a starter containing *Lactobacillus helveticus* and *Saccharomyces cerevisiae* reduces the systolic and diastolic blood pressure, yet no changes were observed in other indexes, including pulse rate.

WO0185984 (Davisco International Foods, Inc.) also relates to peptides having anti-hypertensive effect (blood reducing effect), where the peptides from an enzymatic digest of whey protein. Changes in heart rate and blood pressure were measured. A significant reduction in mean arterial blood pressure was observed, and except for the observation of the 75 mg/kg dose, which elicited a decrease in heart rate, no significant difference between the heart rate responses occurred at the doses of 30 and 150 mg/kg.

The article of Fuglsang, A., et al. (2002) describes, as the article of Yamamoto et al. (1996), that fermented milk peptides have anti-hypertention properties. On page 3569, 1. column, 2. paragraph, it is stated in relation to tested samples that the heart rate was insignificant versus that of unfermented milk (placebo).

The above mentioned article of Yamamoto et al. (1996) and article Fuglsang (2002) and the WO0185984 document indicates that although a lactic acid bacterium fermented product has blood pressure reducing properties there are no reason to believe that it should have heart rate reducing properties as well.

SUMMARY OF THE INVENTION

The problem to be solved by the present invention is to provide an alternative composition useful for reducing heart rate.

The solution is based on that the present inventors have identified that by fermenting a food material, preferably milk, with a lactic acid bacterium (LAB), active components with increased heart rate reducing properties are obtained. For further details, see table 1 of working example 1.

Accordingly, a first aspect of the invention relates to the use of a composition obtainable by a process comprising fermenting a food material, comprising animal milk or vegetable proteins, with a lactic acid bacterium to obtain a fermented food material which comprises peptides or other active components with heart rate reducing properties for the manufacture of a product for reducing the heart rate in a mammalian.

In a second aspect, the invention provides a fermented food material having heart rate reducing properties in a mammalian and comprising active components produced by the fermentation of the food material with at least one lactic acid bacterium strain. In particular a food material fermented with *Lactobacillus helveticus* strain CHCC5951 (DSM 14998) is a preferred embodiment.

Food comprising living as well as dead bacterial is frequently claimed to be particular healthy to ingest, thus in a third aspect the invention provides a fermented food material having heart rate reducing properties in a mammalian and comprising dead or alive *Lactobacillus helveticus* strain DSM 14998 or a mutant thereof.

As can be seen from the dose-response experiment (Example 4) it appears possible to obtain even larger response if compositions were made with higher concentrations of the heart rate reducing compound(s). Thus in a fourth aspect the heart rate reducing component(s) isolated from the fermented food material is (are) provided.

In a further aspect, the invention describes the use of the fermented food material or heart rate reducing active components isolated there from for the manufacture a medicament for the treatment or relief of a coronary artery disease (CAD) or a coronary heart disease (CHD) such as angina pectoris, hypertension, atherosclerosis, stroke, myocardial infarction, cerebral infarction, and restenosis following angioplasty, arrhythmia, tachyarrythmia, congestive heart failure (CHF), aortic valve regurgitation, chronic renal failure, dyslipidemia, dyslipoproteinemia.

Definitions:

Prior to a discussion of the detailed embodiments of the invention is provided a definition of specific terms related to the main aspect of the invention.

The term "for reducing the heart rate in a mammalian" denotes reduction of heart rate in relation to the heart rate before administration of the composition as described herein. Before testing on humans, preferably the heart rate reducing properties should be determined in an animal model. In one useful animal model the fermented product is administered to spontaneous hypertensive rats (SHR) by gavage and determine the heart rate for 24 hours after gavage by telemetry in conscious SHR at different time points. Placebo should preferably be the corresponding unfermented food material such as e.g. unfermented milk. For further details see working example 1 herein. But also a model based on normotensive Wistar rats as described in Example 6 can be used to assess the reduction of heart rate.

The term "lactic acid bacterium" designates a group of Gram positive, catalase negative, non-motile, microaerophilic or anaerobic bacteria that ferment sugar with the production of acids including lactic acid as the predominantly produced acid, acetic acid, formic acid and propionic acid.

Embodiment(s) of the present invention is described below, by way of example(s) only.

DETAILED DISCLOSURE OF THE INVENTION

Food Material

The food material should comprise animal milk proteins or vegetable proteins.

Preferably it comprises animal milk proteins preferably enumerated by, for example milk protein components, such as whole or defatted animal milk or milk casein.

Food material with vegetable proteins may preferably be enumerated by, for example corn, corn protein, wheat, wheat protein, soybean, defatted soybean or soybean protein.

Product Comprising Peptides or Other Active Components with Heart Rate Reducing Properties The use of lactic acid bacteria as described herein provides directly after fermentation a useful amount of peptides or other active components with very good heart rate reducing properties. Consequently, it is not considered necessary to further purify or up-concentrate the peptides or other active components from the fermented food material. The fermented food material may be packed directly and provided to the market as a food product, preferably a functional food product, or a food product additive, e.g. in a freeze-dried form. In Example 1 this is demonstrated. In short, the results of Example 1 show that fermented milk in itself without any further treatment has good heart rate reducing effect. Further freeze-dried fermented milk could be suspended in neutral milk and thereby give a suitable food product. The freeze-dried fermented milk could therefore be seen as a suitable food additive product.

The term "functional food" denotes herein a food product where the consumer in some way is informed that it has a useful function in relation to heart rate reducing properties. When the term food is used it may also be feed. However, a food product is preferred.

Accordingly, an embodiment of the invention relates to a use as described herein where the composition is a food product comprising peptides or other active components with heart rate reducing properties obtainable by a process comprising following steps:

(i) preparing a fermented food material according to a process for preparing active components with heart rate reducing properties as described herein, (ii) drying the fermented food material, and (iii) packing it in a suitable way to get a food product or food product additive.

Step (ii) is preferably freeze-drying.

The term "packing" should be understood broadly. It denotes that once a food material is fermented and a fermented food material is obtained, the fermented food material should be packed in order to could be provided to the consumer. It may be packed in a bottle, a tetra-pack, etc. Preferably, on the package or in corresponding marketing material is indicated that the product has heart rate reducing properties. This applies for any aspects or embodiments of a product as described herein.

As shown in example 1 the lactic acid bacteria in the food product may be dead or alive, since a heat-treated fermented food material also had heart rate reducing properties.

Use of Product with Heart Rate Reducing Properties

As stated above, the term "for reducing the heart rate in a mammalian" denotes reduction of heart rate in relation to the heart rate before administration of the composition as described herein. Preferably the heart rate reducing properties should be determined by administrating the product to spontaneous hypertensive rats (SHR) by gavage and determine the heart rate for 24 hours after gavage by telemetry in conscious SHR at different time points and preferentially continuously. However also other animal models are useful for evaluating the heart rate efficacy of the fermented product. One example is the model of normotensive Wistar rats described in example 6. Placebo should preferably be the corresponding unfermented food material such as e.g. unfermented milk. For further details see working example 1 herein.

The product may be used in a treatment of a coronary artery disease (CAD) or a coronary heart disease (CHD) such as angina pectoris, hypertension, atherosclerosis, stroke, myocardial infarction, cerebral infarction, and restenosis following angioplasty, arrhythmia, tachyarrythmia, congestive heart failure (CHF), aortic valve regurgitation, chronic renal failure, dyslipidemia, dyslipoproteinemia. In such case the product is preferably a medicament. Preferred diseases are angina pectoris, hypertension, and atherosclerosis.

In addition to the conditions just mention the issue of fluctuations of the heart rate attracts interest. In Example 1, 4 and 5 it is demonstrated the fermented product effectively decreases heart rate but surprisingly also decreases fluctuations in the heart rate during the activity period of the experimental animals. In particular in stressed situations where significant heart rate fluctuations are frequently observed the damping of the fluctuations in the heart rate may be an important feature since changes in heart rate correlates with mortality in an experimental model (Zaza et al 2001).

Because coronary artery diseases tend to develop over a long period of time, there are opportunities throughout one's lifetime to prevent or control it. Preventive care can begin early, thus reducing the speed at which atherosclerosis develops. Therefore, another preferred use of the product is in a preventive manner. In such case the product may preferably be a food product or food additive, which people can consume in a daily or continuous manner.

Preferably the product has a heart rate reducing effect that is 10% over placebo where placebo is defined above as the corresponding unfermented food material. Using this definition, more preferably the product has a heart rate reducing effect that is 15% over placebo, even more preferably the product has a heart rate reducing effect that is 20% over placebo and most preferably the product has a heart rate reducing effect that is 25% over placebo.

Subsequent Purification of the Heart Rate Reducing Peptides or Other Active Components from the Fermented Food Material As stated above, the use of the lactic acid bacteria, as described herein, provides directly after the fermentation a useful amount of peptides or other active components with very good heart rate reducing properties.

However, in some circumstances it may be preferred to perform a subsequent purification of the heart rate reducing peptides or other active components from the fermented food material. This may for instance be when the peptides or other active components are to be used in a medicament such as a pharmaceutical tablet, which requires a very high concentration of the heart rate reducing peptides or other active components. Accordingly, in an embodiment of the invention the product is a medicament.

Furthermore, example 1 shows that the heart rate reducing effect is proportional to the concentration factor of the product.

Accordingly, an embodiment of the invention relates to a use as described herein where the fermented food material is further processed in a way that purify or up-concentrate the peptides or other active components with heart rate reducing properties obtainable by a process comprising following steps:

(ii) Preparing a fermented food material according to a process for preparing peptides or other active components with heart rate reducing properties as described herein, (ii) The fermented food material of step (i) is further processed in a way that purifies or up-concentrate the active components with heart rate reducing properties, (iii) Packing it in a suitable way to get a product.

This corresponds to a situation where one wants a relatively high concentration of the peptides or other active components with heart rate reducing properties in the product.

If the product is a food product the process may comprise a further step (iv) where the up-concentrated peptides or other active components of (ii) is added to the food product.

A preferred embodiment for up-concentration according to step (ii) above is where the fermented food material containing peptides or other active components with heart rate reducing properties are centrifuged, and the resulting supernatant comprising the peptides or other active components are recovered. If the food material is milk then such a product is whey. As can be seen in example 1, whey is a product with excellent heart rate reducing properties. Accordingly in a preferred embodiment the product is whey.

The centrifugation may preferably be performed, for example, at 2,000 to 20,000 rpm for 1 to 20 minutes. The centrifugation may also be performed in a centrifugator.

The resulting supernatant may be subjected to further purifying treatment with a reverse-phase resin, for obtaining a sample in which the content of the peptides or other active components with heart rate reducing properties is increased. The purifying treatment with a reverse-phase resin may be performed by absorption and elution of the peptides or other active components with a reverse-phase resin, and/or by reverse-phase chromatography, thereby increasing purity of the peptides or other active components.

For further technical details in relation to this reverse-phase resin protocol reference is made to EP821968.

Alternatively, the fermented food material is further processed in a way wherein a nanofiltration is performed on the fermented food material. This may be done in order to remove lactic acid or monovalent ions from the fermented food material.

For further technical details in relation to this nanofiltration protocol reference is made to WO01/32905.

As described in Example 4, there is a clear dosage dependent effect on the heart rate of the whey products concentrated up to a factor of 21 times. There is no indication in the experiment suggesting that a stationary or asymptotic level was reached, indicating that compositions comprising high amounts of the active compound(s) can have important uses as medicaments.

Fermentation

In the process of the present invention, the food material is fermented by lactic acid bacteria under operating conditions, which may be varied depending on the types of the food material and/or the combination of the lactic acid bacteria. Preferably, if the food material is not already an aqueous solution, food material is dissolved in a suitable aqueous solution, which is then admixed with lactic acid bacteria and cultivated by way of fermentation.

The culturing of the lactic acid bacteria may be performed by adding pre-cultured lactic acid bacteria starter to the food material medium, which may have been previously heat-sterilized and cooled to the predetermined temperature for incubation. The inoculation amount of the lactic acid bacteria starter may preferably be $10^5$ to $10^7$ cells of lactic acid bacteria/ml medium. The temperature for incubation is usually 20 to 50° C. and preferably 30 to 45° C.

The incubation time is usually 3 to 48 hours and preferably 6 to 24 hours. Particularly, it is preferred to perform cultivation in the medium having pH in a range of 3.5 to 7, more preferably 5 to 6, in order to perform cultivation of lactic acid bacteria efficiently. Further, it is preferred to perform pH-stat cultivation maintaining pH in a range of 4 to 7. The incubation may be terminated, without restriction, when the number of lactic acid bacteria exceeds $10^8$ cells/ml.

A preferred embodiment relates to a process, as described herein, wherein the fermenting of the food material is performed under conditions, which produce from 0.5 to 25 mg peptides or other active components with heart rate reducing properties per 100 ml of the food material, more preferably which produce from 1 to 5 mg peptides or other active components with heart rate reducing properties per 100 ml of the food material.

Mammalian

Mammalians include animals such as domesticated animals (e.g. cats and dogs), pigs, cows, lambs and fish. In a preferred embodiment the mammalian is a human.

Lactic Acid Bacterium

As said above, the term "lactic acid bacterium" designates a group of Gram positive, catalase negative, non-motile, microaerophilic or anaerobic bacteria that ferment sugar with the production of acids including lactic acid as the predominantly produced acid, acetic acid, formic acid and propionic acid.

Among others, it includes species of lactic acid bacteria belonging to genus *Lactobacillus*, such as *Lactobacillus helveticus, Lactobacillus delbruekii* subsp. *bulgaricus*, etc., lactic acid bacteria belonging to genus *Lactococcus*, such as *Lactococcus lactis*, lactic acid bacteria belonging to genus *Streptococcus*, such as *Streptococcus salivarius* subsp. *thermophilus*, lactic acid bacteria belonging to genus *Leuconostoc*, such as *Leuconostoc lactis*, lactic acid bacteria belonging to genus *Bifidobacterium*, such as *Bifidobacterium longum* or *Bifidobacterium breve*, and lactic acid bacteria belonging to genus *Pediococcus*.

The lactic acid bacteria may be used as a mixture with other microorganisms, e.g. yeasts.

Numerous different lactic acid bacteria are public available to the skilled person. Reference is e.g. made to Deutsche Sammlung von Mikroorganismen und Zellkulturen GmbH (DSMZ); and the Internet taxonomy browser of NCBI.

Preferably, the lactic acid bacterium is a bacterium of the phylium Firmicutes, more preferably of the class *Bacilli*, even more preferably of the order *Lactobacillales*. Within this order a preferred lactic acid bacterium is a bacterium of the family *Lactobacillaceae*, more preferably of the genus *Lactobacillus*. Preferably it is a *Lactobacillus helveticus* strain. For further details in relation to taxonomy reference is made to (Bergey's Manual of Systematic Bacteriology, Second Edition, Volume 1: The Archea and the Deeply Branching and Phototrophic Bacteria).

A sample of a particular preferred *Lactobacillus helveticus* strain CHCC5951 has been deposited at the International Depository DSMZ (Deutsche Sammlung von Mikroorganismen und Zellkulturen GmbH, German Collection of Microorganisms and Cell Cultures Ltd.) located at Mascheroder Weg 1b, D-38124 Braunschweig, Germany under the accession number DSM 14998 with a deposit date of 15 May 2002. The deposit has been made under the conditions of the Budapest Treaty on the International Recognition of the Deposit of Microorganisms for the Purposes of Patent Procedure.

Accordingly, a particular preferred embodiment relates to a use as described herein where the lactic acid bacterium is *Lactobacillus helveticus* with the registration number DSM 14998.

Further, a sample of a *Lactobacillus helveticus* strain CHCC4080 has been deposited at DSMZ (Deutsche Sammlung von Mikroorganismen und Zellkulturen GmbH) under the accession number DSM 14997 with a deposit date of $15^{th}$ May 2002. The deposit has been made under the conditions of the Budapest Treaty on the International Recognition of the Deposit of Micro organisms for the Purposes of Patent Procedure.

Further preferred organisms are *Lactobacillus helveticus* strain with deposit accession number FERM BP-4835, *Lactobacillus helveticus* strain with deposit accession number FERM BP-6060, *Lactobacillus helveticus* strain with deposit accession number DSM 13137, *Lactobacillus helveticus* CNRZ32 strain and *Lactobacillus helveticus* CP790 strain.

LAB Comprising a 200 kDa Cell Wall Proteinase

A preferred lactic acid bacterium is one that comprises a specific cell wall proteinase of around 200 kDa. Such a lactic acid bacterium is particular suitable to prepare peptides or other active components with heart rate reducing properties. This preferred LAB is described in detail below.

The specific cell wall proteinase is herein termed prtH200. The prtH200 proteinase, as described in this section, correspond to the prtH 204 kDa cell wall proteinase from the *Lactobacillus helveticus* CNRZ32 strain described in the article of University of Wisconsin and Utah State University [Pederson et al (1999, J. of Bacteriology, 181: 4592-4597)]. In this article it is not described nor suggested to use the CNRZ32 strain to make peptides or other active components with heart rate reducing properties.

The lactic acid bacterium is characterized in that it comprises a gene sequence encoding a cell wall proteinase (termed prtH200), wherein the gene sequence is defined as prtH200 is a DNA sequence encoding an enzyme exhibiting cell wall proteinase activity, which DNA sequence is selected from the group comprising of:

(a) The DNA sequence shown in positions 1-5550 in SEQ ID NO 1;

(b) A DNA sequence comprising a fragment of at least 75 base pairs (bp) that is at least 50% identical to a corresponding fragment of the DNA sequence defined in (a);

(c) A DNA sequence that encodes a polypeptide, exhibiting cell wall proteinase activity, comprising a fragment of at least 200 amino acids (aa) that is at least 30% identical to a corresponding fragment of the polypeptide sequence shown in positions 1-1849 of SEQ ID NO 2;

(d) A DNA sequence which hybridizes with a double-stranded DNA probe comprising the DNA sequence shown in positions 1-5550 in SEQ ID NO 1 at low stringency; and (e) A DNA sequence which is a fragment of the DNA sequences specified in (a), (b), (c), or (d).

The presence, in a lactic acid bacterium, of a gene sequence encoding the prtH200 proteinase may preferably be verified by PCR amplification using suitable designed PCR primers. When the skilled person has suitable designed PCR primers it is easy for him to verify the presence or not of the gene sequence in a lactic acid bacterium using his general knowledge to make a specific suitable PCR amplification protocol.

Consequently, the skilled person may rapidly screen a number of lactic acid bacteria, identify the ones comprising a prtH200 gene sequence, and thereby obtain specific selected lactic acid bacteria with improved industrial relevant characteristics.

A sample of a particular preferred *Lactobacillus helveticus* strain CHCC5951 has been deposited at DSMZ (Deutsche Sammlung von Mikroorganismen und Zellkulturen GmbH) under the accession number DSM 14998 with a deposit date of $15^{th}$ May 2002. The deposit has been made under the conditions of the Budapest Treaty on the International Recognition of the Deposit of Micro organisms for the Purposes of Patent Procedure.

Accordingly, a particular preferred embodiment relates to a use as described in this section where the lactic acid bacterium is *Lactobacillus helveticus* with the registration number DSM 14998.

Using as starting material the deposited the deposited DSM 14998 strain, the skilled reader can by conventional mutagenesis or re-isolation techniques obtain further mutants or derivatives which retain the ability to be suitable for preparing peptides or other active components with heart rate reducing properties.

Proteolytic Activity of the Lactic Acid Bacteria

The prtH200, orfF3 and orfF4 gene sequences as described in this section may be seen as fingerprints highly suitable to identity useful lactic acid bacteria as described in this section. Without being limited to theory, theoretically it may be that some strains could exist that despite comprising the fingerprint gene sequence(s) as described in this section are not exhibiting the advantageous properties as described in this section.

Accordingly, once having identified, in a lactic acid bacterium, the presence of fingerprint gene sequence(s) as described in this section, it may be advantageous to test the proteolytic activity of the lactic acid bacterium. In the present context, a preferred lactic acid bacterium has preferably a proteolytic activity as described below.

In the present context, a lactic acid bacterium is considered to have proteolytic activity when it is capable of synthesizing an active cell wall proteinase. In other words, capable of proving a proteinase, which is active outside the intracellular part of the bacterium. Further, the proteinase should have a specificity making it capable of degrading proteins (e.g. casein comprised in milk) to obtain peptides or other active components with heart rate reducing properties.

Preferably, the proteolytic activity of a bacterium is ascertained by a protocol comprising the steps:

(i) Fermenting overnight 200 ml of a food material with the bacterium, (ii) Extracting the produced peptides or other active components, and (iii) Measuring the heart rate reducing properties of the extracted peptides or other active components by an assay measuring the peptidic concentration required to inhibit 50% of the ACE activity.

The ACE inhibition activity assay is herein also termed DL50. The lower the DL50 value is the better is the heart rate effect of the peptides or other active components comprised in the product.

In step (i) of the protocol, the food material is preferably fresh milk. Further, the bacterium is preferably inoculated to the food material in the form of an overnight stock culture of (1% v/v) and maintained overnight at a suitable temperature. A suitable temperature is a temperature that is suitable for growth of the bacterium. The skilled person knows how to identify this for a particular lactic acid bacterium. For *Lactobacillus* species a suitable temperature is 37° C. and for *Lactococcus* species a suitable temperature is 30° C.

In working example 3 herein is provided a detailed preferred protocol for the fermenting and extracting steps and a detailed preferred protocol for the DL50 ACE activity assay.

Preferably, the lactic acid bacterium has a proteolytic activity making it capable of, in a protocol comprising the steps:

(i) Fermenting overnight 200 ml of a food material with the bacterium, (ii) Extracting the produced peptides or other active components, and (iii) Measuring the anti-hypertensive properties of the extracted peptides or other active components by an assay measuring the peptidic concentration required to inhibit 50% of the ACE activity (DL50), Producing peptides or other active components with an angiotensin-converting enzyme (ACE) inhibition activity (DL50) of from 0.25 to 5.0 (mg/ml).

More preferably, the lactic acid bacterium is capable of producing peptides or other active components with an angiotensin-converting enzyme (ACE) inhibition activity (DL50) of from 0.25 to 4.0 (mg/ml), and even more preferably the proteolytic lactic acid bacterium is capable of producing peptides or other active components with an angiotensin-converting enzyme (ACE) inhibition activity (DL50) of from 0.25 to 3.5 (mg/ml).

The lower DL50 range may be, instead of 0.25 mg/ml, 1.0 mg/ml.

The term "gene" is herein defined according to is usual meaning as the fundamental physical and functional unit of heredity. A gene is an ordered sequence of nucleotides (e.g. DNA or RNA) located in a particular position on a particular chromosome that encodes a specific functional product (i.e., a protein or RNA molecule).

The "nomenclature of degenerated primers" is according to the standard nomenclature in the art. Y=C or T; R=A or G; M=A or C; K=G or T; S=G or C; W=A or T; H=A or C or T; B=G or T or C; V=G or C or A; D=G or A or T; N=G, A, C or T.

The term a "fragment" in relation to a DNA/amino acid sequence comprising a fragment denotes a continuous partial sequence. For instance, from position 75 to 300 in an amino acid sequence having 600 amino acids.

The term "a corresponding fragment" in relation to identity comparison between two sequences relates to a fragment of corresponding size. Preferably, the size difference, between the two fragments to be compared, is less than 50%. In order words, if one fragment is 100 bp the other is preferably less than 150 bp. More preferably, the size difference, between the two fragments to be compared, is less than 25%, and even more preferably the size difference, between the two fragments to be compared, is less than 5%.

prtH200 Cell Wall Proteinase

The activity of a cell wall proteinase is preferably verified while it is present in the lactic acid bacteria. A suitable strategy is to construct a lactic acid bacterium with a lethal mutation in the gene encoding the cell wall proteinase to be analysed. The proteolytic activity (for a suitable assay see below) of this constructed bacterium could then be compared with the corresponding wild type bacterium. A measurable decrease in proteolytic activity of the lactic acid bacterium with a lethal mutation as compared with the corresponding wild type bacterium would experimentally confirm that the gene encoding the cell wall proteinase to be analysed is a gene encoding an active lactic acid cell wall proteinase.

The skilled person knows how to construct a lactic acid bacterium with a suitable lethal mutation. Reference is made to e.g. Pederson et al (1999) and Yamamoto et al (1994) (see above).

At the filing date of the present invention, the National Center for Biotechnology Information (NCBI) offered at its Internet site the possibility of making a standard BLAST computer sequence homology search.

The DNA and amino acid sequence of prtH200 of *Lactobacillus helveticus* DSM 14998 as shown in SEQ ID NO 1 and SEQ ID NO 2 has been published at the GeneBank database with accession number AF133727. The database sequence identification is gi|5758038|gb|AF133727.1|AF133727.

Standard protein-protein BLAST [blastp] search using the prtH200 amino acid sequence shown in position 1-1849 in SEQ ID NO 2 as reference sequence gave, among others, following results (in italic is given the database sequence identification. This info unambiguously identifies the published sequence and the skilled person know how to get the sequence based on this):

gi|129346|sp|P15293|P2P_LACLC: P1'-type proteinase precursor (Lactocepin) (Cell wall-associated serine proteinase). Organism: *Lactococcus lactis* subsp. *cremoris.*

Identity: a 1600 amino acid fragment with 50% identity of to a corresponding fragment of the prtH200 amino acid sequence of SEQ ID NO 2.

gi|149582|gb|AAA25248.1|: proteinase Organism: *Lactobacillus paracasei.*

Identity: a 1632 amino acid fragment with 49% identity of to a corresponding fragment of the prtH200 amino acid sequence of SEQ ID NO 2.

gi|1381114gb|AAC41529.1|: (L48487) proteinase precursor Organism: *Lactobacillus delbrueckii.*

Identity: a 1682 amino acid fragment with 32% identity of to a corresponding fragment of the prtH200 amino acid sequence of SEQ ID NO 2.

gi|18568398|gb|AAL76069.1|: (AF468027) cell-envelope proteinase. Organism: *Lactobacillus pentosus.*

Identity: a 415 amino acid fragment with 63% identity of to a corresponding fragment of the prtH200 amino acid sequence of SEQ ID NO 2.

gi|9963932|gb|AAG09771.11AF243528_1: (AF243528) cell envelope proteinase.

Organism: *Streptococcus thermophilus*

Identity: a 781 amino acid fragment with 30% identity of to a corresponding fragment of the prtH200 amino acid sequence of SEQ ID NO 2.

gi|482386|pir||A44833: lactocepin (EC 3.4.21.96). Organism: *Lactococcus* lactis.

Identity: a 264 amino acid fragment with 61% identity of to a corresponding fragment of the prtH200 amino acid sequence of SEQ ID NO 2.

These specific sequences are all representing a DNA sequence that encodes a polypeptide, exhibiting cell wall proteinase activity, comprising a fragment of at least 200 amino acids (aa) that is at least 30% identical to a corresponding fragment of the polypeptide sequence shown in positions 1-1849 of SEQ ID NO 2.

Standard nucleotide-nucleotide BLAST [blastn] search using the prtH200 DNA sequence shown in position 1-5550 in SEQ ID NO 1 as reference sequence gave, among others, following results gi|149580|gb|M83946.1|LBAMPRO. Proteinase (prtP) gene. Organism:

*Lactobacillus paracasei.*

Identity: a 102 bp fragment with 84% identity of to a corresponding fragment of the prtH200 DNA sequence of SEQ ID NO 1.

gi|47197|emb|X14130.1SLPRT763. plasmid pLP763 prt gene for cell wall-associated serine proteinase. Organism: *Streptococcus lactis*

Identity: a 81 bp fragment with 86% identity of to a corresponding fragment of the prtH200 DNA sequence of SEQ ID NO 1.

gi|472834|gb|M24767.1|STRWGPROT. Wg2 proteinase gene. Organism: *S. cremoris*

Identity: a 81 bp fragment with 86% identity of to a corresponding fragment of the prtH200 DNA sequence of SEQ ID NO 1.

gi|149476|gb|J04962.1|LACPRASE. PIII-type proteinase (prtP) and maturation protein. Organism: *Lactococcus lactis.*

Identity: a 81 bp fragment with 86% identity of to a corresponding fragment of the prtH200 DNA sequence of SEQ ID NO 1.

gi|18568397|gb|AF468027.1|. cell-envelope proteinase (prtP) gene. Organism: *Lactobacillus pentosus*

Identity: a 102 bp fragment with 83% identity of to a corresponding fragment of the prtH200 DNA sequence of SEQ ID NO 1.

These specific sequences are all representing a DNA sequence comprising a fragment of at least 75 base pairs (bp) that is at least 50% identical to a corresponding fragment of the DNA sequence shown in positions 1-5550 of SEQ ID NO 1.

Other "Fingerprint" Gene Sequences (orfF3 and orfF4):

orfF3:

Preferably, beside a prtH200 gene sequence the LAB also comprises a gene comprising an open reading frame herein termed orfF3. This gene may be seen as an additional fingerprint.

The DNA and amino acid sequence of orfF3 of *Lactobacillus helveticus* DSM 14998 is shown in SEQ ID NO 3 and SEQ ID NO 4.

Accordingly in a preferred embodiment, a lactic acid bacterium, as described in this section, comprises the prtH200 gene and a gene sequence (termed orfF3) encoding an open reading frame wherein the gene sequences is identifiable by PCR amplification of genomic DNA of the lactic acid bacterium using sets of PCR primers selected from the group consisting of [sense sequence (S); antisense sequence (A)]:

```
orfF3:  (a):  (S):  5' CGAAGGCGATAAGTCAAACTTTGA
                    TAATGC 3',
              (A):  5' CCCGGTTCTGTAAGATAATTTGGA
                    TCG 3'; and
        (b):  (S):  5' ASTCWRRYTTYGATRATGCW 3',
              (A):  5' BHKYAMSAWARTTTGGATCR 3'.
```

As said above suitable PCR primers may be identified based on the sequences disclosed herein.

Accordingly, in a preferred embodiment, a lactic acid bacterium, as described in this section, comprises the prtH200 gene and a gene sequence encoding an open reading frame (termed orfF3), wherein the gene sequence is defined as orfF3 is a DNA sequence encoding an open reading frame, which DNA sequence is selected from the group comprising of:

(a) The DNA sequence shown in positions 1-2679 in SEQ ID NO 3;

(b) A DNA sequence comprising a fragment of at least 75 base pairs (bp) that is at least 40% identical to a corresponding fragment of the DNA sequence defined in (a);

(c) A DNA sequence that encodes a polypeptide comprising a fragment of at least 200 amino acids (aa) that is at least 30% identical to a corresponding fragment of the polypeptide sequence shown in positions 1-893 of SEQ ID NO 4;

(d) A DNA sequence which hybridises with a double-stranded DNA probe comprising the DNA sequence shown in positions 1-2679 in SEQ ID NO 3 at low stringency; and (e) A DNA sequence which is a fragment of the DNA sequences specified in (a), (b), (c), or (d).

The term "open reading frame" denotes a stretch of DNA that contains a signal for the start of translation followed in the correct register by a sufficient length of amino acid encoding triplets to form a protein, followed by a signal for termination of translation, and which may therefore indicate the presence of a protein coding gene.

At the filing date of the present application, a standard protein-protein BLAST [blastp] search using the deduced orfF3 amino acid sequence shown in position 1-893 in SEQ ID NO 4 as reference sequence gave relatively limited conclusive results in relation to published homologous sequences.

However, without being limited to theory, it is believed that an orfF3 gene as described in this section encodes a cell wall proteinase. Consequently, in a preferred embodiment the orfF3 gene as described in this section encodes a cell wall proteinase.

orfF4:

Preferably, beside a prtH200 gene sequence the LAB also comprises a gene comprising an open reading frame herein termed orfF4.

The DNA and amino acid sequence of orfF4 of *Lactobacillus helveticus* DSM 14998 is shown in SEQ ID NO 5 and SEQ ID NO 6.

Accordingly in a preferred embodiment, a lactic acid bacterium, as described in this section, comprises the prtH200 gene and a gene sequence (termed orfF4) encoding an open reading frame wherein the gene sequences is identifiable by PCR amplification of genomic DNA of the lactic acid bacterium using sets of PCR primers selected from the group consisting of [sense sequence (S); antisense sequence (A)]:

```
orfF4:  (a):  (S):  5' GGTGTTGCTCCTGAAGC 3'
              (A):  5' ACTCTAGCACCAGCTAATTG
                    AACATCATG 3'.
```

As said above suitable PCR primers may be identified based on the sequences disclosed herein.

Accordingly, in a preferred embodiment, a lactic acid bacterium, as described in this section, comprises the prtH200 gene and a gene sequence encoding an open reading frame (termed orfF4), wherein the gene sequence is defined as orfF4 is a DNA sequence encoding an open reading frame, which DNA sequence is selected from the group comprising of:

(a) The DNA sequence shown in positions 1-4881 in SEQ ID NO 5;

(b) A DNA sequence comprising a fragment of at least 75 base pairs (bp) that is at least 40% identical to a corresponding fragment of the DNA sequence defined in (a);

(c) A DNA sequence that encodes a polypeptide comprising a fragment of at least 200 amino acids (aa) that is at least 30% identical to a corresponding fragment of the polypeptide sequence shown in positions 1-1627 of SEQ ID NO 6;

(d) A DNA sequence which hybridises with a double-stranded DNA probe comprising the DNA sequence shown in positions 1-4881 in SEQ ID NO 5 at low stringency; and (e) A DNA sequence which is a fragment of the DNA sequences specified in (a), (b), (c), or (d).

At the filing date of the present application, a standard protein-protein BLAST [blastp] search using the deduced orfF4 amino acid sequence shown in position 1-1627 in SEQ ID NO 6 as reference sequence gave relatively limited conclusive results in relation to published homologous sequences.

However, without being limited to theory, it is believed that an orfF4 gene as described in this section encodes a cell wall proteinase. Consequently, in a preferred embodiment the orfF4 gene as described in this section encodes a cell wall proteinase.

Preferably, a lactic acid bacterium, as described in this section, comprises the prtH200 gene, the orfF3 gene and the orf4 gene as described in this section.

PCR Amplification

As said above, the presence of the gene sequences, as described in this section, may preferably be verified by PCR amplification using PCR primers designed according to the teaching herein. When the skilled person has suitable designed PCR primers it is easy for him to verify the presence or not of these genes in a lactic acid bacterium using his general knowledge to make a specific suitable PCR amplification protocol.

Preferably the PCR amplification protocol (reaction) is made according to the description of Example 2 herein.

Once the PCR have been performed it is routine for the skilled person to investigate whether or not the resulting PCR amplified fragments corresponds to fragments of genes as described in this section. Normally this may be identified already based on the size of the PCR fragment, since the skilled person generally roughly knows how big the size of a positive PCR fragment would be. A positive PCR fragment relates to a PCR fragment of a gene as described in this section. Alternatively, the PCR fragment may be DNA sequenced and the resulting DNA sequence may then be compared with the sequences disclosed herein. Further, a lactic acid bacterium with a lethal mutation in the gene corresponding to the PCR fragment could be constructed. The proteolytic activity (see below) of this constructed bacterium could then be compared with the corresponding wildtype bacterium and a measurable change in proteolytic activity between the two cells would experimentally confirm whether or not the gene corresponding to the amplified PCR fragment is a gene encoding a lactic acid cell wall proteinase as described in this section. In summary, the skilled person can routinely identify whether or not a specific lactic acid bacterium comprises gene(s) capable of giving corresponding positive PCR fragments using PCR primers designed according to the teaching herein.

PCR is the preferred way to investigate the presence or not in the lactic acid bacteria of the genes as described in this section. However, it may be done in other ways such as e.g. by Southern blot analysis.

PCR Primers

As explained above suitable PCR primers in relation to the PrtH200 gene are:

```
PrtH200: (a): (S): 5' CGATGATAATCCTAGCGAGC3',
              (A): 5' TGGCAGAACCTGTGCCTA 3';
         (b): (S): 5' GCCAAGACGCCTCTGGTA 3',
              (A): 5' TAGGTATAGTTTCCATCAGGA 3'; and
         (c): (S): 5' AARGTWCCWTAYGGYYWYAAYTA 3',
              (A): 5' GCCATDSWDGTRCCDSWCATDTK 3'.
```

PrtH200: (a): (S) is shown in SEQ ID NO 7; PrtH200: (a): (A) is shown in SEQ ID NO 8;

PrtH200: (b): (S) is shown in SEQ ID NO 9; PrtH200: (b): (A) is shown in SEQ ID NO 10;

PrtH200: (c): (S) is shown in SEQ ID NO 11; PrtH200: (c): (A) is shown in SEQ ID NO 12.

When using the primer set (a) the amplified PrtH200 PCR fragment should preferably be of a size between 400 bp and 800 bp, more preferably of a size between 500 bp and 700 bp.

When using the primer set (b) the amplified PrtH200 PCR fragment should preferably be of a size between 200 bp and 500 bp, more preferably of a size between 250 bp and 375 bp.

When using the primer set (c) the amplified PrtH200 PCR fragment should preferably be of a size between 400 bp and 800 bp, more preferably of a size between 500 bp and 700 bp.

The most preferred PrtH200 related PCR primers are primer set (a) and primer set (b).

As said above suitable PCR primers in relation to orfF3 are:

```
orfF3: (a): (S): 5' CGAAGGCGATAAGTCAAACTTTGA
                    TAATGC 3',
            (A): 5' CCCGGTTCTGTAAGATAATTTGGA
                    TCG 3'; and
       (b): (S): 5' ASTCWRRYTTYGATRATGCW 3',
            (A): 5' BHKYAMSAWARTTTGGATCR 3'.
```

orfF3: (a): (S) is shown in SEQ ID NO 13; orfF3: (a): (A) is shown in SEQ ID NO 14;

orfF3: (b): (S) is shown in SEQ ID NO 15; orfF3: (b): (A) is shown in SEQ ID NO 16.

When using the primer set (a) the amplified orfF3 PCR fragment should preferably be of a size between 1250 bp and 1900 bp, more preferably of a size between 1500 bp and 1725 bp.

When using the primer set (b) the amplified orfF3 PCR fragment should preferably be of a size between 1250 bp and 1900 bp, more preferably of a size between 1500 bp and 1725 bp.

The most preferred orfF3 related PCR primers are the primer set (a).

As said above suitable PCR primers in relation to orfF4 is:

```
orfF4: (a): (S): 5' GGTGTTGCTCCTGAAGC 3'
            (A): 5' ACTCTAGCACCAGCTAATTG
                    AACATCATG 3'.
```

orfF4: (a): (S) is shown in SEQ ID NO 17; orfF4: (a): (A) is shown in SEQ ID NO 18.

When using the primer set (a) the amplified orfF4 PCR fragment should preferably be of a size between 700 bp and 1150 bp, more preferably of a size between 875 bp and 1025 bp.

Homology/Identity of DNA Sequences

The DNA sequence homology/identity referred to above is determined as the degree of identity between two sequences indicating a deviation of the first sequence from the second.

At the filing date of the present invention, the National Center for Biotechnology Information (NCBI) offered at it Internet site the possibility of making a standard BLAST computer sequence homology search.

BLAST program is described in [Altschul et al (1997), "Gapped BLAST and PSI-BLAST: a new generation of protein database search programs", Nucleic Acids Res. 25:3389-3402].

In the present context, a preferred computer homology search program is a "Standard nucleotide-nucleotide BLAST [blastn]" search as specified, at the filing date of the present application, at the NCBI Internet site with setting filter: Low complexity; Expect: 10, Word Size: 11.

The reference sequence is introduced into the program and the program identifies fragments of published sequences together the identity percentage to a corresponding fragment of the reference sequence.

Using this Standard nucleotide-nucleotide BLAST computer program, a prtH200 sequence as described in this section is preferably a DNA sequence comprising a fragment of at least 75 base pairs (bp) that is at least 60% identical to a corresponding fragment of the prtH200 DNA sequence shown in position 1-5550 of SEQ ID NO 1, more preferably a DNA sequence comprising a fragment of at least 75 base pairs (bp) that is at least 70% identical to a corresponding fragment of the prtH200 DNA sequence shown in position 1-5550 of SEQ ID NO 1, and even more preferably a DNA sequence comprising a fragment of at least 75 base pairs (bp) that is at least 80% identical to a corresponding fragment of the prtH200 DNA sequence shown in position 1-5550 of SEQ ID NO 1.

With the identity percentages given above, it is preferred that the fragment is at least 100 bp pairs (bp), more preferably that the fragment is at least 200 bp pairs (bp), even more preferably that the fragment is at least 400 bp pairs (bp), and most preferably that the fragment is at least 1500 bp pairs (bp).

Using this Standard nucleotide-nucleotide BLAST computer program, a orfF3 sequence as described in this section is preferably a DNA sequence comprising a fragment of at least 75 base pairs (bp) that is at least 60% identical to a corresponding fragment of the orfF3 DNA sequence shown in position 1-2679 of SEQ ID NO 3, more preferably a DNA sequence comprising a fragment of at least 75 base pairs (bp) that is at least 70% identical to a corresponding fragment of the orfF3 DNA sequence shown in position 1-2679 of SEQ ID NO 3, and even more preferably a DNA sequence comprising a fragment of at least 75 base pairs (bp) that is at least 80% identical to a corresponding fragment of the orfF3 DNA sequence shown in position 1-2679 of SEQ ID NO 3.

With the identity percentages given above, it is preferred that the fragment is at least 100 bp pairs (bp), more preferably that the fragment is at least 200 bp pairs (bp), even more preferably that the fragment is at least 400 bp pairs (bp), and most preferably that the fragment is at least 1500 bp pairs (bp).

Using this Standard nucleotide-nucleotide BLAST computer program, a orfF4 sequence as described in this section is preferably a DNA sequence comprising a fragment of at least 75 base pairs (bp) that is at least 60% identical to a corresponding fragment of the orfF4 DNA sequence shown in position 1-4881 of SEQ ID NO 5, more preferably a DNA sequence comprising a fragment of at least 75 base pairs (bp) that is at least 70% identical to a corresponding fragment of the orfF4 DNA sequence shown in position 1-4881 of SEQ ID NO 5, and even more preferably a DNA sequence comprising a fragment of at least 75 base pairs (bp) that is at least 80% identical to a corresponding fragment of the orfF4 DNA sequence shown in position 1-4881 of SEQ ID NO 5.

With the identity percentages given above, it is preferred that the fragment is at least 100 bp pairs (bp), more preferably that the fragment is at least 200 bp pairs (bp), even more preferably that the fragment is at least 400 bp pairs (bp), and most preferably that the fragment is at least 1500 bp pairs (bp).

Alternatively, the homology/identity may suitably be determined by means of computer programs known in the art, such as GAP provided in the GCG program package (Program Manual for the Wisconsin Package, Version 8, August 1994, Genetics Computer Group, 575 Science Drive, Madison, Wis., USA 53711)(Needleman, S. B. and Wunsch, C. D., (1970), Journal of Molecular Biology, 48, 443-453).

Using GAP with the following settings for DNA sequence comparison, GAP creation penalty of 5.0 and GAP extension penalty of 0.3, the preferred identity percentages given above in relation to the BLAST program are also the preferred identities when using GAP.

Homology to Amino Acid Sequences

Similar to the nucleotide homology analysis, in the present context, a preferred computer homology search program is a "Standard protein-protein BLAST [blastp]" search as specified, at the filing date of the present application, at the NCBI Internet site with settings Composition-based statistics: yes, filter: Low complexity; Expect: 10, Word Size: 3, Matrix: BLOSUM 62, Gap Costs: Existence 11 Extension 1.

Using this standard protein-protein BLAST computer program, a prtH200 sequence as described in this section is preferably a DNA sequence that encodes a polypeptide, exhibiting cell wall proteinase activity, comprising a fragment of at least 200 amino acids (aa) that is at least 40% identical to a corresponding fragment of the prtH200 polypeptide sequence shown in positions 1-1849 of SEQ ID NO 2, more preferably a DNA sequence that encodes a polypeptide, exhibiting cell wall proteinase activity, comprising a fragment of at least 200 amino acids (aa) that is at least 50% identical to a corresponding fragment of the prtH200 polypeptide sequence shown in positions 1-1849 of SEQ ID NO 2, even more preferably a DNA sequence that encodes a polypeptide, exhibiting cell wall proteinase activity, comprising a fragment of at least 200 amino acids (aa) that is at least 65% identical to a corresponding fragment of the prtH200 polypeptide sequence shown in positions 1-1849 of SEQ ID NO 2, and most preferably a DNA sequence that encodes a polypeptide, exhibiting cell wall proteinase activity, comprising a fragment of at least 200 amino acids (aa) that is at least 80% identical to a corresponding fragment of the prtH200 polypeptide sequence shown in positions 1-1849 of SEQ ID NO 2.

With the identity percentages given above, it is preferred that the fragment is at least 300 amino acids (aa), more preferably that the fragment is at least 400 amino acids (aa), even more preferably that the fragment is at least 800 amino acids (aa), and most preferably that the fragment is at least 1200 amino acids (aa).

Using this standard protein-protein BLAST computer program, a orfF3 sequence as described in this section is preferably a DNA sequence that encodes a polypeptide comprising a fragment of at least 200 amino acids (aa) that is at least 40% identical to a corresponding fragment of the orfF3 polypeptide sequence shown in positions 1-893 of SEQ ID NO 4, more preferably a DNA sequence that encodes a polypeptide comprising a fragment of at least 200 amino acids (aa) that is at least 50% identical to a corresponding fragment of the orfF3 polypeptide sequence shown in positions 1-893 of SEQ ID NO 4, even more preferably a DNA sequence that encodes a polypeptide comprising a fragment of at least 200 amino acids (aa) that is at least 65% identical to a corresponding fragment of the orfF3 polypeptide sequence shown in positions 1-893 of SEQ ID NO 4, and most preferably a DNA sequence that encodes a polypeptide comprising a fragment of at least 200 amino acids (aa) that is at least 80% identical to a corresponding fragment of the orfF3 polypeptide sequence shown in positions 1-893 of SEQ ID NO 4.

With the identity percentages given above, it is preferred that the fragment is at least 300 amino acids (aa), more preferably that the fragment is at least 400 amino acids (aa), even more preferably that the fragment is at least 800 amino acids (aa), and most preferably that the fragment is at least 1200 amino acids (aa).

Using this standard protein-protein BLAST computer program, a orfF4 sequence as described in this section is preferably a DNA sequence that encodes a polypeptide comprising a fragment of at least 200 amino acids (aa) that is at least 40% identical to a corresponding fragment of the orfF4 polypeptide sequence shown in positions 1-1627 of SEQ ID NO 6, more preferably a DNA sequence that encodes a polypeptide comprising a fragment of at least 200 amino acids (aa) that is at least 50% identical to a corresponding fragment of the orfF4 polypeptide sequence shown in positions 1-1627 of SEQ ID NO 6, even more preferably a DNA sequence that encodes a polypeptide comprising a fragment of at least 200 amino acids (aa) that is at least 65% identical to a corresponding fragment of the orfF4 polypeptide sequence shown in positions 1-1627 of SEQ ID NO 6, and most preferably a DNA sequence that encodes a polypeptide comprising a fragment of at least 200 amino acids (aa) that is at least 80% identical to a corresponding fragment of the orfF4 polypeptide sequence shown in positions 1-1627 of SEQ ID NO 6.

With the identity percentages given above, it is preferred that the fragment is at least 300 amino acids (aa), more preferably that the fragment is at least 400 amino acids (aa), even more preferably that the fragment is at least 800 amino acids (aa), and most preferably that the fragment is at least 1200 amino acids (aa).

Alternatively, the homology may suitably be determined by means of computer programs known in the art such as GAP provided in the GCG program package (Program Manual for the Wisconsin Package, Version 8, August 1994, Genetics Computer Group, 575 Science Drive, Madison, Wis., USA 53711) (Needleman, S. B. and Wunsch, C. D., (1970), Journal of Molecular Biology, 48, 443-453.

Using GAP with the following settings for polypeptide sequence comparison: GAP creation penalty of 3.0 and GAP extension penalty of 0.1, the preferred identity percentages given above in relation to the BLAST program are also the preferred identities when using GAP Hybridisation The hybridisation referred to above is intended to comprise an analogous DNA sequence, which hybridises to a double-stranded DNA probe. Suitable experimental conditions for determining hybridisation at low, medium, or high stringency between a nucleotide probe and a homologous DNA or RNA sequence involve pre-soaking of the filter containing the DNA fragments or RNA to hybridise in 5×SSC (Sodium chloride/Sodium citrate, Sambrook et al. 1989) for 10 min, and prehybridization of the filter in a solution of 5×SSC, 5× Denhardt's solution (Sambrook et al. 1989), 0.5% SDS and 100 mu g/ml of denatured sonicated salmon sperm DNA (Sambrook et al. 1989), followed by hybridisation in the same solution containing 10 ng/ml of a random-primed (Feinberg, A. P. and Vogelstein, B. (1983) Anal. Biochem. 132:6-13), P-dCTP-labeled (specific activity>1×10 cpm/mu g) probe for 12 hours at 45° C. The filter is then washed twice for 30 minutes in 2×SSC, 0.5% SDS at a temperature of at least 55° C. (low stringency), more preferably at least 60° C. (medium stringency), still more preferably at least 65° C. (medium/high stringency), even more preferably at least 70° C. (high stringency), even more preferably at least 75° C. (very high stringency).

Molecules to which the oligonucleotide probe hybridises under these conditions are detected using an X-ray film.

LEGENDS TO FIGURES

FIG. 1. Heart rate measurements in animals treated with concentration 3 (whey compositions containing solid whey components concentrated factor of 14.3 times) or placebo. Each data point is representing the average value from 8 animals. Note that the activity period of the animals is coincident with the period without light, i.e. the period indicated by the black bar.

Figure 2:
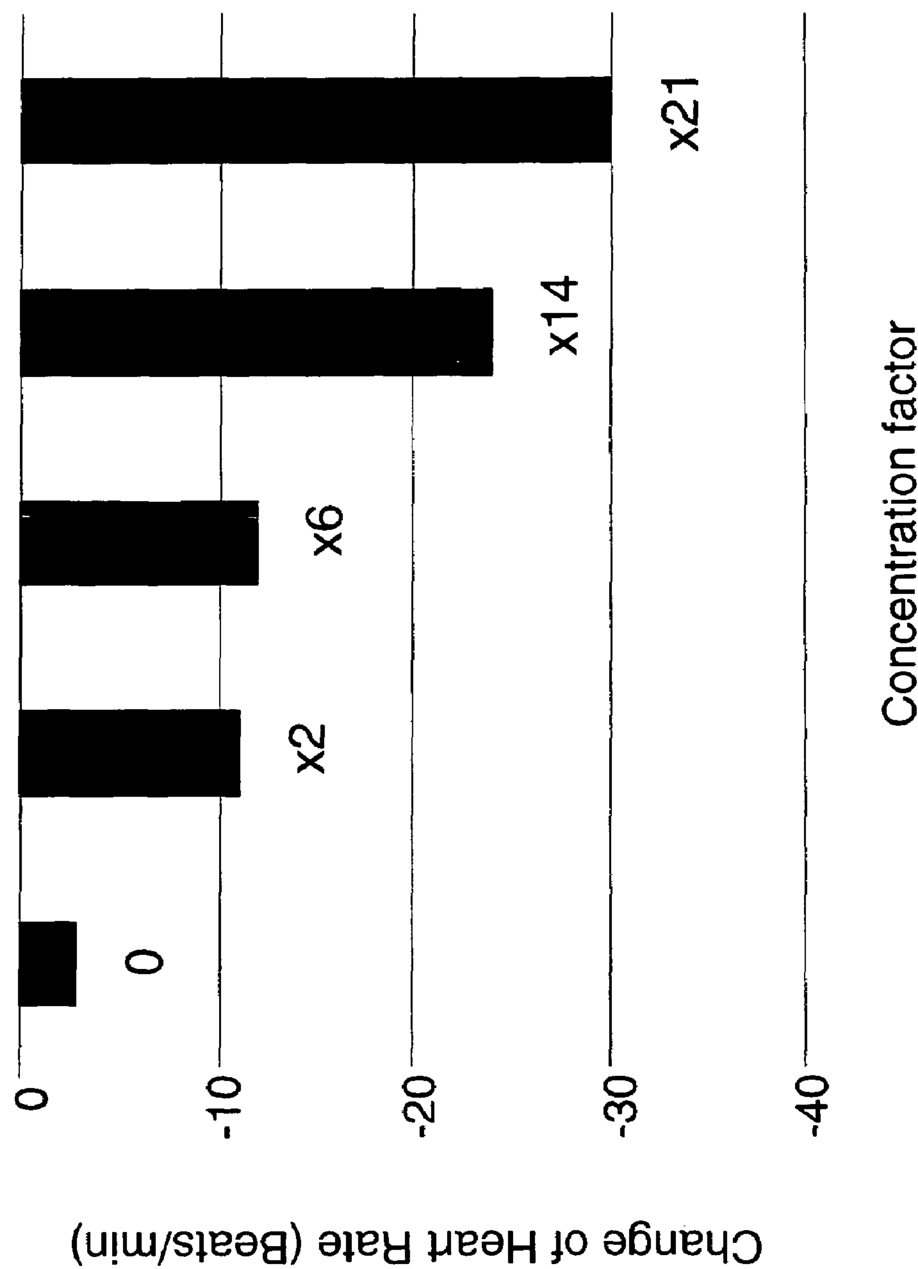

FIG. 2. The reduction in heart rate in animals in the period 12-15 hours after the animals received whey compositions containing solid whey components concentrated 2, 6, 14.3 and 21 times relatively to the amount of solid components in whey obtained after fermentation of milk. The animals was given the whey products by gavage, i.e. feeding by a stomach tube. (O) indicates placebo. The heart rate was determined in animals as described in Example 1 and compared to the heat rate in untreated animals.

EXAMPLES

Example 1

In Vivo Test of Heart Rate Reducing Properties

Materials and Methods

Strains and Cultivation

Strains were streaked on MRS agar and incubated anaerobically for 48 h at 37° C. A single colony was picked, inoculated into MRS broth and grown overnight at 37° C. Stock cultures were prepared from this overnight culture and were stored at −80° C. in 20% glycerol. The strains were precultivated in milk overnight and inoculated 1% (v/v) in fresh milk for the fermentation.

Preparation of the Samples

Whey: Sample 1

The milk (9.5% of protein content) was fermented with the strain of single culture for 16 hours with an inoculation level of 1% (v/v). The fermented product was centrifuged, the pellet was discarded and the whey was filtered through a 0,45 mm filter and freeze-dried. A second fermentation, fermented under the same conditions as the first one, was centrifuged and the whey fraction obtained. The pellet was discarded and the whey was filtered through a 0,45 mm filter and frozen. The whey was used to solubilize the freeze-dried whey powder to concentrate it with a factor 21 before feeding the rats.

Freeze-Dried Fermented Milk Dissolved in Whey: Sample 2

The milk (9.5% of protein content) was fermented with the strain of single culture for 16 hours with an inoculation level of 1% (v/v). The total product was freeze-dried. A second fermentation, with the same conditions as the first one, was centrifuged. The pellet was discarded and the whey was filtered through a 0,45 mm filter and frozen. The whey was used to solubilize the freeze-dried fermented milk powder to concentrate it with a factor 5 before feeding the rats.

Freeze-Dried Fermented Milk Dissolved in Milk: Sample 3

The milk (9.5% of protein content) was fermented with the strain of single culture for 16 hours with an inoculation level of 1% (v/v). The total product was freeze-dried. Milk (9.5% of protein content) was used to solubilize the freeze-dried powder to concentrate it with a factor 5 before feeding the rats.

Overnight Milk Fermentation Product: Sample 4

The milk (9.5% of protein content) was fermented with the strain of single culture for 16 hours with an inoculation level of 1% (v/v).

Overnight Milk Fermentation Product Heat-Treated: Sample 5

The milk (9.5% of protein content) was fermented with the strain of single culture for 16 hours with an inoculation level of 1% (v/v).

Spontaneously Hypertensive Rats

Spontaneously Hypertensive Rats (SHR) was obtained from IFFA CREDO (a Charles River company), Lyon, France.

Each treatment was administered between 9:15$^h$ and 9:30$^h$ by gavage and each animal received a total volume of 2.5 ml per animal.

Experimental Design

Three groups were formed:

Group 1 (n=16): receiving treatment 1 (milk; n=16)

Group 2 (n=12): receiving successive treatments, each administration separated by a 3-day washout period Groups: 1) Placebo (Milk)

2) Sample 1 (Freeze-dried whey suspended in whey. Administered concentrated by factor 21)

2) Sample 2 (freeze-dried fermented milk suspended in whey. administered concentrated by factor 5)

3) Sample 3 (freeze-dried fermented milk suspended in neutral pH milk Administered concentrated by factor 5)

4) Sample 4 (just the fermented milk product)

5) Sample 5 (Fermented milk that was heat treated after fermentation)

6) Sample 6 (milk that had not been fermented but it included the live bacteria).

Prior to the experiments all SHR were acclimated to the animal facilities for 9 weeks. Moreover, all animals were accustomed to gavage and measurement of systolic blood pressure 3 days before the first gavage.

Investigated Parameters

Systolic blood pressure and heart rate were determined for 24 hours after gavage by telemetry (Data Sciences Int.) in conscious SHR at different time points.

In brief, the mean (over a 1 minute period) of systolic, diastolic blood pressures and heart rate were recorded every 15 minutes, during the 24 hours before administration and the 48 hours after administration.

From these tracings, 24 hours mean of systolic and diastolic blood pressures as well as heart rate were calculated in each group.

Furthermore, the variations in systolic and diastolic blood pressures induced by each substance compared to the untreated values were calculated throughout the 24 hours following gavage, and during the 3 to 6, the 12 to 15 and the 21 to 24 hours periods of time after gavage.

Statistics

All results are expressed as mean±standard error of mean. Differences between the untreated value and the value obtained after gavage of each substance were evaluated using a paired student's t-test, where the calculation was done by using the program SISTAT 8.0.

Results

In table 1 is shown the variation of the heart rate determined.

Table 1:

TABLE 1

Heart rate (neats/min) after gavage.

| Group | Period | | | | Variation vs. Untreated | | | |
|---|---|---|---|---|---|---|---|---|
| | 0-24 | 3-6 | 12-15 | 21-24 | 0-24 | 3-6 | 12-15 | 21-24 |
| Untreated[1] | 320 ± 1 | 291 ± 1 | 343 ± 1 | 319 ± 1 | | | | |
| Sample 1 | 297 ± 2* | 268 ± 2* | 326 ± 8 | 294 ± 3* | −26.4 ± 3.4 | −26.4 ± 5.5 | −19.8 ± 9.3 | −29.7 ± 3.6 |
| Untreated[2] | 330 ± 4 | 291 ± 6 | 361 ± 5 | 289 ± 5 | | | | |
| Sample 2 | 307 ± 6* | 282 ± 6 | 333 ± 11* | 265 ± 4* | −21 ± 3 | −9 ± 5 | −27 ± 8 | −24 ± 4 |
| Sample 3 | 312 ± 6* | 272 ± 8* | 344 ± 5* | 272 ± 5* | −16 ± 1 | −19 ± 5 | −17 ± 4 | −18 ± 4 |
| Sample 4 | 318 ± 6 | 297 ± 6 | 335 ± 6 | 279 ± 7 | −10 ± 3 | 7 ± 6 | −26 ± 4 | −10 ± 6 |
| Sample 5 | 313 ± 5* | 290 ± 6 | 337 ± 6* | 280 ± 5 | −15 ± 4 | −1 ± 7 | −23 ± 5 | −9 ± 4 |
| Sample 6 | 343 ± 9 | 330 ± 17 | 359 ± 9 | 305 ± 5* | 14 ± 9 | 38 ± 17 | −2 ± 7 | 16 ± 17 |

*: $p < 0.05$ vs. Untreated

Untreated[1] and untreated[2] are the controls of study 1 and study number 2, respectively. Untreated 1 was the placebo for the sample 1 and untreated 2 was the placebo for all the other samples. We had two placebos because the studies were done independently in two different in vivo studies.

The results demonstrate that the whey product concentrated by a factor 21 (sample 1) has the strongest heart rate reducing properties.

The results demonstrate also that there is no need to up-concentrate the fermented milk product to have already a significant heart rate reducer effect. Samples 4 and 5 are fermented milk products fermented overnight and they have a heart rate reducing effects. However, the heart rate reducer effect is proportional to the concentration factor of the product.

Obviously, the whey part of the product that contains the peptides or other active components is determinant in the heart rate reducer effect. One does observe a dose-heart rate reducing effect of the product.

Sample 3 is freeze-dried fermented milk suspended in neutral pH milk. It reduces the heart rate significantly. This demonstrates the wide application of a fermented product as described herein since it may be dissolved in different liquids to get a required final appropriate use. Characteristic such as different pH are not affecting the heart rate reducer activity of the product.

Sample 5 with heat treatment after fermentation reduces also the heart rate. Substantially all bacteria are killed in this sample. Accordingly, this demonstrates that there is no need to have live bacteria in the final product.

Sample 6 has not been fermented but it includes the live bacteria. It does not reduce the heart rate. It demonstrates that the fermentation step is required.

Example 2

PCR Amplification Reaction

Template DNA was obtained by phenol-chloroform extraction as previously described (Marmur (1961, *Journal of Molecular Biology,* 3, 208-218). The final preparation was genomic template DNA in a TE buffer+RNAse.

The PCR reaction was prepared as follows:

(i) 1.0 µl of template DNA
 1.0 µl of forward primer (5 pmol/µl)
 1.0 µl of reverse primer (5 pmol/µl)
 1.0 µl 2.5 mM dNTD (mixture of dATP, dCTP, dGTP, dTTP)
 5.0 µl Mg buffer (20 mM MgSO4)
 0.5 µl DNA polymerase (Pwo, 100 U)
 10.5 µl $H_2O$ (ii) The thermal program for the PCR amplification was 30 cycles of 1 min at 94° C., 90 s at 50° C. (when primers Tm was around 55° C.), 90 s at 55° C. (when primers Tm was around 62° C.), 90 s at 45° C. (when primers Tm was around 50° C.) and 1 min at 72° C. The samples were cooled to 4° C. after the 30 cycles were completed.

(iii) The PCR products were run on a 1.5% agarose gel at 60 V, excised from the gel under UV light and purified using a QIAquick Gel Extraction Kit according to the manufacturer's instructions (Qiagen, Cat. No. 28704).

Example 3

Proteolytic (ACE) Activity Assay

Preparation of Stock Culture

*Lactobacillus* species were streaked on MRS agar and incubated anaerobically for 48 h at 37° C. A single colony was picked, inoculated into MRS broth and grown overnight at 37° C. *Lactococcus* species were streaked on M17 agar and incubated aerobically for 48 h at 30° C. A single colony was picked, inoculated into M17 broth and grown overnight at 30° C. Stock cultures were prepared from these overnight cultures and were stored at −80° C. in 20% glycerol.

Preparation of Fermented Milk and Extraction of Peptides or Other Active Components Fermentation is performed by inoculate 200 ml of fresh milk with an overnight stock culture of example 1 (1% v/v) and maintain overnight at 37° C. or 30° C. dependent on the strain used.

From the fermented milk, extraction of the peptides or other active components may be achieved by using the following protocol:

- Centrifuge at 3000 g for 10 min at room temperature.
- Withdraw the supernatant and adjust to pH 8.3 (optimal pH for ACE activity test) with NaOH.
- Centrifuge the obtained supernatant at 3000 g for 10 min at room temperature.
- Withdraw the supernatant (whey), which comprises the peptides or other active components.
- Determine the concentration of peptides in the whey by the Lowry test (mg peptide/ml whey) (Lowry et al, 1951. *J. Biol. Chem.,* 193:265-275).

The whey may be used directly for ACE assay or freeze at −20° C. The whey comprising the peptides or other active components is termed "peptide solution" in example 3.

ACE Activity Assay

The peptide pools of milk fermented are tested for ACE activity in vitro. The DL50 (mg/ml) is the peptidic concentration, which inhibits 50% of ACE activity. The lower this value is, the better the anti-hypertensive effect of the fermented milk. The ACE activity of the extracted peptides or other active components is measured by the following protocol:

The essence of the assay is that ACE degrades a hippuryl-L-histidyl-L-leucine (HHL) substrate and adding a color agent develops a color. If peptides or other active components are present the peptides or other active components inhibit ACE and less HHL substrate is degraded. This means less color is developed after addition of the color agent.

Solution Preparation:

Incubation buffer: 188 mmol/l boric acid pH 8.3, 1.375 mmol/l potassium chloride.

(Dissolve 2.91 g of boric acid and 25.63 g potassium chloride in 200 ml of distilled water. Adjust the pH to 8.3 with 1 mol/l potassium hydroxide and dilute to 250 ml with distilled water. Store at room temperature).

Substrate solution: 5.8 mmol/l hippuryl-L-histidyl-L-leucine (HHL).

(Dissolve 250 mg hippuryl-L-histidyl-L-leucine in about 90 ml incubation buffer and fill up to 100 ml with the same buffer. Store at 40° C. The substrate solution can be used for at least 2 weeks).

Stop solution: 100 mmol/l HEPES pH 9, 2.5 mmol EDTA.

(Dissolve 23.83 g HEPES and 0.93 g EDTA in 800 ml distilled water. Adjust to pH 9 with 1 mol/l sodium hydroxide and dilute to 11 with distilled water. Store at room temperature).

Color reagent: 136 mmol/I cyanuric chloride in 1,4-dioxane.

(Dissolve 12.50 g cyanuric chloride in about 400 ml of 1,4-dioxane and fill up with 1, 4-dioxane to 500 ml. Store at room temperature in dark-brown glass bottle).

Assay: (all solutions are equilibrated to room temperature)

- Make a dilution series of the peptide solution with incubation buffer. The series consist of 6 dilutions going from the undiluted peptide solution to a blank (only incubation buffer)
- For each of the dilutions, place 10 μl of peptide solution, 40 μl of substrate (HHL) solution (2.5 μl) and 2.5 μl of ACE (0.25 Units/ml) in a glass tube.
- The positive control comprises 2.5 μl ACE, 10 μl of incubation and 40 μl of substrate (HHL)
- The negative control comprises 12 μl of incubation buffer and 40 μl of substrate (HHL)
- Incubate at 37° C. for 1 hour.
- Stop the reaction by adding 300 μl of stop solution, followed by 150 μl of color reagent—Mix vigorously.
- Allow to stand for 5 minutes and centrifuge at 3300 g for 30 min at room temperature to remove denatured protein and excess cyanuric chloride.
- Transfer 300 μl of supernatant of each sample to microtiter plate hole.
- Read at 405 nm against water as a blank.

The ACE inhibition percentage is expressed by the formula:

$$ACE\ \text{inhibition activity} = \frac{OD405\ \text{nm positive control} - OD405\ \text{nm sample}}{OD405\ \text{nm positive control} - OD405\ \text{nm negative control}}$$

Each dilution has its own ACE inhibition percentage value that gives a curve expressing the ACE inhibition percentage in function of the peptide concentration of the whey. DL50 (peptidic concentration that inhibits 50% of ACE activity) is obtained by reading the peptidic concentration at the intersection point between the curve and the corresponding 50% ACE inhibition point on the axe.

Example 4

Dose-response Experiment

To further substantiate the results presented in Example 1, a dose response experiment was performed by administering compositions containing variable amounts of freeze-dried whey obtained from fermented milk suspended in whey from fermented milk to Spontaneously Hypertensive Rats (SHR).

In general, materials and methods and experimental design were as described in Example 1.

In brief, milk was fermented with *Lactobacillus helveticus* strain CHCC5951 (DSM 14998) for 16 hours with an inoculation level of 1% (v/v). The fermented milk was centrifuged, the pellet discarded and the whey freeze-dried. A second fermentation with the same conditions as the first one was centrifuged. The pellet was discarded and the whey was placed at 4° C. The whey was used to solubilize the freeze-dried whey powder resulting in compositions containing solid whey components concentrated 2, 6 and 14.3 times relatively to the amount of solid components in whey obtained in the second fermentation. The final step of the solubilization was done shortly before feeding the composition to the rats.

As in Example 1, unfermented milk was used as placebo.

Starting with the lowest concentration the doses were tested on the same experimental animals in three separate testing-periods. Each testing-period was separated by a "wash out" period of three days in which animals did not received fermented whey product in order to eliminate the activity of the previous dose.

The result is shown in tabular form in table 2.

TABLE 2

| | Heart rate (beats/min) after gavage. | | | | | | | |
|---|---|---|---|---|---|---|---|---|
| | Period | | | | Variation relative to Placebo | | | |
| | 0-24 | 3-6 | 12-15 | 21-24 | 0-24 | 3-6 | 12-15 | 21-24 |
| Untreated | 306 ± 2 | 265 ± 5 | 337 ± 5 | 273 ± 2 | | | | |
| Placebo | 304 ± 2 | 268 ± 2 | 333 ± 3 | 278 ± 4 | −2 | +3 | −4 | +5 |
| Placebo | 314 ± 11 | 282 ± 12 | 335 ± 12 | 295 ± 14 | | | | |
| Concentration 1 | 302 ± 7 | 278 ± 10 | 324 ± 7 | 274 ± 7 | −12 | −4 | −11 | −21 |
| Placebo | 314 ± 9 | 278 ± 8 | 346 ± 9 | 288 ± 8 | | | | |
| Concentration 2 | 309 ± 9 | 287 ± 10 | 334 ± 9 | 289 ± 11 | −5 | +8 | −12 | 1 |
| Placebo | 311 ± 9 | 278 ± 9 | 337 ± 11 | 279 ± 8 | | | | |
| Concentration 3 | 297 ± 9 | 279 ± 15 | 314 ± 7 | 277 ± 10 | −14 | +1 | −24 | −2 |

Note to Table: Untreated rats were not receiving neither milk nor whey product. Placebo is non-fermented milk. Concentration 1, 2 and 3 are whey compositions containing solid whey components concentrated 2, 6 and 14.3 times, respectively. Note that the activity period of the animals is coincident with the period without light, i.e. the time period from 9 to 21.

In FIG. 1 the results for one full period of concentration 3 (×14.3 concentrated) is shown.

In addition freeze-dried whey powder resulting in compositions containing solid whey components concentrated 21 times relatively to the amount of solid components in whey obtained in the second fermentation. The results of feeding animals with a 2, 6, 14.3 as well as a 21 times concentrated whey product are shown in FIG. 2.

The results show a clear dosage dependent effect on the heart rate of the whey products concentrated up to a factor of 21 times. The higher dose of whey products the larger the decrease of heart rate. It appears that a stationary or asymptotic level not was reached, indicating that compositions containing higher concentrations of the active compound(s) can be expected to have higher efficacy for lowering heart rate.

Example 5

Fluctuations in Heart Rate During Period of High Activity is Reduced

During the activity period of the animals the heart rate increase. The activity period of the animals of this investigation is almost coincident with the period without light, i.e. the period indicated by the black bar (see FIG. 1). However, judged from the observations presented in FIG. 1 it appears that not only the heart rate but, surprisingly, also the fluctuations in heart rate is larger in untreated animals compared to animals treated with the 14.3 times concentrated fermented whey product.

To quantify the fluctuations in heart rate the variance of the heart rate values observed in the time period between 12 and 15 h was estimated. The standard deviation was estimated for both treated as well as untreated animals by use of the SISTAT 8.0 program as described in Example 1, and used to calculate the variance ((standard deviation)$^2$=Variance).

The standard deviation for the treated animals was estimated to 5.9, corresponding to a variance of $(5.9)^2$=34.8.

The standard deviation for the untreated animals was estimated to 10.4, corresponding to a variance of $(10.4)^2$=108.2.

Assuming that the primary data are normally distributed a variance of 34.8 is statistically significantly different from a variance of 108.2 at the 95% level.

Thus, it is possible to conclude that the fluctuations in the heart rate during the activity period (measured as variance) are significantly larger in untreated animals compared to the fluctuations in the heart rate of animals treated with the x14.3 concentrated fermented whey product.

In conclusion, the heart rate fluctuations is stabilized by the whey product fermented with *Lactobacillus helveticus* strain CHCC5951 (DSM 14998). This may be an important feature of the product since it has been observed that changes in heart rate correlated well with mortality in an experimental rabbit model (Zaza et al 2001) and since in particular in stressed situations significant heart rate fluctuations are frequently observed.

Example 6

Comparison of Milk Products Fermented with *L. helveticus* Strain CHCC5951 with a Similar Commercial Product Fermented with a Different Strain.

The purpose of this example was to compare a commercial lactic acid bacterium fermented milk product that is claimed to have blood pressure reducing properties with the product fermented with *Lactobacillus helveticus* strain CHCC5951 (DSM 14998).

The effect on blood pressure and heart rat of the two products was evaluated by administering the two compositions to Wistar rats and measuring the systolic blood pressure, the diastolic blood pressure and the heart rate on anaesthetized animals.

If not specifically mentioned, materials and methods were as described in Example 1.

In brief, milk was fermented with *Lactobacillus helveticus* strain CHCC5951 (DSM 14998) for 16 hours with an inoculation level of 1% (v/v), and the resulting product was freeze-dried to obtain a freeze dried milk powder. A second fermentation, with the same conditions as the first one, was performed and centrifuged. The pellet was discarded and the whey was filtered through a 0.45 μm filter and frozen. Shortly before feeding it to the rats the freeze-dried milk powder was dissolved in the whey. The amount of powder dissolved corresponded to the amount obtained from a volume of fermented milk that was 5 times the volume of the whey it was dissolved in (in casu 4.28 g powder in 30 ml of whey). This composition we refer to as a x5 concentration in this example. The composition was administered to overnight fastened normotensive Wistar rats (300-320 grams) between 09:15 h and 09:30 h by gavage at a dose of 7.5 ml per kg of the x5 composition. The effect of the composition was evaluated between 14:30 h and 16:30 h, i.e. 5-7 hours after the oral administration by measuring the values of arterial blood pressure and heart rate on anaesthetized animals.

The results obtained are shown in table 3.

TABLE 3

Effect of two different fermented products on blood pressure and heart rate.

| | Untreated | Commercial product | CHCC5951 fermented milk product |
|---|---|---|---|
| Systolic blood pressure (mm Hg) | 134 ± 3 | 125 ± 3* | 125 ± 3* |
| Diastolic blood pressure (mm Hg) | 107 ± 3 | 98 ± 4* | 94 ± 2* |
| Mean blood pressure (mm Hg) | 116 ± 3 | 107 ± 4* | 106 ± 2* |
| Heart rate (Beats.min-1) | 390 ± 7 | 387 ± 6 | 353 ± 6* |

Values (mean ± SEM) of systolic, diastolic, mean arterial blood pressure and heart rate in the three different groups, 5-7 hours after gavage.
*indicates a significant difference at the $p < 0.05$ level between treated vs. untreated rats.
The statistical analysis was performed using ANOVA, followed by a Tukey test for multiple comparisons.

From the data it can be concluded that the commercial product and the CHCC5951 fermented product both reduce blood pressure, and furthermore do so to the same extent. However, surprisingly the data in table 3 shows that only the CHCC5951 fermented products significantly reduce the heart rate.

REFERENCES

EP821968 (Calpis Food Industry)

EP1016709 (Calpis Food Industry)

WO0132836 (Valio Ltd.).

Yamamoto et al. (1996) Am. J. Clin. Nurt., 64:767-71.

WO0185984 (Davisco International Foods, Inc.)

Fuglsang, A.; et al. (2002) Applied and Environmental Microbiology, 3566-3569.

Zaza, A., T. Opthof, J. Camm, F. Lombardi and S. Hohnloser (2001) “Heart rate reduction: optimism with some caveats”. nEwSCast Report presented to the XXIIIth Congress of the European Society of Cardiology, Stockholm 2001.

The invention claimed is:

1. A method for reducing the heart rate of a mammal in need thereof comprising administering to the mammal a heart rate reducing effective amount of a composition containing a fermentation product having ACE inhibitory activity that is obtained through the fermentation of animal milk by a lactic acid bacterium which is *Lactobacillus helveticus* strain CHCC5951 (DSMZ 14998), and wherein the amount administered is sufficient to reduce the heart rate in a mammal in need thereof by at least 20%.

2. The method of claim 1, wherein the fermentation product produced by said fermentation comprises peptides with heart rate reducing properties.

3. The method of claim 1, wherein the food material that is fermented comprises one or more animal milk proteins.

4. The method of claim 1, wherein the animal milk protein includes casein.

5. The method of claim 1, wherein said administered composition is a food or feed product.

6. The method of claim 1, wherein said administered composition is a food additive.

7. The method of claim 1, wherein said administered composition is a functional food.

8. The method of claim 1, wherein said administered composition is a component of a medicament.

9. The method of claim 8, wherein the administered composition is a purified or concentrated composition.

10. The method of claim 1 wherein the composition is administered as a therapeutic composition for the treatment of a condition associated with heart rate fluctuations in order to reduce said heart rate fluctuations.

11. The method of claim 10, wherein the composition is administered as a therapeutic composition for the treatment of a coronary artery disease.

12. The method of claim 11, wherein said coronary artery disease associated with heart rate fluctuations is hypertension.

13. The method of claim 1, wherein the mammal is a human subject.

14. The method of claim 1, wherein said fermentation product is purified or concentrated prior to it being incorporated in said administered composition, the purification or concentration comprising:

(a) isolating the composition resulting from the fermentation process;

(b) further purifying or concentrating the composition resulting from the fermentation process; and (c) packaging the resulting purified or concentrated composition for administration to the mammal.

15. The method of claim 14, wherein the purifying or concentrating of the fermentation product is accomplished by centrifugation.

16. The method of claim 15, wherein a supernatant comprising peptides is recovered.

17. The method of claim 14, wherein the purified or concentrated fermentation product comprises whey.

18. The method of claim 1, wherein the administered composition has a heart rate reducing effect that is at least 10% greater than a placebo effect.

19. The method of claim 1, wherein the administered composition has a heart rate reducing effect that is at least 25% greater than a placebo effect.

* * * * *

SEQUENCE LISTING

```
<160> NUMBER OF SEQ ID NOS: 18

<210> SEQ ID NO 1
<211> LENGTH: 5550
<212> TYPE: DNA
<213> ORGANISM: Lactobacillus helveticus
<220> FEATURE:
<221> NAME/KEY: CDS
<222> LOCATION: (1)..(5550)
<223> OTHER INFORMATION:
<300> PUBLICATION INFORMATION:
<308> DATABASE ACCESSION NUMBER: GeneBank/A133727
<309> DATABASE ENTRY DATE: 1999-08-23
<313> RELEVANT RESIDUES: (1)..(5550)

<400> SEQUENCE: 1

atg agg aga aac aaa tat gca ggc tta tta gtt tgt gcc act act cta       48
Met Arg Arg Asn Lys Tyr Ala Gly Leu Leu Val Cys Ala Thr Thr Leu
1               5                   10                  15

tcc gtc gta tct gtg ttc tct act gcc gaa caa caa gtt aag gct agt       96
Ser Val Val Ser Val Phe Ser Thr Ala Glu Gln Gln Val Lys Ala Ser
            20                  25                  30

gtt gac agc caa aca aaa act gtt gaa aaa agt act aaa gca gca gaa      144
Val Asp Ser Gln Thr Lys Thr Val Glu Lys Ser Thr Lys Ala Ala Glu
        35                  40                  45

tct act aca gca aat tta act aac aaa gca gtt gaa gcg caa tta gcc      192
Ser Thr Thr Ala Asn Leu Thr Asn Lys Ala Val Glu Ala Gln Leu Ala
    50                  55                  60

gca aaa ggt gtt aat ttt aaa cac tta act gtt aat caa aaa caa gat      240
Ala Lys Gly Val Asn Phe Lys His Leu Thr Val Asn Gln Lys Gln Asp
65                  70                  75                  80

gta tat gtt gat gta att gtt cag tta tcg gct acc cca gct gct act      288
Val Tyr Val Asp Val Ile Val Gln Leu Ser Ala Thr Pro Ala Ala Thr
                85                  90                  95

aat ggc tca gta agt gct aat tca agt agc gca gaa att gaa caa gct      336
Asn Gly Ser Val Ser Ala Asn Ser Ser Ser Ala Glu Ile Glu Gln Ala
```

-continued

```
            100                 105                 110

tct aaa aaa gta att gcc aat caa gct tct att aag gaa aaa gtt aag      384
Ser Lys Lys Val Ile Ala Asn Gln Ala Ser Ile Lys Glu Lys Val Lys
        115                 120                 125

gca att act aac caa gca att ggt aaa agt tat ggt tat gta gtt aac      432
Ala Ile Thr Asn Gln Ala Ile Gly Lys Ser Tyr Gly Tyr Val Val Asn
    130                 135                 140

gga ttt gca acc aaa gca aaa gta aag gat att caa aaa cta aga aat      480
Gly Phe Ala Thr Lys Ala Lys Val Lys Asp Ile Gln Lys Leu Arg Asn
145                 150                 155                 160

atc cct ggg gtt aaa tca gta act tta gct aaa gtt tat tac gca aat      528
Ile Pro Gly Val Lys Ser Val Thr Leu Ala Lys Val Tyr Tyr Ala Asn
                165                 170                 175

gat tct tca gct gac aat atg gct aac gtt tca acc gtt tgg aac aat      576
Asp Ser Ser Ala Asp Asn Met Ala Asn Val Ser Thr Val Trp Asn Asn
            180                 185                 190

tat aaa tac aaa ggg gaa ggt acc gtc gtt tct atc atc gat act ggt      624
Tyr Lys Tyr Lys Gly Glu Gly Thr Val Val Ser Ile Ile Asp Thr Gly
        195                 200                 205

att gat ccc aat cac aaa gat ttg cgc tta agc gat gat tcc aag gtc      672
Ile Asp Pro Asn His Lys Asp Leu Arg Leu Ser Asp Asp Ser Lys Val
    210                 215                 220

aaa tta acc aaa gat aag gtt aat gct ttt act aaa gaa tct ggt tat      720
Lys Leu Thr Lys Asp Lys Val Asn Ala Phe Thr Lys Glu Ser Gly Tyr
225                 230                 235                 240

ggt cgt tac ttt act gat aaa gtg cca tac ggt cac aat tat tca gac      768
Gly Arg Tyr Phe Thr Asp Lys Val Pro Tyr Gly His Asn Tyr Ser Asp
                245                 250                 255

aat aat gat aat att acc gat gat aat cct agc gag caa cat ggt atg      816
Asn Asn Asp Asn Ile Thr Asp Asp Asn Pro Ser Glu Gln His Gly Met
            260                 265                 270

cac gtt gct ggt atc gta gct gcc aat ggt act gcc gat tct gtt aac      864
His Val Ala Gly Ile Val Ala Ala Asn Gly Thr Ala Asp Ser Val Asn
        275                 280                 285

tct gtt gtt ggt gtt gcc cca gaa gct caa tta cta gct atg aag gct      912
Ser Val Val Gly Val Ala Pro Glu Ala Gln Leu Leu Ala Met Lys Ala
    290                 295                 300

ttc tct aat tca gat agt tca gcc tct act gat tct act agc att atc      960
Phe Ser Asn Ser Asp Ser Ser Ala Ser Thr Asp Ser Thr Ser Ile Ile
305                 310                 315                 320

ggt gca atc gat gat tct gcc aag ctt ggg gct gac gtt cta aac atg     1008
Gly Ala Ile Asp Asp Ser Ala Lys Leu Gly Ala Asp Val Leu Asn Met
                325                 330                 335

tca tta ggt tca gtt tct ggt gaa caa act gaa gac gat cca gaa gtt     1056
Ser Leu Gly Ser Val Ser Gly Glu Gln Thr Glu Asp Asp Pro Glu Val
            340                 345                 350

gcc gct gtt gaa cgt gcc act aag aaa ggt act gca gct gta att tct     1104
Ala Ala Val Glu Arg Ala Thr Lys Lys Gly Thr Ala Ala Val Ile Ser
        355                 360                 365

gcc ggt aac tcc ggc act tca aat tca gaa att gaa ggt gtt aat aaa     1152
Ala Gly Asn Ser Gly Thr Ser Asn Ser Glu Ile Glu Gly Val Asn Lys
    370                 375                 380

gct tat tac ggg aat cct gat atg gaa act tta ggt aat cca ggc act     1200
Ala Tyr Tyr Gly Asn Pro Asp Met Glu Thr Leu Gly Asn Pro Gly Thr
385                 390                 395                 400

gca aga agt gca aca act gtt gcc tct gct gaa aac act aag gct act     1248
Ala Arg Ser Ala Thr Thr Val Ala Ser Ala Glu Asn Thr Lys Ala Thr
                405                 410                 415

aca gat gga gta act att aca tct gct gat gga aaa act act atc gca     1296
```

-continued

```
Thr Asp Gly Val Thr Ile Thr Ser Ala Asp Gly Lys Thr Thr Ile Ala
            420                 425                 430

ggt cca gaa gct act cag ctt tca gaa ggt act gac cgt gct ttc ttt      1344
Gly Pro Glu Ala Thr Gln Leu Ser Glu Gly Thr Asp Arg Ala Phe Phe
        435                 440                 445

aat gat aaa aaa ttc tac gtc gta aaa gat aag aat ggc aat tta ggc      1392
Asn Asp Lys Lys Phe Tyr Val Val Lys Asp Lys Asn Gly Asn Leu Gly
    450                 455                 460

aca ggt tct gcc aag caa tat act tct gct gta aaa ggt aaa att gca      1440
Thr Gly Ser Ala Lys Gln Tyr Thr Ser Ala Val Lys Gly Lys Ile Ala
465                 470                 475                 480

att gtc aag cgt ggt gaa ctt act ttc act gat aaa caa aaa tat gcc      1488
Ile Val Lys Arg Gly Glu Leu Thr Phe Thr Asp Lys Gln Lys Tyr Ala
                485                 490                 495

caa gaa gct ggt gcc gct ggt tta atc att gtt aac aac aaa gcc ggc      1536
Gln Glu Ala Gly Ala Ala Gly Leu Ile Ile Val Asn Asn Lys Ala Gly
            500                 505                 510

gat ata act ggc atg tta ctt aac gct ggc ttc cct act gct ggt tta      1584
Asp Ile Thr Gly Met Leu Leu Asn Ala Gly Phe Pro Thr Ala Gly Leu
        515                 520                 525

tca gct aca tca gga gaa aaa tta gta aaa tat gtt gaa gcc cat cct      1632
Ser Ala Thr Ser Gly Glu Lys Leu Val Lys Tyr Val Glu Ala His Pro
    530                 535                 540

gat gaa gca ttg aag gta agt att gtt gtc caa gcc tta aat aat tct      1680
Asp Glu Ala Leu Lys Val Ser Ile Val Val Gln Ala Leu Asn Asn Ser
545                 550                 555                 560

gct cgt caa aca gac tta atg tct gat ttc acc tca tac ggt ccc act      1728
Ala Arg Gln Thr Asp Leu Met Ser Asp Phe Thr Ser Tyr Gly Pro Thr
                565                 570                 575

tct agc ttg gca ttt aag cca gat atc tca gca cca ggt gga cat att      1776
Ser Ser Leu Ala Phe Lys Pro Asp Ile Ser Ala Pro Gly Gly His Ile
            580                 585                 590

tgg tca act caa aat aac aat ggc tat act aac atg tct ggt act tca      1824
Trp Ser Thr Gln Asn Asn Asn Gly Tyr Thr Asn Met Ser Gly Thr Ser
        595                 600                 605

atg gct tct cca ttt att gct ggt acc caa gca ctt gtt agt caa aca      1872
Met Ala Ser Pro Phe Ile Ala Gly Thr Gln Ala Leu Val Ser Gln Thr
    610                 615                 620

atg aac gac aag aat ggt gct ttc tac gca act tat caa aag atg agc      1920
Met Asn Asp Lys Asn Gly Ala Phe Tyr Ala Thr Tyr Gln Lys Met Ser
625                 630                 635                 640

gca gaa gaa aga acg cca ttt att aag act cta gaa atg aat act gca      1968
Ala Glu Glu Arg Thr Pro Phe Ile Lys Thr Leu Glu Met Asn Thr Ala
                645                 650                 655

agt att caa cct gat att agc cat gat aat gtc atc gtt tca cca cgt      2016
Ser Ile Gln Pro Asp Ile Ser His Asp Asn Val Ile Val Ser Pro Arg
            660                 665                 670

aga caa ggt gct gga ttt att aac gct aac gct act atc caa gct tta      2064
Arg Gln Gly Ala Gly Phe Ile Asn Ala Asn Ala Thr Ile Gln Ala Leu
        675                 680                 685

gct aaa aat cct tca act gta gtc agc agc aat ggc tat cct ggt gta      2112
Ala Lys Asn Pro Ser Thr Val Val Ser Ser Asn Gly Tyr Pro Gly Val
    690                 695                 700

gaa ctc aaa agt ttt aaa gat aga act ctt aat ttc caa gtt aaa ttt      2160
Glu Leu Lys Ser Phe Lys Asp Arg Thr Leu Asn Phe Gln Val Lys Phe
705                 710                 715                 720

act aac cgt acc aac aag gcc tta act tat aaa tta gca aac aat ggt      2208
Thr Asn Arg Thr Asn Lys Ala Leu Thr Tyr Lys Leu Ala Asn Asn Gly
                725                 730                 735
```

-continued

```
aaa aat tct gac gtt tac act tct gct act gat agt tct gca gtt tta     2256
Lys Asn Ser Asp Val Tyr Thr Ser Ala Thr Asp Ser Ser Ala Val Leu
            740                 745                 750

tat gat aag aag att gat ggc gca tca gtt aag gct agt ggt gac att     2304
Tyr Asp Lys Lys Ile Asp Gly Ala Ser Val Lys Ala Ser Gly Asp Ile
        755                 760                 765

ttt gtc ccg gca aat tct act aaa gaa cta act tta acc ttg acc tta     2352
Phe Val Pro Ala Asn Ser Thr Lys Glu Leu Thr Leu Thr Leu Thr Leu
    770                 775                 780

cct agt gac ttt aaa gaa aat caa tat gtt gaa ggc ttc tta aca ttt     2400
Pro Ser Asp Phe Lys Glu Asn Gln Tyr Val Glu Gly Phe Leu Thr Phe
785                 790                 795                 800

aat agt tca gat tct tca caa ttg cgt ctt cca tat atg ggc ttc ttt     2448
Asn Ser Ser Asp Ser Ser Gln Leu Arg Leu Pro Tyr Met Gly Phe Phe
                805                 810                 815

ggc gat tgg gca agt tca gat ctt cca atc ttt gct agt ctt aat gat     2496
Gly Asp Trp Ala Ser Ser Asp Leu Pro Ile Phe Ala Ser Leu Asn Asp
            820                 825                 830

cca aat gta ttt cag cct gac aac aat atg ttt ggt aca ttg gta act     2544
Pro Asn Val Phe Gln Pro Asp Asn Asn Met Phe Gly Thr Leu Val Thr
        835                 840                 845

gta ggt aat agt tca gac aat act aat cct ggt tta agc caa gac gcc     2592
Val Gly Asn Ser Ser Asp Asn Thr Asn Pro Gly Leu Ser Gln Asp Ala
    850                 855                 860

tct ggt aac tta agt ttt gat tct tcg aaa ttt gca att tct aat gct     2640
Ser Gly Asn Leu Ser Phe Asp Ser Ser Lys Phe Ala Ile Ser Asn Ala
865                 870                 875                 880

aaa aat gca caa ttt aag tgg ttt aaa cct act tac tac tta tac aga     2688
Lys Asn Ala Gln Phe Lys Trp Phe Lys Pro Thr Tyr Tyr Leu Tyr Arg
                885                 890                 895

aac gca aac aac gtt aaa atc caa att tta gat aag aat ggt aaa gta     2736
Asn Ala Asn Asn Val Lys Ile Gln Ile Leu Asp Lys Asn Gly Lys Val
            900                 905                 910

atc aat act tta gcc tct ttg agt aac gca acc aag act tac tat aac     2784
Ile Asn Thr Leu Ala Ser Leu Ser Asn Ala Thr Lys Thr Tyr Tyr Asn
        915                 920                 925

tct caa gct caa agc tat act tat ttt gac gat gct cct tct tgg gac     2832
Ser Gln Ala Gln Ser Tyr Thr Tyr Phe Asp Asp Ala Pro Ser Trp Asp
    930                 935                 940

ggc aca tac ttc gat caa caa gct aat aaa act gtt aat gct cct gat     2880
Gly Thr Tyr Phe Asp Gln Gln Ala Asn Lys Thr Val Asn Ala Pro Asp
945                 950                 955                 960

gga aac tat acc tac aga att tct gca act atc gat gga act aat act     2928
Gly Asn Tyr Thr Tyr Arg Ile Ser Ala Thr Ile Asp Gly Thr Asn Thr
                965                 970                 975

gaa caa cat tac gat atc cct gtt aaa gtt gac agt gtt gca cct gta     2976
Glu Gln His Tyr Asp Ile Pro Val Lys Val Asp Ser Val Ala Pro Val
            980                 985                 990

gta aag aac ctt aaa tta gaa tca  agc aag gtt gaa gat  gct aaa ggt   3024
Val Lys Asn Leu Lys Leu Glu Ser  Ser Lys Val Glu Asp  Ala Lys Gly
        995                 1000                1005

caa gag  caa aca cgt tac tac  tta tct gca gaa gca  aaa gat gaa     3069
Gln Glu  Gln Thr Arg Tyr Tyr  Leu Ser Ala Glu Ala  Lys Asp Glu
    1010                1015                1020

ctc agt  ggt tta agt gga gac  gca aat gtt tct gtc  aat ggc gtt     3114
Leu Ser  Gly Leu Ser Gly Asp  Ala Asn Val Ser Val  Asn Gly Val
    1025                1030                1035

tca gct  caa tta gaa tac gat  cct act gct aag gct  gat aag gat     3159
Ser Ala  Gln Leu Glu Tyr Asp  Pro Thr Ala Lys Ala  Asp Lys Asp
    1040                1045                1050
```

-continued

```
ggt ttc  caa aaa gtg gaa atc  gat tta tcc cca gct  caa gca aag      3204
Gly Phe  Gln Lys Val Glu Ile  Asp Leu Ser Pro Ala  Gln Ala Lys
    1055                 1060                 1065

gct ctt  caa gca ggt aca aac  acc ttt tct gtt gcc  tta ttc gat      3249
Ala Leu  Gln Ala Gly Thr Asn  Thr Phe Ser Val Ala  Leu Phe Asp
    1070                 1075                 1080

aat gct  gca aat gca ggt aca  gct tca ggt gaa ggc  aat aaa cca      3294
Asn Ala  Ala Asn Ala Gly Thr  Ala Ser Gly Glu Gly  Asn Lys Pro
    1085                 1090                 1095

ggt gaa  act aac ttc ggt tta  gtt ctt aga aac ggt  ggc tta cca      3339
Gly Glu  Thr Asn Phe Gly Leu  Val Leu Arg Asn Gly  Gly Leu Pro
    1100                 1105                 1110

gac aaa  atc tca tct caa act  aag ggc tac gat gcc  aaa aat ggt      3384
Asp Lys  Ile Ser Ser Gln Thr  Lys Gly Tyr Asp Ala  Lys Asn Gly
    1115                 1120                 1125

act tat  gta ttc tct ggt act  tac cca agc aaa ctc  tat gga act      3429
Thr Tyr  Val Phe Ser Gly Thr  Tyr Pro Ser Lys Leu  Tyr Gly Thr
    1130                 1135                 1140

tac act  gat aaa gat ggt caa  acc cat gac tta aat  gta gaa agt      3474
Tyr Thr  Asp Lys Asp Gly Gln  Thr His Asp Leu Asn  Val Glu Ser
    1145                 1150                 1155

gat ggc  aac aag tta ttc gtt  gca aag ctt cca ctt  tct aaa gat      3519
Asp Gly  Asn Lys Leu Phe Val  Ala Lys Leu Pro Leu  Ser Lys Asp
    1160                 1165                 1170

gac tat  aag act act gtt acc  ctt tac gct gat tct  gac cat aag      3564
Asp Tyr  Lys Thr Thr Val Thr  Leu Tyr Ala Asp Ser  Asp His Lys
    1175                 1180                 1185

acc ttg  ctt aag aaa caa gac  att acc gta agc tta  gtc cca gct      3609
Thr Leu  Leu Lys Lys Gln Asp  Ile Thr Val Ser Leu  Val Pro Ala
    1190                 1195                 1200

aag gtc  gaa agt ttg tct gta  gat aag aat gat act  tat gat gag      3654
Lys Val  Glu Ser Leu Ser Val  Asp Lys Asn Asp Thr  Tyr Asp Glu
    1205                 1210                 1215

act aaa  gat tcg tcg gct gca  tta gct caa act tct  gaa aac act      3699
Thr Lys  Asp Ser Ser Ala Ala  Leu Ala Gln Thr Ser  Glu Asn Thr
    1220                 1225                 1230

gta aaa  ctt tct ggt aaa gta  agt ggt gat act aag  act tta gtg      3744
Val Lys  Leu Ser Gly Lys Val  Ser Gly Asp Thr Lys  Thr Leu Val
    1235                 1240                 1245

gtt aaa  caa aaa ggt cag aaa  gac atc tca gtt aaa  ctt aat gct      3789
Val Lys  Gln Lys Gly Gln Lys  Asp Ile Ser Val Lys  Leu Asn Ala
    1250                 1255                 1260

gat cac  aca ttt agt act gaa  ctg cca gta agc ttt  ggt gaa aat      3834
Asp His  Thr Phe Ser Thr Glu  Leu Pro Val Ser Phe  Gly Glu Asn
    1265                 1270                 1275

gac ttt  act att gta gca acc  gac tct aat ggt aat  tca tct agt      3879
Asp Phe  Thr Ile Val Ala Thr  Asp Ser Asn Gly Asn  Ser Ser Ser
    1280                 1285                 1290

gta gaa  caa aaa gtt aaa tct  agt gat cgt ggt aaa  act act gtt      3924
Val Glu  Gln Lys Val Lys Ser  Ser Asp Arg Gly Lys  Thr Thr Val
    1295                 1300                 1305

tca agt  agt gat gtt acc ttc  gat aac ggt atc aag  tgg ggt act      3969
Ser Ser  Ser Asp Val Thr Phe  Asp Asn Gly Ile Lys  Trp Gly Thr
    1310                 1315                 1320

cgt aac  gtt aac ggt att cgt  aac gtt aac gcc aag  act aag aac      4014
Arg Asn  Val Asn Gly Ile Arg  Asn Val Asn Ala Lys  Thr Lys Asn
    1325                 1330                 1335

tac aat  cct aag act ggt gag  tta acc ctt act ggt  aaa gta aaa      4059
Tyr Asn  Pro Lys Thr Gly Glu  Leu Thr Leu Thr Gly  Lys Val Lys
```

-continued

```
    1340                1345                1350

aga cca  act act act ttg caa  att ggc ggt aaa aac  gta aaa att      4104
Arg Pro  Thr Thr Thr Leu Gln  Ile Gly Gly Lys Asn  Val Lys Ile
    1355                1360                1365

aat tca  gat cag aca ttt aaa  gta gta tta aat att  ggt act cat      4149
Asn Ser  Asp Gln Thr Phe Lys  Val Val Leu Asn Ile  Gly Thr His
    1370                1375                1380

ggt gct  aag att ttc cct gcg  ttg atc ggt gat tca  act gtt aga      4194
Gly Ala  Lys Ile Phe Pro Ala  Leu Ile Gly Asp Ser  Thr Val Arg
    1385                1390                1395

gaa act  act caa gaa aga tta  agt ttc tat gta gat  gca gaa gct      4239
Glu Thr  Thr Gln Glu Arg Leu  Ser Phe Tyr Val Asp  Ala Glu Ala
    1400                1405                1410

cct act  ttg aac tta gat agt  gaa aac act gtc tac  acc aac aag      4284
Pro Thr  Leu Asn Leu Asp Ser  Glu Asn Thr Val Tyr  Thr Asn Lys
    1415                1420                1425

gat aag  ttt act atc tca ggc  act ata agt gat gat  tac aag ttc      4329
Asp Lys  Phe Thr Ile Ser Gly  Thr Ile Ser Asp Asp  Tyr Lys Phe
    1430                1435                1440

tac gac  tta tca ata aat ggt  aac gat gtt gaa act  agc tgg agc      4374
Tyr Asp  Leu Ser Ile Asn Gly  Asn Asp Val Glu Thr  Ser Trp Ser
    1445                1450                1455

gcc gta  gac tac cac agc aaa  gaa ggt atc aag aag  aac ttt aag      4419
Ala Val  Asp Tyr His Ser Lys  Glu Gly Ile Lys Lys  Asn Phe Lys
    1460                1465                1470

cat gaa  gtt gac ttg aag aaa  ggt aag aat act ttt  aac gtt aaa      4464
His Glu  Val Asp Leu Lys Lys  Gly Lys Asn Thr Phe  Asn Val Lys
    1475                1480                1485

gta act  gac att cag ggt aac  tca agt tca caa gca  tta gtt gta      4509
Val Thr  Asp Ile Gln Gly Asn  Ser Ser Ser Gln Ala  Leu Val Val
    1490                1495                1500

tac tat  gaa cct gct aag act  tta gct gag cct agt  gta gac aag      4554
Tyr Tyr  Glu Pro Ala Lys Thr  Leu Ala Glu Pro Ser  Val Asp Lys
    1505                1510                1515

ttg tta  aca aag acg gca aat  ttg caa ctt ctt aaa  gct act act      4599
Leu Leu  Thr Lys Thr Ala Asn  Leu Gln Leu Leu Lys  Ala Thr Thr
    1520                1525                1530

gat gaa  tct gaa gct aaa gtt  gtt tac agc ctt gat  aat ggc aag      4644
Asp Glu  Ser Glu Ala Lys Val  Val Tyr Ser Leu Asp  Asn Gly Lys
    1535                1540                1545

aca ttc  aac gat gta cca gct  gat ggt ttc aag gtt  act gaa aac      4689
Thr Phe  Asn Asp Val Pro Ala  Asp Gly Phe Lys Val  Thr Glu Asn
    1550                1555                1560

gga act  gta caa ttt aaa gca  gtt gat aaa tac ggc  aac gaa tcc      4734
Gly Thr  Val Gln Phe Lys Ala  Val Asp Lys Tyr Gly  Asn Glu Ser
    1565                1570                1575

aaa gtc  aag tct gta gaa att  aag gga ctt aac aag  gaa aac caa      4779
Lys Val  Lys Ser Val Glu Ile  Lys Gly Leu Asn Lys  Glu Asn Gln
    1580                1585                1590

cct agc  gaa gat aag gaa tta  gct aag gct aag gaa  aat ctt cag      4824
Pro Ser  Glu Asp Lys Glu Leu  Ala Lys Ala Lys Glu  Asn Leu Gln
    1595                1600                1605

gct aag  gtt gat gcc ggt gaa  aag aag gat ctt gat  aag tac act      4869
Ala Lys  Val Asp Ala Gly Glu  Lys Lys Asp Leu Asp  Lys Tyr Thr
    1610                1615                1620

gct gac  tcc aag aag gac ttc  aat gat gcc ttg aag  aag gct aag      4914
Ala Asp  Ser Lys Lys Asp Phe  Asn Asp Ala Leu Lys  Lys Ala Lys
    1625                1630                1635

gat gtt  tta gct gac aag aat  gct aaa tta gct gac  ctt caa gat      4959
```

-continued

```
Asp Val  Leu Ala Asp Lys Asn  Ala Lys Leu Ala Asp  Leu Gln Asp
    1640                 1645                 1650

gct gct  aag gct ctt gat aag  gca gag caa gct tta  act gaa aag      5004
Ala Ala  Lys Ala Leu Asp Lys  Ala Glu Gln Ala Leu  Thr Glu Lys
    1655                 1660                 1665

cct gct  gaa cca act atc cca  ctg cta caa ggg aac  aat aat gct      5049
Pro Ala  Glu Pro Thr Ile Pro  Leu Leu Gln Gly Asn  Asn Asn Ala
    1670                 1675                 1680

gta tcg  aat att aat act tcc  tct gat aac caa gtt  gca gct cct      5094
Val Ser  Asn Ile Asn Thr Ser  Ser Asp Asn Gln Val  Ala Ala Pro
    1685                 1690                 1695

gtg cat  gct gaa aaa gac acc  aag aat gat aac aag  aat aca aca      5139
Val His  Ala Glu Lys Asp Thr  Lys Asn Asp Asn Lys  Asn Thr Thr
    1700                 1705                 1710

gaa gaa  ggt aag gac act aag  gta atg ttc aag tca  gtt ctt tac      5184
Glu Glu  Gly Lys Asp Thr Lys  Val Met Phe Lys Ser  Val Leu Tyr
    1715                 1720                 1725

act aaa  gac ctt aaa aag aca  agg agc act gcc caa  gcc tac agt      5229
Thr Lys  Asp Leu Lys Lys Thr  Arg Ser Thr Ala Gln  Ala Tyr Ser
    1730                 1735                 1740

tca ctc  aaa ctt gta acc gaa  aaa gga aag ctt aag  gtt tac aca      5274
Ser Leu  Lys Leu Val Thr Glu  Lys Gly Lys Leu Lys  Val Tyr Thr
    1745                 1750                 1755

ttc aaa  ggt cac tac ttc tac  aag gtt gtt gat cgg  aat gca tat      5319
Phe Lys  Gly His Tyr Phe Tyr  Lys Val Val Asp Arg  Asn Ala Tyr
    1760                 1765                 1770

gtt cgt  gta aga aat gtg act  ggt act aag gca acg  tta aag aga      5364
Val Arg  Val Arg Asn Val Thr  Gly Thr Lys Ala Thr  Leu Lys Arg
    1775                 1780                 1785

aat tca  ttt gtc tac caa tca  aat ggt aag aaa gca  tca cgt aaa      5409
Asn Ser  Phe Val Tyr Gln Ser  Asn Gly Lys Lys Ala  Ser Arg Lys
    1790                 1795                 1800

ctt ctc  aag aaa ggt act acc  att acc gtc tac ggc  gat caa tac      5454
Leu Leu  Lys Lys Gly Thr Thr  Ile Thr Val Tyr Gly  Asp Gln Tyr
    1805                 1810                 1815

aaa gct  ctt aag cat tac aag  aag tat gct tac aga  atc ggt gaa      5499
Lys Ala  Leu Lys His Tyr Lys  Lys Tyr Ala Tyr Arg  Ile Gly Glu
    1820                 1825                 1830

ggt aga  tac ata aag agt gtc  aat gtt aac aga gtt  gat ctt gta      5544
Gly Arg  Tyr Ile Lys Ser Val  Asn Val Asn Arg Val  Asp Leu Val
    1835                 1840                 1845

aaa taa                                                             5550
Lys
```

<210> SEQ ID NO 2
<211> LENGTH: 1849
<212> TYPE: PRT
<213> ORGANISM: Lactobacillus helveticus

<400> SEQUENCE: 2

```
Met Arg Arg Asn Lys Tyr Ala Gly Leu Leu Val Cys Ala Thr Thr Leu
1               5                   10                  15

Ser Val Val Ser Val Phe Ser Thr Ala Glu Gln Gln Val Lys Ala Ser
            20                  25                  30

Val Asp Ser Gln Thr Lys Thr Val Glu Lys Ser Thr Lys Ala Ala Glu
        35                  40                  45

Ser Thr Thr Ala Asn Leu Thr Asn Lys Ala Val Glu Ala Gln Leu Ala
    50                  55                  60

Ala Lys Gly Val Asn Phe Lys His Leu Thr Val Asn Gln Lys Gln Asp
```

-continued

```
65                  70                  75                  80

Val Tyr Val Asp Val Ile Val Gln Leu Ser Ala Thr Pro Ala Ala Thr
                85                  90                  95

Asn Gly Ser Val Ser Ala Asn Ser Ser Ser Ala Glu Ile Glu Gln Ala
            100                 105                 110

Ser Lys Lys Val Ile Ala Asn Gln Ala Ser Ile Lys Glu Lys Val Lys
        115                 120                 125

Ala Ile Thr Asn Gln Ala Ile Gly Lys Ser Tyr Gly Tyr Val Val Asn
    130                 135                 140

Gly Phe Ala Thr Lys Ala Lys Val Lys Asp Ile Gln Lys Leu Arg Asn
145                 150                 155                 160

Ile Pro Gly Val Lys Ser Val Thr Leu Ala Lys Val Tyr Tyr Ala Asn
                165                 170                 175

Asp Ser Ser Ala Asp Asn Met Ala Asn Val Ser Thr Val Trp Asn Asn
            180                 185                 190

Tyr Lys Tyr Lys Gly Glu Gly Thr Val Val Ser Ile Ile Asp Thr Gly
        195                 200                 205

Ile Asp Pro Asn His Lys Asp Leu Arg Leu Ser Asp Asp Ser Lys Val
    210                 215                 220

Lys Leu Thr Lys Asp Lys Val Asn Ala Phe Thr Lys Glu Ser Gly Tyr
225                 230                 235                 240

Gly Arg Tyr Phe Thr Asp Lys Val Pro Tyr Gly His Asn Tyr Ser Asp
                245                 250                 255

Asn Asn Asp Asn Ile Thr Asp Asp Asn Pro Ser Glu Gln His Gly Met
            260                 265                 270

His Val Ala Gly Ile Val Ala Ala Asn Gly Thr Ala Asp Ser Val Asn
        275                 280                 285

Ser Val Val Gly Val Ala Pro Glu Ala Gln Leu Leu Ala Met Lys Ala
    290                 295                 300

Phe Ser Asn Ser Asp Ser Ser Ala Ser Thr Asp Ser Thr Ser Ile Ile
305                 310                 315                 320

Gly Ala Ile Asp Asp Ser Ala Lys Leu Gly Ala Asp Val Leu Asn Met
                325                 330                 335

Ser Leu Gly Ser Val Ser Gly Glu Gln Thr Glu Asp Asp Pro Glu Val
            340                 345                 350

Ala Ala Val Glu Arg Ala Thr Lys Lys Gly Thr Ala Ala Val Ile Ser
        355                 360                 365

Ala Gly Asn Ser Gly Thr Ser Asn Ser Glu Ile Glu Gly Val Asn Lys
    370                 375                 380

Ala Tyr Tyr Gly Asn Pro Asp Met Glu Thr Leu Gly Asn Pro Gly Thr
385                 390                 395                 400

Ala Arg Ser Ala Thr Thr Val Ala Ser Ala Glu Asn Thr Lys Ala Thr
                405                 410                 415

Thr Asp Gly Val Thr Ile Thr Ser Ala Asp Gly Lys Thr Thr Ile Ala
            420                 425                 430

Gly Pro Glu Ala Thr Gln Leu Ser Glu Gly Thr Asp Arg Ala Phe Phe
        435                 440                 445

Asn Asp Lys Lys Phe Tyr Val Val Lys Asp Lys Asn Gly Asn Leu Gly
    450                 455                 460

Thr Gly Ser Ala Lys Gln Tyr Thr Ser Ala Val Lys Gly Lys Ile Ala
465                 470                 475                 480

Ile Val Lys Arg Gly Glu Leu Thr Phe Thr Asp Lys Gln Lys Tyr Ala
                485                 490                 495
```

-continued

```
Gln Glu Ala Gly Ala Ala Gly Leu Ile Ile Val Asn Asn Lys Ala Gly
            500                 505                 510

Asp Ile Thr Gly Met Leu Leu Asn Ala Gly Phe Pro Thr Ala Gly Leu
        515                 520                 525

Ser Ala Thr Ser Gly Glu Lys Leu Val Lys Tyr Val Glu Ala His Pro
    530                 535                 540

Asp Glu Ala Leu Lys Val Ser Ile Val Val Gln Ala Leu Asn Asn Ser
545                 550                 555                 560

Ala Arg Gln Thr Asp Leu Met Ser Asp Phe Thr Ser Tyr Gly Pro Thr
                565                 570                 575

Ser Ser Leu Ala Phe Lys Pro Asp Ile Ser Ala Pro Gly Gly His Ile
            580                 585                 590

Trp Ser Thr Gln Asn Asn Asn Gly Tyr Thr Asn Met Ser Gly Thr Ser
        595                 600                 605

Met Ala Ser Pro Phe Ile Ala Gly Thr Gln Ala Leu Val Ser Gln Thr
    610                 615                 620

Met Asn Asp Lys Asn Gly Ala Phe Tyr Ala Thr Tyr Gln Lys Met Ser
625                 630                 635                 640

Ala Glu Glu Arg Thr Pro Phe Ile Lys Thr Leu Glu Met Asn Thr Ala
                645                 650                 655

Ser Ile Gln Pro Asp Ile Ser His Asp Asn Val Ile Val Ser Pro Arg
            660                 665                 670

Arg Gln Gly Ala Gly Phe Ile Asn Ala Asn Ala Thr Ile Gln Ala Leu
        675                 680                 685

Ala Lys Asn Pro Ser Thr Val Val Ser Ser Asn Gly Tyr Pro Gly Val
    690                 695                 700

Glu Leu Lys Ser Phe Lys Asp Arg Thr Leu Asn Phe Gln Val Lys Phe
705                 710                 715                 720

Thr Asn Arg Thr Asn Lys Ala Leu Thr Tyr Lys Leu Ala Asn Asn Gly
                725                 730                 735

Lys Asn Ser Asp Val Tyr Thr Ser Ala Thr Asp Ser Ser Ala Val Leu
            740                 745                 750

Tyr Asp Lys Lys Ile Asp Gly Ala Ser Val Lys Ala Ser Gly Asp Ile
        755                 760                 765

Phe Val Pro Ala Asn Ser Thr Lys Glu Leu Thr Leu Thr Leu Thr Leu
    770                 775                 780

Pro Ser Asp Phe Lys Glu Asn Gln Tyr Val Glu Gly Phe Leu Thr Phe
785                 790                 795                 800

Asn Ser Ser Asp Ser Ser Gln Leu Arg Leu Pro Tyr Met Gly Phe Phe
                805                 810                 815

Gly Asp Trp Ala Ser Ser Asp Leu Pro Ile Phe Ala Ser Leu Asn Asp
            820                 825                 830

Pro Asn Val Phe Gln Pro Asp Asn Asn Met Phe Gly Thr Leu Val Thr
        835                 840                 845

Val Gly Asn Ser Ser Asp Asn Thr Asn Pro Gly Leu Ser Gln Asp Ala
    850                 855                 860

Ser Gly Asn Leu Ser Phe Asp Ser Ser Lys Phe Ala Ile Ser Asn Ala
865                 870                 875                 880

Lys Asn Ala Gln Phe Lys Trp Phe Lys Pro Thr Tyr Tyr Leu Tyr Arg
                885                 890                 895

Asn Ala Asn Asn Val Lys Ile Gln Ile Leu Asp Lys Asn Gly Lys Val
            900                 905                 910
```

-continued

```
Ile Asn Thr Leu Ala Ser Leu Ser Asn Ala Thr Lys Thr Tyr Tyr Asn
        915                 920                 925

Ser Gln Ala Gln Ser Tyr Thr Tyr Phe Asp Asp Ala Pro Ser Trp Asp
    930                 935                 940

Gly Thr Tyr Phe Asp Gln Gln Ala Asn Lys Thr Val Asn Ala Pro Asp
945                 950                 955                 960

Gly Asn Tyr Thr Tyr Arg Ile Ser Ala Thr Ile Asp Gly Thr Asn Thr
                965                 970                 975

Glu Gln His Tyr Asp Ile Pro Val Lys Val Asp Ser Val Ala Pro Val
            980                 985                 990

Val Lys Asn Leu Lys Leu Glu Ser  Ser Lys Val Glu Asp  Ala Lys Gly
        995                 1000                1005

Gln Glu  Gln Thr Arg Tyr Tyr  Leu Ser Ala Glu Ala  Lys Asp Glu
    1010                1015                1020

Leu Ser  Gly Leu Ser Gly Asp  Ala Asn Val Ser Val  Asn Gly Val
    1025                1030                1035

Ser Ala  Gln Leu Glu Tyr Asp  Pro Thr Ala Lys Ala  Asp Lys Asp
    1040                1045                1050

Gly Phe  Gln Lys Val Glu Ile  Asp Leu Ser Pro Ala  Gln Ala Lys
    1055                1060                1065

Ala Leu  Gln Ala Gly Thr Asn  Thr Phe Ser Val Ala  Leu Phe Asp
    1070                1075                1080

Asn Ala  Ala Asn Ala Gly Thr  Ala Ser Gly Glu Gly  Asn Lys Pro
    1085                1090                1095

Gly Glu  Thr Asn Phe Gly Leu  Val Leu Arg Asn Gly  Gly Leu Pro
    1100                1105                1110

Asp Lys  Ile Ser Ser Gln Thr  Lys Gly Tyr Asp Ala  Lys Asn Gly
    1115                1120                1125

Thr Tyr  Val Phe Ser Gly Thr  Tyr Pro Ser Lys Leu  Tyr Gly Thr
    1130                1135                1140

Tyr Thr  Asp Lys Asp Gly Gln  Thr His Asp Leu Asn  Val Glu Ser
    1145                1150                1155

Asp Gly  Asn Lys Leu Phe Val  Ala Lys Leu Pro Leu  Ser Lys Asp
    1160                1165                1170

Asp Tyr  Lys Thr Thr Val Thr  Leu Tyr Ala Asp Ser  Asp His Lys
    1175                1180                1185

Thr Leu  Leu Lys Lys Gln Asp  Ile Thr Val Ser Leu  Val Pro Ala
    1190                1195                1200

Lys Val  Glu Ser Leu Ser Val  Asp Lys Asn Asp Thr  Tyr Asp Glu
    1205                1210                1215

Thr Lys  Asp Ser Ser Ala Ala  Leu Ala Gln Thr Ser  Glu Asn Thr
    1220                1225                1230

Val Lys  Leu Ser Gly Lys Val  Ser Gly Asp Thr Lys  Thr Leu Val
    1235                1240                1245

Val Lys  Gln Lys Gly Gln Lys  Asp Ile Ser Val Lys  Leu Asn Ala
    1250                1255                1260

Asp His  Thr Phe Ser Thr Glu  Leu Pro Val Ser Phe  Gly Glu Asn
    1265                1270                1275

Asp Phe  Thr Ile Val Ala Thr  Asp Ser Asn Gly Asn  Ser Ser Ser
    1280                1285                1290

Val Glu  Gln Lys Val Lys Ser  Ser Asp Arg Gly Lys  Thr Thr Val
    1295                1300                1305

Ser Ser  Ser Asp Val Thr Phe  Asp Asn Gly Ile Lys  Trp Gly Thr
```

-continued

```
    1310                1315                1320

Arg Asn  Val Asn Gly Ile Arg  Asn Val Asn Ala Lys  Thr Lys Asn
    1325                1330                1335

Tyr Asn  Pro Lys Thr Gly Glu  Leu Thr Leu Thr Gly  Lys Val Lys
    1340                1345                1350

Arg Pro  Thr Thr Thr Leu Gln  Ile Gly Gly Lys Asn  Val Lys Ile
    1355                1360                1365

Asn Ser  Asp Gln Thr Phe Lys  Val Val Leu Asn Ile  Gly Thr His
    1370                1375                1380

Gly Ala  Lys Ile Phe Pro Ala  Leu Ile Gly Asp Ser  Thr Val Arg
    1385                1390                1395

Glu Thr  Thr Gln Glu Arg Leu  Ser Phe Tyr Val Asp  Ala Glu Ala
    1400                1405                1410

Pro Thr  Leu Asn Leu Asp Ser  Glu Asn Thr Val Tyr  Thr Asn Lys
    1415                1420                1425

Asp Lys  Phe Thr Ile Ser Gly  Thr Ile Ser Asp Asp  Tyr Lys Phe
    1430                1435                1440

Tyr Asp  Leu Ser Ile Asn Gly  Asn Asp Val Glu Thr  Ser Trp Ser
    1445                1450                1455

Ala Val  Asp Tyr His Ser Lys  Glu Gly Ile Lys Lys  Asn Phe Lys
    1460                1465                1470

His Glu  Val Asp Leu Lys Lys  Gly Lys Asn Thr Phe  Asn Val Lys
    1475                1480                1485

Val Thr  Asp Ile Gln Gly Asn  Ser Ser Ser Gln Ala  Leu Val Val
    1490                1495                1500

Tyr Tyr  Glu Pro Ala Lys Thr  Leu Ala Glu Pro Ser  Val Asp Lys
    1505                1510                1515

Leu Leu  Thr Lys Thr Ala Asn  Leu Gln Leu Leu Lys  Ala Thr Thr
    1520                1525                1530

Asp Glu  Ser Glu Ala Lys Val  Val Tyr Ser Leu Asp  Asn Gly Lys
    1535                1540                1545

Thr Phe  Asn Asp Val Pro Ala  Asp Gly Phe Lys Val  Thr Glu Asn
    1550                1555                1560

Gly Thr  Val Gln Phe Lys Ala  Val Asp Lys Tyr Gly  Asn Glu Ser
    1565                1570                1575

Lys Val  Lys Ser Val Glu Ile  Lys Gly Leu Asn Lys  Glu Asn Gln
    1580                1585                1590

Pro Ser  Glu Asp Lys Glu Leu  Ala Lys Ala Lys Glu  Asn Leu Gln
    1595                1600                1605

Ala Lys  Val Asp Ala Gly Glu  Lys Lys Asp Leu Asp  Lys Tyr Thr
    1610                1615                1620

Ala Asp  Ser Lys Lys Asp Phe  Asn Asp Ala Leu Lys  Lys Ala Lys
    1625                1630                1635

Asp Val  Leu Ala Asp Lys Asn  Ala Lys Leu Ala Asp  Leu Gln Asp
    1640                1645                1650

Ala Ala  Lys Ala Leu Asp Lys  Ala Glu Gln Ala Leu  Thr Glu Lys
    1655                1660                1665

Pro Ala  Glu Pro Thr Ile Pro  Leu Leu Gln Gly Asn  Asn Asn Ala
    1670                1675                1680

Val Ser  Asn Ile Asn Thr Ser  Ser Asp Asn Gln Val  Ala Ala Pro
    1685                1690                1695

Val His  Ala Glu Lys Asp Thr  Lys Asn Asp Asn Lys  Asn Thr Thr
    1700                1705                1710
```

-continued

```
Glu Glu  Gly Lys Asp Thr Lys  Val Met Phe Lys Ser  Val Leu Tyr
    1715                1720                1725

Thr Lys  Asp Leu Lys Lys Thr  Arg Ser Thr Ala Gln  Ala Tyr Ser
    1730                1735                1740

Ser Leu  Lys Leu Val Thr Glu  Lys Gly Lys Leu Lys  Val Tyr Thr
    1745                1750                1755

Phe Lys  Gly His Tyr Phe Tyr  Lys Val Val Asp Arg  Asn Ala Tyr
    1760                1765                1770

Val Arg  Val Arg Asn Val Thr  Gly Thr Lys Ala Thr  Leu Lys Arg
    1775                1780                1785

Asn Ser  Phe Val Tyr Gln Ser  Asn Gly Lys Lys Ala  Ser Arg Lys
    1790                1795                1800

Leu Leu  Lys Lys Gly Thr Thr  Ile Thr Val Tyr Gly  Asp Gln Tyr
    1805                1810                1815

Lys Ala  Leu Lys His Tyr Lys  Lys Tyr Ala Tyr Arg  Ile Gly Glu
    1820                1825                1830

Gly Arg  Tyr Ile Lys Ser Val  Asn Val Asn Arg Val  Asp Leu Val
    1835                1840                1845

Lys
```

```
<210> SEQ ID NO 3
<211> LENGTH: 2679
<212> TYPE: DNA
<213> ORGANISM: Lactobacillus helveticus
<220> FEATURE:
<221> NAME/KEY: CDS
<222> LOCATION: (1)..(2679)
<223> OTHER INFORMATION:

<400> SEQUENCE: 3

atg ata aga cta ctg gga aga tgg ttg tgc tcc aga tgg tca ata cac       48
Met Ile Arg Leu Leu Gly Arg Trp Leu Cys Ser Arg Trp Ser Ile His
1               5                   10                  15

tta ccg ctt tgt tgc ccc ttg tac aac aat ggt gaa aac aaa gtt caa       96
Leu Pro Leu Cys Cys Pro Leu Tyr Asn Asn Gly Glu Asn Lys Val Gln
            20                  25                  30

act aat gac act cca gtt atc att gat act act gct cct gtt ttg aac      144
Thr Asn Asp Thr Pro Val Ile Ile Asp Thr Thr Ala Pro Val Leu Asn
        35                  40                  45

aat gtg aaa tat gat aca tct tct ttc aca ttg tca ggt gat tac gct      192
Asn Val Lys Tyr Asp Thr Ser Ser Phe Thr Leu Ser Gly Asp Tyr Ala
    50                  55                  60

gat gca ggt gca ggc ttt act gac tac tca tat gca act gta act gtt      240
Asp Ala Gly Ala Gly Phe Thr Asp Tyr Ser Tyr Ala Thr Val Thr Val
65                  70                  75                  80

aac gat cat gtc ttt ggc ttt aag tta aac gaa ggc gat aag tca aac      288
Asn Asp His Val Phe Gly Phe Lys Leu Asn Glu Gly Asp Lys Ser Asn
                85                  90                  95

ttt gat aat gct aat aaa acc aag gga cac ttt gtc ttt gtt ttg act      336
Phe Asp Asn Ala Asn Lys Thr Lys Gly His Phe Val Phe Val Leu Thr
            100                 105                 110

ccg gaa gaa caa gct gct tta act agc gct gct aac aag gtt acc gtt      384
Pro Glu Glu Gln Ala Ala Leu Thr Ser Ala Ala Asn Lys Val Thr Val
        115                 120                 125

gcc ttt agt gat gtc gca gat aac act gca acg caa aca ttt aat gtt      432
Ala Phe Ser Asp Val Ala Asp Asn Thr Ala Thr Gln Thr Phe Asn Val
    130                 135                 140

gca cct gta gca ggt cat aaa aag att gca gtt tgg aat gca att aat      480
```

-continued

```
Ala Pro Val Ala Gly His Lys Lys Ile Ala Val Trp Asn Ala Ile Asn
145                 150                 155                 160

ggg tta cca ttc aat gaa aat tcc gat gat tat aat gtt ggt cgc aaa      528
Gly Leu Pro Phe Asn Glu Asn Ser Asp Asp Tyr Asn Val Gly Arg Lys
                165                 170                 175

gta ttt atg ctt cgt ggt ggt gct gaa cat gat ttc tat gtc aat ggt      576
Val Phe Met Leu Arg Gly Gly Ala Glu His Asp Phe Tyr Val Asn Gly
            180                 185                 190

aag tgg gtt cag gtt gat caa ggt caa ttt gta ttg cca gtt agt gtt      624
Lys Trp Val Gln Val Asp Gln Gly Gln Phe Val Leu Pro Val Ser Val
        195                 200                 205

gat gaa cag aat ttt gtt ttc agt tca gat caa gcg ggt aaa aat att      672
Asp Glu Gln Asn Phe Val Phe Ser Ser Asp Gln Ala Gly Lys Asn Ile
    210                 215                 220

tta ggt aag ttc act act ttt act cct aaa gct caa ttc gca tgg caa      720
Leu Gly Lys Phe Thr Thr Phe Thr Pro Lys Ala Gln Phe Ala Trp Gln
225                 230                 235                 240

cat gtt gat ggt gaa gaa aga tca ttt ggt gtc agt gtt tac tca gta      768
His Val Asp Gly Glu Glu Arg Ser Phe Gly Val Ser Val Tyr Ser Val
                245                 250                 255

gaa ggc aag gat cca caa gat att gtt gtt caa gca tca gta ccc aag      816
Glu Gly Lys Asp Pro Gln Asp Ile Val Val Gln Ala Ser Val Pro Lys
            260                 265                 270

ggt gac aat gtt aaa gct ttt gcg aag gac tac ttc act cat gaa gtt      864
Gly Asp Asn Val Lys Ala Phe Ala Lys Asp Tyr Phe Thr His Glu Val
        275                 280                 285

tat acc ggt gag gtt cat gac ggt gta gct act ttc cac att cat acc      912
Tyr Thr Gly Glu Val His Asp Gly Val Ala Thr Phe His Ile His Thr
    290                 295                 300

agt gtc aat aaa gac gct gca act ggc att aat tta aga gcc ctt ctt      960
Ser Val Asn Lys Asp Ala Ala Thr Gly Ile Asn Leu Arg Ala Leu Leu
305                 310                 315                 320

caa ggt tgg gtt gaa att gat gga cca aca ttt aat gct aaa caa gta     1008
Gln Gly Trp Val Glu Ile Asp Gly Pro Thr Phe Asn Ala Lys Gln Val
                325                 330                 335

acg gat cca tcg cca att aat gat gct aac tac ttg ggt gtg tac tac     1056
Thr Asp Pro Ser Pro Ile Asn Asp Ala Asn Tyr Leu Gly Val Tyr Tyr
            340                 345                 350

aat cca aat gct gaa gag aga aag aat tat gat aat cgc gat gat ctt     1104
Asn Pro Asn Ala Glu Glu Arg Lys Asn Tyr Asp Asn Arg Asp Asp Leu
        355                 360                 365

ggc gta gac ttt gaa gat gaa gca gct gac aca aac aca ttt ggc cca     1152
Gly Val Asp Phe Glu Asp Glu Ala Ala Asp Thr Asn Thr Phe Gly Pro
    370                 375                 380

ggg aat tat tca agt gcg aaa gat gac gct aaa att cat ttc gac tac     1200
Gly Asn Tyr Ser Ser Ala Lys Asp Asp Ala Lys Ile His Phe Asp Tyr
385                 390                 395                 400

ttg aat aat aat ggt att tct act ttg ggt aat aaa gca gta gaa aag     1248
Leu Asn Asn Asn Gly Ile Ser Thr Leu Gly Asn Lys Ala Val Glu Lys
                405                 410                 415

ggt tat tac aat cca gca act cat aaa ttt act ttg act ggt cgg gtt     1296
Gly Tyr Tyr Asn Pro Ala Thr His Lys Phe Thr Leu Thr Gly Arg Val
            420                 425                 430

aat cca gaa gtt att agc tta aca ttc tta gct gat agt ccg tat gaa     1344
Asn Pro Glu Val Ile Ser Leu Thr Phe Leu Ala Asp Ser Pro Tyr Glu
        435                 440                 445

gtc gat cca gaa aat caa gct gat att cat gat aat ggt aaa ttc tct     1392
Val Asp Pro Glu Asn Gln Ala Asp Ile His Asp Asn Gly Lys Phe Ser
    450                 455                 460
```

-continued

```
gta aca ttc aca att gat aat cca gca aca cgt caa tta tca tat ttc      1440
Val Thr Phe Thr Ile Asp Asn Pro Ala Thr Arg Gln Leu Ser Tyr Phe
465                 470                 475                 480

ttt aag acg aat gat ggc aaa aca aca aga ggc tct ttg act tta att      1488
Phe Lys Thr Asn Asp Gly Lys Thr Thr Arg Gly Ser Leu Thr Leu Ile
                485                 490                 495

ctt gac act gtt gat cca act ctt act gta gat caa tta ggc gac aag      1536
Leu Asp Thr Val Asp Pro Thr Leu Thr Val Asp Gln Leu Gly Asp Lys
            500                 505                 510

gat gag gct gaa att act act aat aag cca acc ttt aag tta tcc ggt      1584
Asp Glu Ala Glu Ile Thr Thr Asn Lys Pro Thr Phe Lys Leu Ser Gly
        515                 520                 525

gag gcc aac gat aac att gat ggt tac aat gta ttt atc aat ggt gat      1632
Glu Ala Asn Asp Asn Ile Asp Gly Tyr Asn Val Phe Ile Asn Gly Asp
    530                 535                 540

aat gtt ttt ggg caa ttt ggt aat tcg ggt tat gat ttt ctg cca gga      1680
Asn Val Phe Gly Gln Phe Gly Asn Ser Gly Tyr Asp Phe Leu Pro Gly
545                 550                 555                 560

atc tac aat gat tta aat caa aat act cca aat ttg tac gga tct tac      1728
Ile Tyr Asn Asp Leu Asn Gln Asn Thr Pro Asn Leu Tyr Gly Ser Tyr
                565                 570                 575

aag ttt gat caa gaa gag caa ttg gat gat cag aat ggg caa cca aca      1776
Lys Phe Asp Gln Glu Glu Gln Leu Asp Asp Gln Asn Gly Gln Pro Thr
            580                 585                 590

acc cat gtc ttt act att gca gta gag gac caa gct ggt aac aga gtt      1824
Thr His Val Phe Thr Ile Ala Val Glu Asp Gln Ala Gly Asn Arg Val
        595                 600                 605

gaa aag aag gtt act gtt cat tac gat cca aat tat ctt aca gaa ccg      1872
Glu Lys Lys Val Thr Val His Tyr Asp Pro Asn Tyr Leu Thr Glu Pro
    610                 615                 620

ggt aat aca gga aaa aaa gat gat caa gca gat gta aaa ccg gca gaa      1920
Gly Asn Thr Gly Lys Lys Asp Asp Gln Ala Asp Val Lys Pro Ala Glu
625                 630                 635                 640

ggt caa aag caa gat aaa aat gac aac caa act gtt aac aat tca aaa      1968
Gly Gln Lys Gln Asp Lys Asn Asp Asn Gln Thr Val Asn Asn Ser Lys
                645                 650                 655

gaa gat cca gag agt ggt caa act act gaa aat gct caa tct aca gaa      2016
Glu Asp Pro Glu Ser Gly Gln Thr Thr Glu Asn Ala Gln Ser Thr Glu
            660                 665                 670

agt caa gag caa aat aag act gat gta act aaa cca gca gca aag cca      2064
Ser Gln Glu Gln Asn Lys Thr Asp Val Thr Lys Pro Ala Ala Lys Pro
        675                 680                 685

agt aac gat gat caa aaa gaa aat cac aga gct ggt gaa tcg acc att      2112
Ser Asn Asp Asp Gln Lys Glu Asn His Arg Ala Gly Glu Ser Thr Ile
    690                 695                 700

gag tta aat caa gag aaa caa cta ggt caa agt aat gtc caa gcc caa      2160
Glu Leu Asn Gln Glu Lys Gln Leu Gly Gln Ser Asn Val Gln Ala Gln
705                 710                 715                 720

gat act aaa cca gat aaa aca gta gtt caa ggt aat gtt caa aat act      2208
Asp Thr Lys Pro Asp Lys Thr Val Val Gln Gly Asn Val Gln Asn Thr
                725                 730                 735

gca ccg aca aca ggt cat ttg act aat tct tca gta aat gtg caa caa      2256
Ala Pro Thr Thr Gly His Leu Thr Asn Ser Ser Val Asn Val Gln Gln
            740                 745                 750

ttt aag act aag aaa gaa aca cta caa tta aag aag ttt aag tta tta      2304
Phe Lys Thr Lys Lys Glu Thr Leu Gln Leu Lys Lys Phe Lys Leu Leu
        755                 760                 765

aag aat aca tat ggc tac act tta aat ggt aaa att gct aaa aaa cac      2352
Lys Asn Thr Tyr Gly Tyr Thr Leu Asn Gly Lys Ile Ala Lys Lys His
    770                 775                 780
```

-continued

```
ggt aaa aag tta ctc ttt aag aaa gga aaa acc gtc ctt gtt tgg aac      2400
Gly Lys Lys Leu Leu Phe Lys Lys Gly Lys Thr Val Leu Val Trp Asn
785                 790                 795                 800

aac agt aga gtt gtg act atc aag gga caa aag tac tac cgt gct act      2448
Asn Ser Arg Val Val Thr Ile Lys Gly Gln Lys Tyr Tyr Arg Ala Thr
                805                 810                 815

aag aat gta ttt gtt aaa gtt tca act atc aag cag gtt aaa gac ttg      2496
Lys Asn Val Phe Val Lys Val Ser Thr Ile Lys Gln Val Lys Asp Leu
            820                 825                 830

aaa tta gtt tta acg aag aac tcc tac gtt tac aat aaa ttg ggc aaa      2544
Lys Leu Val Leu Thr Lys Asn Ser Tyr Val Tyr Asn Lys Leu Gly Lys
        835                 840                 845

cgc gtt aag tat aag agt caa agt ttg ctt aag gaa ggt aaa cat ctt      2592
Arg Val Lys Tyr Lys Ser Gln Ser Leu Leu Lys Glu Gly Lys His Leu
    850                 855                 860

tct acc cac aat aat gga aaa gtt gtg act att aaa aat ata cat ttt      2640
Ser Thr His Asn Asn Gly Lys Val Val Thr Ile Lys Asn Ile His Phe
865                 870                 875                 880

ttt aat ata tct ctt ttc tta aaa tat ttc caa caa cgt                  2679
Phe Asn Ile Ser Leu Phe Leu Lys Tyr Phe Gln Gln Arg
                885                 890
```

<210> SEQ ID NO 4
<211> LENGTH: 893
<212> TYPE: PRT
<213> ORGANISM: Lactobacillus helveticus

<400> SEQUENCE: 4

```
Met Ile Arg Leu Leu Gly Arg Trp Leu Cys Ser Arg Trp Ser Ile His
1               5                   10                  15

Leu Pro Leu Cys Cys Pro Leu Tyr Asn Asn Gly Glu Asn Lys Val Gln
            20                  25                  30

Thr Asn Asp Thr Pro Val Ile Ile Asp Thr Thr Ala Pro Val Leu Asn
        35                  40                  45

Asn Val Lys Tyr Asp Thr Ser Ser Phe Thr Leu Ser Gly Asp Tyr Ala
    50                  55                  60

Asp Ala Gly Ala Gly Phe Thr Asp Tyr Ser Tyr Ala Thr Val Thr Val
65                  70                  75                  80

Asn Asp His Val Phe Gly Phe Lys Leu Asn Glu Gly Asp Lys Ser Asn
                85                  90                  95

Phe Asp Asn Ala Asn Lys Thr Lys Gly His Phe Val Phe Val Leu Thr
            100                 105                 110

Pro Glu Glu Gln Ala Ala Leu Thr Ser Ala Ala Asn Lys Val Thr Val
        115                 120                 125

Ala Phe Ser Asp Val Ala Asp Asn Thr Ala Thr Gln Thr Phe Asn Val
    130                 135                 140

Ala Pro Val Ala Gly His Lys Lys Ile Ala Val Trp Asn Ala Ile Asn
145                 150                 155                 160

Gly Leu Pro Phe Asn Glu Asn Ser Asp Asp Tyr Asn Val Gly Arg Lys
                165                 170                 175

Val Phe Met Leu Arg Gly Gly Ala Glu His Asp Phe Tyr Val Asn Gly
            180                 185                 190

Lys Trp Val Gln Val Asp Gln Gly Gln Phe Val Leu Pro Val Ser Val
        195                 200                 205

Asp Glu Gln Asn Phe Val Phe Ser Ser Asp Gln Ala Gly Lys Asn Ile
    210                 215                 220
```

-continued

```
Leu Gly Lys Phe Thr Thr Phe Thr Pro Lys Ala Gln Phe Ala Trp Gln
225                 230                 235                 240

His Val Asp Gly Glu Glu Arg Ser Phe Gly Val Ser Val Tyr Ser Val
                245                 250                 255

Glu Gly Lys Asp Pro Gln Asp Ile Val Val Gln Ala Ser Val Pro Lys
            260                 265                 270

Gly Asp Asn Val Lys Ala Phe Ala Lys Asp Tyr Phe Thr His Glu Val
        275                 280                 285

Tyr Thr Gly Glu Val His Asp Gly Val Ala Thr Phe His Ile His Thr
    290                 295                 300

Ser Val Asn Lys Asp Ala Ala Thr Gly Ile Asn Leu Arg Ala Leu Leu
305                 310                 315                 320

Gln Gly Trp Val Glu Ile Asp Gly Pro Thr Phe Asn Ala Lys Gln Val
                325                 330                 335

Thr Asp Pro Ser Pro Ile Asn Asp Ala Asn Tyr Leu Gly Val Tyr Tyr
            340                 345                 350

Asn Pro Asn Ala Glu Glu Arg Lys Asn Tyr Asp Asn Arg Asp Asp Leu
        355                 360                 365

Gly Val Asp Phe Glu Asp Glu Ala Ala Asp Thr Asn Thr Phe Gly Pro
    370                 375                 380

Gly Asn Tyr Ser Ser Ala Lys Asp Asp Ala Lys Ile His Phe Asp Tyr
385                 390                 395                 400

Leu Asn Asn Asn Gly Ile Ser Thr Leu Gly Asn Lys Ala Val Glu Lys
                405                 410                 415

Gly Tyr Tyr Asn Pro Ala Thr His Lys Phe Thr Leu Thr Gly Arg Val
            420                 425                 430

Asn Pro Glu Val Ile Ser Leu Thr Phe Leu Ala Asp Ser Pro Tyr Glu
        435                 440                 445

Val Asp Pro Glu Asn Gln Ala Asp Ile His Asp Asn Gly Lys Phe Ser
    450                 455                 460

Val Thr Phe Thr Ile Asp Asn Pro Ala Thr Arg Gln Leu Ser Tyr Phe
465                 470                 475                 480

Phe Lys Thr Asn Asp Gly Lys Thr Thr Arg Gly Ser Leu Thr Leu Ile
                485                 490                 495

Leu Asp Thr Val Asp Pro Thr Leu Thr Val Asp Gln Leu Gly Asp Lys
            500                 505                 510

Asp Glu Ala Glu Ile Thr Thr Asn Lys Pro Thr Phe Lys Leu Ser Gly
        515                 520                 525

Glu Ala Asn Asp Asn Ile Asp Gly Tyr Asn Val Phe Ile Asn Gly Asp
    530                 535                 540

Asn Val Phe Gly Gln Phe Gly Asn Ser Gly Tyr Asp Phe Leu Pro Gly
545                 550                 555                 560

Ile Tyr Asn Asp Leu Asn Gln Asn Thr Pro Asn Leu Tyr Gly Ser Tyr
                565                 570                 575

Lys Phe Asp Gln Glu Glu Gln Leu Asp Asp Gln Asn Gly Gln Pro Thr
            580                 585                 590

Thr His Val Phe Thr Ile Ala Val Glu Asp Gln Ala Gly Asn Arg Val
        595                 600                 605

Glu Lys Lys Val Thr Val His Tyr Asp Pro Asn Tyr Leu Thr Glu Pro
    610                 615                 620

Gly Asn Thr Gly Lys Lys Asp Asp Gln Ala Asp Val Lys Pro Ala Glu
625                 630                 635                 640

Gly Gln Lys Gln Asp Lys Asn Asp Asn Gln Thr Val Asn Asn Ser Lys
```

-continued

```
                645                 650                 655

Glu Asp Pro Glu Ser Gly Gln Thr Thr Glu Asn Ala Gln Ser Thr Glu
            660                 665                 670

Ser Gln Glu Gln Asn Lys Thr Asp Val Thr Lys Pro Ala Ala Lys Pro
        675                 680                 685

Ser Asn Asp Asp Gln Lys Glu Asn His Arg Ala Gly Glu Ser Thr Ile
    690                 695                 700

Glu Leu Asn Gln Glu Lys Gln Leu Gly Gln Ser Asn Val Gln Ala Gln
705                 710                 715                 720

Asp Thr Lys Pro Asp Lys Thr Val Val Gln Gly Asn Val Gln Asn Thr
                725                 730                 735

Ala Pro Thr Thr Gly His Leu Thr Asn Ser Ser Val Asn Val Gln Gln
            740                 745                 750

Phe Lys Thr Lys Lys Glu Thr Leu Gln Leu Lys Lys Phe Lys Leu Leu
        755                 760                 765

Lys Asn Thr Tyr Gly Tyr Thr Leu Asn Gly Lys Ile Ala Lys Lys His
    770                 775                 780

Gly Lys Lys Leu Leu Phe Lys Lys Gly Lys Thr Val Leu Val Trp Asn
785                 790                 795                 800

Asn Ser Arg Val Val Thr Ile Lys Gly Gln Lys Tyr Tyr Arg Ala Thr
                805                 810                 815

Lys Asn Val Phe Val Lys Val Ser Thr Ile Lys Gln Val Lys Asp Leu
            820                 825                 830

Lys Leu Val Leu Thr Lys Asn Ser Tyr Val Tyr Asn Lys Leu Gly Lys
        835                 840                 845

Arg Val Lys Tyr Lys Ser Gln Ser Leu Leu Lys Glu Gly Lys His Leu
    850                 855                 860

Ser Thr His Asn Asn Gly Lys Val Val Thr Ile Lys Asn Ile His Phe
865                 870                 875                 880

Phe Asn Ile Ser Leu Phe Leu Lys Tyr Phe Gln Gln Arg
                885                 890


<210> SEQ ID NO 5
<211> LENGTH: 4881
<212> TYPE: DNA
<213> ORGANISM: Lactobacillus helveticus
<220> FEATURE:
<221> NAME/KEY: CDS
<222> LOCATION: (1)..(4881)
<223> OTHER INFORMATION:

<400> SEQUENCE: 5

atg cta ctg gta ttc cag aaa ttg cag tta tgg gtg gct gca gca att      48
Met Leu Leu Val Phe Gln Lys Leu Gln Leu Trp Val Ala Ala Ala Ile
1               5                   10                  15

att gct ctt gct tca ggc tcc act gtt ttt ctt agt caa aat act gct      96
Ile Ala Leu Ala Ser Gly Ser Thr Val Phe Leu Ser Gln Asn Thr Ala
            20                  25                  30

gaa gca gca act aat gat cct ggt gct tca gat gtt caa gtt aaa gta     144
Glu Ala Ala Thr Asn Asp Pro Gly Ala Ser Asp Val Gln Val Lys Val
        35                  40                  45

gta caa caa gat caa aaa caa gac caa aac agt act gct aac gca gct     192
Val Gln Gln Asp Gln Lys Gln Asp Gln Asn Ser Thr Ala Asn Ala Ala
    50                  55                  60

gtt tca aat tct gat tct gcc aag aca cag act aat gca acg gac cag     240
Val Ser Asn Ser Asp Ser Ala Lys Thr Gln Thr Asn Ala Thr Asp Gln
65                  70                  75                  80
```

-continued

```
aca caa aat tca act gtg gtt tct ggt gat tcc acg act gcg aat tct      288
Thr Gln Asn Ser Thr Val Val Ser Gly Asp Ser Thr Thr Ala Asn Ser
                85                  90                  95

aag acc tca cag act tct aat gca caa act aca agt aca aca aca aat      336
Lys Thr Ser Gln Thr Ser Asn Ala Gln Thr Thr Ser Thr Thr Thr Asn
            100                 105                 110

agt gta gat cca aac cag gaa caa caa cct gct aat caa gct gat cat      384
Ser Val Asp Pro Asn Gln Glu Gln Gln Pro Ala Asn Gln Ala Asp His
        115                 120                 125

gtt aaa gga aat gtg cag tct gca tgg gat caa gga tat agg gga caa      432
Val Lys Gly Asn Val Gln Ser Ala Trp Asp Gln Gly Tyr Arg Gly Gln
    130                 135                 140

gga aca gtt gtt gca gtc atc gat tcc ggt gca gat cca act cat aaa      480
Gly Thr Val Val Ala Val Ile Asp Ser Gly Ala Asp Pro Thr His Lys
145                 150                 155                 160

gat ttt aaa acc atg cca gaa gat cct aag ctg tcc gag gat gat atg      528
Asp Phe Lys Thr Met Pro Glu Asp Pro Lys Leu Ser Glu Asp Asp Met
                165                 170                 175

caa gct aag atc gcc aag caa ggc tat ggt aaa tat gtg aat gaa aag      576
Gln Ala Lys Ile Ala Lys Gln Gly Tyr Gly Lys Tyr Val Asn Glu Lys
            180                 185                 190

ttc cca tat gtt tat aat tat gcc gat cgt gat aat gac tat att act      624
Phe Pro Tyr Val Tyr Asn Tyr Ala Asp Arg Asp Asn Asp Tyr Ile Thr
        195                 200                 205

tcg gat gac acc aat gct aat gat tct cca cac ggt caa cac gtt tca      672
Ser Asp Asp Thr Asn Ala Asn Asp Ser Pro His Gly Gln His Val Ser
    210                 215                 220

gga atc att gca gct gat ggt aag cca gat gga aat aaa gaa tat gtc      720
Gly Ile Ile Ala Ala Asp Gly Lys Pro Asp Gly Asn Lys Glu Tyr Val
225                 230                 235                 240

gtt ggt gtt gct cct gaa gct caa ttg atg cag ctg aga gtt ttt gga      768
Val Gly Val Ala Pro Glu Ala Gln Leu Met Gln Leu Arg Val Phe Gly
                245                 250                 255

caa ttt tca gat gaa aaa act gat gat gtg gca aaa gca atc tac gat      816
Gln Phe Ser Asp Glu Lys Thr Asp Asp Val Ala Lys Ala Ile Tyr Asp
            260                 265                 270

gct acc aat tta ggt gcg gat gtc atc caa atg tca tta gga caa ggt      864
Ala Thr Asn Leu Gly Ala Asp Val Ile Gln Met Ser Leu Gly Gln Gly
        275                 280                 285

gtt gcc gat caa caa ttg acc aat att gag caa aaa gct gtt caa tat      912
Val Ala Asp Gln Gln Leu Thr Asn Ile Glu Gln Lys Ala Val Gln Tyr
    290                 295                 300

gca att gat cac ggt gta ttt gta tca att tca gca tct aat aac ggt      960
Ala Ile Asp His Gly Val Phe Val Ser Ile Ser Ala Ser Asn Asn Gly
305                 310                 315                 320

aat tca gct tca gtt gat aat cca agt aaa gtt aaa gat caa gga tat     1008
Asn Ser Ala Ser Val Asp Asn Pro Ser Lys Val Lys Asp Gln Gly Tyr
                325                 330                 335

caa tct ggt agc caa gct ggt aac tat gaa cct ctt aat tta agt act     1056
Gln Ser Gly Ser Gln Ala Gly Asn Tyr Glu Pro Leu Asn Leu Ser Thr
            340                 345                 350

gta gca aac cct ggt gtg tca aag aac gca tta act gtt gct gca gaa     1104
Val Ala Asn Pro Gly Val Ser Lys Asn Ala Leu Thr Val Ala Ala Glu
        355                 360                 365

aca tca gat act ggt gat tta agc gat atg gcc tac ttc tca tca tgg     1152
Thr Ser Asp Thr Gly Asp Leu Ser Asp Met Ala Tyr Phe Ser Ser Trp
    370                 375                 380

ggc cca gct caa gac tat act tta aag cca gat tta tca gca cct gga     1200
Gly Pro Ala Gln Asp Tyr Thr Leu Lys Pro Asp Leu Ser Ala Pro Gly
385                 390                 395                 400
```

-continued

```
tat caa gta gtt tct acc gtt aat cat gat cag tac caa aca atg agt      1248
Tyr Gln Val Val Ser Thr Val Asn His Asp Gln Tyr Gln Thr Met Ser
                405                 410                 415

ggt act tca atg gct ggt cca ttt gcc gca gct agt gct gcc tta gta      1296
Gly Thr Ser Met Ala Gly Pro Phe Ala Ala Ala Ser Ala Ala Leu Val
            420                 425                 430

att caa cga ttg aag caa act aat cct gaa ttg aag ggt gca caa tta      1344
Ile Gln Arg Leu Lys Gln Thr Asn Pro Glu Leu Lys Gly Ala Gln Leu
        435                 440                 445

gta gct gct gct aaa gca atg ctg atg aat acg gcc aaa cca caa aca      1392
Val Ala Ala Ala Lys Ala Met Leu Met Asn Thr Ala Lys Pro Gln Thr
    450                 455                 460

caa tta ggc tat aca aca cct gtt tca cca aga cgt caa ggt gca ggt      1440
Gln Leu Gly Tyr Thr Thr Pro Val Ser Pro Arg Arg Gln Gly Ala Gly
465                 470                 475                 480

caa att gat gtt ggt gct gct acg gct act cca gtt tat gta act act      1488
Gln Ile Asp Val Gly Ala Ala Thr Ala Thr Pro Val Tyr Val Thr Thr
                485                 490                 495

gat gac ggc act agt tca gta tca ctt cat caa gtt ggt gaa agt act      1536
Asp Asp Gly Thr Ser Ser Val Ser Leu His Gln Val Gly Glu Ser Thr
            500                 505                 510

aaa ttt acg tta acc ttc cat aat tta act gac caa agc cga act tat      1584
Lys Phe Thr Leu Thr Phe His Asn Leu Thr Asp Gln Ser Arg Thr Tyr
        515                 520                 525

act ttc gat gat tat ggt gga ggt tac act gaa caa aga gat aca acc      1632
Thr Phe Asp Asp Tyr Gly Gly Gly Tyr Thr Glu Gln Arg Asp Thr Thr
    530                 535                 540

acc ggc gtt ttt cat gat gtt caa tta gct ggt gct aga gta aat ggt      1680
Thr Gly Val Phe His Asp Val Gln Leu Ala Gly Ala Arg Val Asn Gly
545                 550                 555                 560

gaa cat agt ttt act tta gct cct aaa gaa gaa cgt caa gtt agc tat      1728
Glu His Ser Phe Thr Leu Ala Pro Lys Glu Glu Arg Gln Val Ser Tyr
                565                 570                 575

tca tta gac ttg acc ggc tta aag aag aac caa tta gtt gaa gga ttt      1776
Ser Leu Asp Leu Thr Gly Leu Lys Lys Asn Gln Leu Val Glu Gly Phe
            580                 585                 590

tta cgc ttt act aat gcc aat aat gca tct acg gtt tct gtt cct tac      1824
Leu Arg Phe Thr Asn Ala Asn Asn Ala Ser Thr Val Ser Val Pro Tyr
        595                 600                 605

tta gct tat tat ggg gac tta act agt gaa aac gtc ttt gat caa aat      1872
Leu Ala Tyr Tyr Gly Asp Leu Thr Ser Glu Asn Val Phe Asp Gln Asn
    610                 615                 620

gca aat gag gag cat cta gat atc cag ggt aat cgt tta gtt aat gaa      1920
Ala Asn Glu Glu His Leu Asp Ile Gln Gly Asn Arg Leu Val Asn Glu
625                 630                 635                 640

caa aac tat cct cgt ggt att gca gat caa gaa tca ttg aag gaa ctt      1968
Gln Asn Tyr Pro Arg Gly Ile Ala Asp Gln Glu Ser Leu Lys Glu Leu
                645                 650                 655

gta aat gtt gat gga aac tat aat tgg caa gaa gta gcc aaa tta tat      2016
Val Asn Val Asp Gly Asn Tyr Asn Trp Gln Glu Val Ala Lys Leu Tyr
            660                 665                 670

gaa agt ggt aaa gtt gcc ttt tca cca aat gat aat caa aag agc gat      2064
Glu Ser Gly Lys Val Ala Phe Ser Pro Asn Asp Asn Gln Lys Ser Asp
        675                 680                 685

tta ctg aag cca tat gtt tac ttg aag caa aat gtt aaa gat ctt aag      2112
Leu Leu Lys Pro Tyr Val Tyr Leu Lys Gln Asn Val Lys Asp Leu Lys
    690                 695                 700

gta gaa atc ctc gat gca caa ggt aac gtg gtt aga gtg gtt tct gac      2160
Val Glu Ile Leu Asp Ala Gln Gly Asn Val Val Arg Val Val Ser Asp
```

-continued

```
705                 710                 715                 720

gtt caa ggc gta gat aaa tct tac gat gaa aat ggt gta act aaa gat      2208
Val Gln Gly Val Asp Lys Ser Tyr Asp Glu Asn Gly Val Thr Lys Asp
            725                 730                 735

act agt tta tca gtt tca atg aga gat aat cct gac gct ctt gaa tgg      2256
Thr Ser Leu Ser Val Ser Met Arg Asp Asn Pro Asp Ala Leu Glu Trp
            740                 745                 750

gat ggt aaa gtt tat aac agc aaa aca ggc aaa atg gaa act gcc aaa      2304
Asp Gly Lys Val Tyr Asn Ser Lys Thr Gly Lys Met Glu Thr Ala Lys
        755                 760                 765

gat ggc aat tac act tac cgt tta gtt gct act ctt tgg aac aaa gga      2352
Asp Gly Asn Tyr Thr Tyr Arg Leu Val Ala Thr Leu Trp Asn Lys Gly
    770                 775                 780

cca cat caa gtt caa aca gct gat ttc cca gta gta gtt gat aca gtt      2400
Pro His Gln Val Gln Thr Ala Asp Phe Pro Val Val Val Asp Thr Val
785                 790                 795                 800

gct cca aca ttg tca aat gtg aaa tat gat gct gcc tca cat act ttg      2448
Ala Pro Thr Leu Ser Asn Val Lys Tyr Asp Ala Ala Ser His Thr Leu
                805                 810                 815

tca ggt gaa tac caa gat gct ggt gca gga ttt acg aat tat tca tat      2496
Ser Gly Glu Tyr Gln Asp Ala Gly Ala Gly Phe Thr Asn Tyr Ser Tyr
            820                 825                 830

gca acg gta aca gtt aat gat aag gtc ttt ggc tat aag ttg agt gat      2544
Ala Thr Val Thr Val Asn Asp Lys Val Phe Gly Tyr Lys Leu Ser Asp
        835                 840                 845

ggt gga tca ggc ttc gat aat gca gaa aag act aag gga cat ttt agc      2592
Gly Gly Ser Gly Phe Asp Asn Ala Glu Lys Thr Lys Gly His Phe Ser
    850                 855                 860

ttt gtg tta ggt caa gat gca ctt tct gca tta aca gct gct gca aac      2640
Phe Val Leu Gly Gln Asp Ala Leu Ser Ala Leu Thr Ala Ala Ala Asn
865                 870                 875                 880

aag gtg acc gta gcc ttg agt gat gtc gct gat aat act tca ttg gct      2688
Lys Val Thr Val Ala Leu Ser Asp Val Ala Asp Asn Thr Ser Leu Ala
                885                 890                 895

act gtt aat gtt gcc ggt gac cat gat agt gag act ggt gta agt gtt      2736
Thr Val Asn Val Ala Gly Asp His Asp Ser Glu Thr Gly Val Ser Val
            900                 905                 910

tgg aat gct gtc aat ggt tta gcc ttt gat caa aaa tca cca aac tat      2784
Trp Asn Ala Val Asn Gly Leu Ala Phe Asp Gln Lys Ser Pro Asn Tyr
        915                 920                 925

gat gca gct act aag act tac aca tta gtt ggt gga gct aac cat gac      2832
Asp Ala Ala Thr Lys Thr Tyr Thr Leu Val Gly Gly Ala Asn His Asp
    930                 935                 940

ttc tac tta aat ggc aag ttg gtc caa gta caa gat ggc aaa tat caa      2880
Phe Tyr Leu Asn Gly Lys Leu Val Gln Val Gln Asp Gly Lys Tyr Gln
945                 950                 955                 960

gtt cca gtc agt gta aat aca act aag ttt gtg ttt agt act gat cct      2928
Val Pro Val Ser Val Asn Thr Thr Lys Phe Val Phe Ser Thr Asp Pro
                965                 970                 975

gaa ggt caa cat gtt ctt aag gat ctt tca act gta acg gct aaa gca      2976
Glu Gly Gln His Val Leu Lys Asp Leu Ser Thr Val Thr Ala Lys Ala
            980                 985                 990

ttc ttt aat tgg caa aag act gat  aca ttt gat gga aac  ttt ggt gta    3024
Phe Phe Asn Trp Gln Lys Thr Asp  Thr Phe Asp Gly Asn  Phe Gly Val
        995                 1000                1005

act att  agt tca gtt aaa act  aat aat cca aat gat  aca gtt gtt       3069
Thr Ile  Ser Ser Val Lys Thr  Asn Asn Pro Asn Asp  Thr Val Val
    1010                1015                1020

caa gct  gtt gta acc aaa ggt  aaa aat gta aag gcc  tat gca atg      3114
```

-continued

```
Gln Ala Val Val Thr Lys Gly Lys Asn Val Lys Ala Tyr Ala Met
    1025                1030                1035

gat tac ttt act ggg gaa gtt tat acc ggt gaa gta aaa gac gga      3159
Asp Tyr Phe Thr Gly Glu Val Tyr Thr Gly Glu Val Lys Asp Gly
    1040                1045                1050

att gca aca ttc cat gtt cat act tca atc aat aaa gat gct aca      3204
Ile Ala Thr Phe His Val His Thr Ser Ile Asn Lys Asp Ala Thr
    1055                1060                1065

act ggt gtt tat agg aga gca tta cta aca ggt tgg act gaa gtg      3249
Thr Gly Val Tyr Arg Arg Ala Leu Leu Thr Gly Trp Thr Glu Val
    1070                1075                1080

gat gga cca tcc ttt aat gat aaa caa gaa aca tct aga gat ggt      3294
Asp Gly Pro Ser Phe Asn Asp Lys Gln Glu Thr Ser Arg Asp Gly
    1085                1090                1095

gta tca agt agt aac cac cta ggg gtt ttc tac ttt gct gat gca      3339
Val Ser Ser Ser Asn His Leu Gly Val Phe Tyr Phe Ala Asp Ala
    1100                1105                1110

gct aat cgc cca gtt tat aca gat aga aat gcc ttg gga gta gaa      3384
Ala Asn Arg Pro Val Tyr Thr Asp Arg Asn Ala Leu Gly Val Glu
    1115                1120                1125

gct aaa gat gaa gct gca aag tta gat tca ttt tgc cca ggt gca      3429
Ala Lys Asp Glu Ala Ala Lys Leu Asp Ser Phe Cys Pro Gly Ala
    1130                1135                1140

tac cca gga cac gca cca tca gct ctg aca acc aga acg gat cct      3474
Tyr Pro Gly His Ala Pro Ser Ala Leu Thr Thr Arg Thr Asp Pro
    1145                1150                1155

aat cca gat att cat ttt gat tat atg aat gac aac gat act act      3519
Asn Pro Asp Ile His Phe Asp Tyr Met Asn Asp Asn Asp Thr Thr
    1160                1165                1170

cgt ttt ggt cag aat gcc gtt act cat gga tac tat gat cct tca      3564
Arg Phe Gly Gln Asn Ala Val Thr His Gly Tyr Tyr Asp Pro Ser
    1175                1180                1185

act cag aag ttt acg gtt acc ggt aaa gtt gat gac aat gta gta      3609
Thr Gln Lys Phe Thr Val Thr Gly Lys Val Asp Asp Asn Val Val
    1190                1195                1200

tct cta act gtg tta ggc gat aac tca aat gaa aat gct cct gaa      3654
Ser Leu Thr Val Leu Gly Asp Asn Ser Asn Glu Asn Ala Pro Glu
    1205                1210                1215

aac caa gtt aag tta ggc aac gac ggt aag ttt agc ttt acg gta      3699
Asn Gln Val Lys Leu Gly Asn Asp Gly Lys Phe Ser Phe Thr Val
    1220                1225                1230

aca gct aac aga aca ggg caa cgt cca att gca tat att tac aaa      3744
Thr Ala Asn Arg Thr Gly Gln Arg Pro Ile Ala Tyr Ile Tyr Lys
    1235                1240                1245

gct aaa gat gga caa aga gtt cgt ggt acc ttg aat ctt att ctt      3789
Ala Lys Asp Gly Gln Arg Val Arg Gly Thr Leu Asn Leu Ile Leu
    1250                1255                1260

gat act gtt gct cct agc ttg gaa gta aat cag gtt aat ggg gat      3834
Asp Thr Val Ala Pro Ser Leu Glu Val Asn Gln Val Asn Gly Asp
    1265                1270                1275

gaa tta gag ctt tgg act aat aat cca aaa ttc act ctg tcc gga      3879
Glu Leu Glu Leu Trp Thr Asn Asn Pro Lys Phe Thr Leu Ser Gly
    1280                1285                1290

aag gta aat gat aat ctt gat gga tat agg tta ttc gtt aat ggt      3924
Lys Val Asn Asp Asn Leu Asp Gly Tyr Arg Leu Phe Val Asn Gly
    1295                1300                1305

aat aat att tat cga gaa ttc cta aac tct ggt tat aat cag gtt      3969
Asn Asn Ile Tyr Arg Glu Phe Leu Asn Ser Gly Tyr Asn Gln Val
    1310                1315                1320
```

-continued

```
gca gga  ttg aat acg gat act  gag ttt act aat cca  tat gga gct      4014
Ala Gly  Leu Asn Thr Asp Thr  Glu Phe Thr Asn Pro  Tyr Gly Ala
    1325                 1330                 1335

cat gat  ttt gaa gag gtt gaa  aac tta aat gac aat  aat gat caa      4059
His Asp  Phe Glu Glu Val Glu  Asn Leu Asn Asp Asn  Asn Asp Gln
    1340                 1345                 1350

ccg act  act cat gtc ttc aca  gtt tat gtt gta gac  caa gtt gga      4104
Pro Thr  Thr His Val Phe Thr  Val Tyr Val Val Asp  Gln Val Gly
    1355                 1360                 1365

aac aag  gta gaa aag aaa tta  act gtt cac ttt gat  cca aat tat      4149
Asn Lys  Val Glu Lys Lys Leu  Thr Val His Phe Asp  Pro Asn Tyr
    1370                 1375                 1380

gtt gct  cca gaa gaa gta cca  aat act gat act tca  tat act tta      4194
Val Ala  Pro Glu Glu Val Pro  Asn Thr Asp Thr Ser  Tyr Thr Leu
    1385                 1390                 1395

gag aat  cca tta agt act aca  act gta gaa aac cca  gtt act gat      4239
Glu Asn  Pro Leu Ser Thr Thr  Thr Val Glu Asn Pro  Val Thr Asp
    1400                 1405                 1410

gtt tct  acg gtt caa cct aag  ggt gaa act tta act  ggt aag tca      4284
Val Ser  Thr Val Gln Pro Lys  Gly Glu Thr Leu Thr  Gly Lys Ser
    1415                 1420                 1425

ttc aac  tta tta cac gat gct  tat atc tac aac aaa  gat ggt caa      4329
Phe Asn  Leu Leu His Asp Ala  Tyr Ile Tyr Asn Lys  Asp Gly Gln
    1430                 1435                 1440

gtc gtt  tta agt act gat act  aat aag agt agc ttg  ctt aag aaa      4374
Val Val  Leu Ser Thr Asp Thr  Asn Lys Ser Ser Leu  Leu Lys Lys
    1445                 1450                 1455

ggc caa  aga att act gca tta  gac aat ggc aaa act  gtt gta atc      4419
Gly Gln  Arg Ile Thr Ala Leu  Asp Asn Gly Lys Thr  Val Val Ile
    1460                 1465                 1470

aat ggc  gtg caa tac tat cgt  gtc ggc gat aat cag  ttt gtg aag      4464
Asn Gly  Val Gln Tyr Tyr Arg  Val Gly Asp Asn Gln  Phe Val Lys
    1475                 1480                 1485

gta act  aat acg att tta caa  gcc ggt aag aga ttg  cag tta aag      4509
Val Thr  Asn Thr Ile Leu Gln  Ala Gly Lys Arg Leu  Gln Leu Lys
    1490                 1495                 1500

cat aat  gca cac ctt tat gat  aag aac ggt aaa gtt  gtt aaa aga      4554
His Asn  Ala His Leu Tyr Asp  Lys Asn Gly Lys Val  Val Lys Arg
    1505                 1510                 1515

aat ggc  aaa cct gtc ttg tta  aga aag ggt aga tgg  atc agt gct      4599
Asn Gly  Lys Pro Val Leu Leu  Arg Lys Gly Arg Trp  Ile Ser Ala
    1520                 1525                 1530

ttg aac  aac gcc gat aag tat  gta atc aat ggc aag  acc ttc tac      4644
Leu Asn  Asn Ala Asp Lys Tyr  Val Ile Asn Gly Lys  Thr Phe Tyr
    1535                 1540                 1545

aag tta  gct aat ggt gaa ttt  gtg aag gtg gca aac  act aaa ctt      4689
Lys Leu  Ala Asn Gly Glu Phe  Val Lys Val Ala Asn  Thr Lys Leu
    1550                 1555                 1560

caa aag  cct aaa gct ttg aag  ctt aca cac aat gca  ttt gtt tac      4734
Gln Lys  Pro Lys Ala Leu Lys  Leu Thr His Asn Ala  Phe Val Tyr
    1565                 1570                 1575

gat gaa  aat ggt aag cgt gta  aag aag agt aaa gtt  tta aag aaa      4779
Asp Glu  Asn Gly Lys Arg Val  Lys Lys Ser Lys Val  Leu Lys Lys
    1580                 1585                 1590

ggc caa  acg att tta gca gaa  aat aat gca gaa aaa  ttc cat atc      4824
Gly Gln  Thr Ile Leu Ala Glu  Asn Asn Ala Glu Lys  Phe His Ile
    1595                 1600                 1605

aaa ggt  aag gct tac tat aaa  gtt aat ggt cat ttt  gta aaa gtt      4869
Lys Gly  Lys Ala Tyr Tyr Lys  Val Asn Gly His Phe  Val Lys Val
    1610                 1615                 1620
```

```
gca aat  act ttg                                                  4881
Ala Asn  Thr Leu
    1625


<210> SEQ ID NO 6
<211> LENGTH: 1627
<212> TYPE: PRT
<213> ORGANISM: Lactobacillus helveticus

<400> SEQUENCE: 6

Met Leu Leu Val Phe Gln Lys Leu Gln Leu Trp Val Ala Ala Ala Ile
1               5                   10                  15

Ile Ala Leu Ala Ser Gly Ser Thr Val Phe Leu Ser Gln Asn Thr Ala
            20                  25                  30

Glu Ala Ala Thr Asn Asp Pro Gly Ala Ser Asp Val Gln Val Lys Val
        35                  40                  45

Val Gln Gln Asp Gln Lys Gln Asp Gln Asn Ser Thr Ala Asn Ala Ala
    50                  55                  60

Val Ser Asn Ser Asp Ser Ala Lys Thr Gln Thr Asn Ala Thr Asp Gln
65                  70                  75                  80

Thr Gln Asn Ser Thr Val Val Ser Gly Asp Ser Thr Thr Ala Asn Ser
                85                  90                  95

Lys Thr Ser Gln Thr Ser Asn Ala Gln Thr Thr Ser Thr Thr Thr Asn
            100                 105                 110

Ser Val Asp Pro Asn Gln Glu Gln Gln Pro Ala Asn Gln Ala Asp His
        115                 120                 125

Val Lys Gly Asn Val Gln Ser Ala Trp Asp Gln Gly Tyr Arg Gly Gln
    130                 135                 140

Gly Thr Val Val Ala Val Ile Asp Ser Gly Ala Asp Pro Thr His Lys
145                 150                 155                 160

Asp Phe Lys Thr Met Pro Glu Asp Pro Lys Leu Ser Glu Asp Asp Met
                165                 170                 175

Gln Ala Lys Ile Ala Lys Gln Gly Tyr Gly Lys Tyr Val Asn Glu Lys
            180                 185                 190

Phe Pro Tyr Val Tyr Asn Tyr Ala Asp Arg Asp Asn Asp Tyr Ile Thr
        195                 200                 205

Ser Asp Asp Thr Asn Ala Asn Asp Ser Pro His Gly Gln His Val Ser
    210                 215                 220

Gly Ile Ile Ala Ala Asp Gly Lys Pro Asp Gly Asn Lys Glu Tyr Val
225                 230                 235                 240

Val Gly Val Ala Pro Glu Ala Gln Leu Met Gln Leu Arg Val Phe Gly
                245                 250                 255

Gln Phe Ser Asp Glu Lys Thr Asp Asp Val Ala Lys Ala Ile Tyr Asp
            260                 265                 270

Ala Thr Asn Leu Gly Ala Asp Val Ile Gln Met Ser Leu Gly Gln Gly
        275                 280                 285

Val Ala Asp Gln Gln Leu Thr Asn Ile Glu Gln Lys Ala Val Gln Tyr
    290                 295                 300

Ala Ile Asp His Gly Val Phe Val Ser Ile Ser Ala Ser Asn Asn Gly
305                 310                 315                 320

Asn Ser Ala Ser Val Asp Asn Pro Ser Lys Val Lys Asp Gln Gly Tyr
                325                 330                 335

Gln Ser Gly Ser Gln Ala Gly Asn Tyr Glu Pro Leu Asn Leu Ser Thr
            340                 345                 350
```

-continued

```
Val Ala Asn Pro Gly Val Ser Lys Asn Ala Leu Thr Val Ala Ala Glu
        355                 360                 365

Thr Ser Asp Thr Gly Asp Leu Ser Asp Met Ala Tyr Phe Ser Ser Trp
    370                 375                 380

Gly Pro Ala Gln Asp Tyr Thr Leu Lys Pro Asp Leu Ser Ala Pro Gly
385                 390                 395                 400

Tyr Gln Val Val Ser Thr Val Asn His Asp Gln Tyr Gln Thr Met Ser
                405                 410                 415

Gly Thr Ser Met Ala Gly Pro Phe Ala Ala Ala Ser Ala Ala Leu Val
            420                 425                 430

Ile Gln Arg Leu Lys Gln Thr Asn Pro Glu Leu Lys Gly Ala Gln Leu
        435                 440                 445

Val Ala Ala Ala Lys Ala Met Leu Met Asn Thr Ala Lys Pro Gln Thr
    450                 455                 460

Gln Leu Gly Tyr Thr Thr Pro Val Ser Pro Arg Arg Gln Gly Ala Gly
465                 470                 475                 480

Gln Ile Asp Val Gly Ala Ala Thr Ala Thr Pro Val Tyr Val Thr Thr
                485                 490                 495

Asp Asp Gly Thr Ser Ser Val Ser Leu His Gln Val Gly Glu Ser Thr
            500                 505                 510

Lys Phe Thr Leu Thr Phe His Asn Leu Thr Asp Gln Ser Arg Thr Tyr
        515                 520                 525

Thr Phe Asp Asp Tyr Gly Gly Gly Tyr Thr Glu Gln Arg Asp Thr Thr
    530                 535                 540

Thr Gly Val Phe His Asp Val Gln Leu Ala Gly Ala Arg Val Asn Gly
545                 550                 555                 560

Glu His Ser Phe Thr Leu Ala Pro Lys Glu Glu Arg Gln Val Ser Tyr
                565                 570                 575

Ser Leu Asp Leu Thr Gly Leu Lys Lys Asn Gln Leu Val Glu Gly Phe
            580                 585                 590

Leu Arg Phe Thr Asn Ala Asn Asn Ala Ser Thr Val Ser Val Pro Tyr
        595                 600                 605

Leu Ala Tyr Tyr Gly Asp Leu Thr Ser Glu Asn Val Phe Asp Gln Asn
    610                 615                 620

Ala Asn Glu Glu His Leu Asp Ile Gln Gly Asn Arg Leu Val Asn Glu
625                 630                 635                 640

Gln Asn Tyr Pro Arg Gly Ile Ala Asp Gln Glu Ser Leu Lys Glu Leu
                645                 650                 655

Val Asn Val Asp Gly Asn Tyr Asn Trp Gln Glu Val Ala Lys Leu Tyr
            660                 665                 670

Glu Ser Gly Lys Val Ala Phe Ser Pro Asn Asp Asn Gln Lys Ser Asp
        675                 680                 685

Leu Leu Lys Pro Tyr Val Tyr Leu Lys Gln Asn Val Lys Asp Leu Lys
    690                 695                 700

Val Glu Ile Leu Asp Ala Gln Gly Asn Val Val Arg Val Val Ser Asp
705                 710                 715                 720

Val Gln Gly Val Asp Lys Ser Tyr Asp Glu Asn Gly Val Thr Lys Asp
                725                 730                 735

Thr Ser Leu Ser Val Ser Met Arg Asp Asn Pro Asp Ala Leu Glu Trp
            740                 745                 750

Asp Gly Lys Val Tyr Asn Ser Lys Thr Gly Lys Met Glu Thr Ala Lys
        755                 760                 765

Asp Gly Asn Tyr Thr Tyr Arg Leu Val Ala Thr Leu Trp Asn Lys Gly
```

-continued

```
    770                 775                 780

Pro His Gln Val Gln Thr Ala Asp Phe Pro Val Val Val Asp Thr Val
785                 790                 795                 800

Ala Pro Thr Leu Ser Asn Val Lys Tyr Asp Ala Ala Ser His Thr Leu
                805                 810                 815

Ser Gly Glu Tyr Gln Asp Ala Gly Ala Gly Phe Thr Asn Tyr Ser Tyr
            820                 825                 830

Ala Thr Val Thr Val Asn Asp Lys Val Phe Gly Tyr Lys Leu Ser Asp
        835                 840                 845

Gly Gly Ser Gly Phe Asp Asn Ala Glu Lys Thr Lys Gly His Phe Ser
    850                 855                 860

Phe Val Leu Gly Gln Asp Ala Leu Ser Ala Leu Thr Ala Ala Ala Asn
865                 870                 875                 880

Lys Val Thr Val Ala Leu Ser Asp Val Ala Asp Asn Thr Ser Leu Ala
                885                 890                 895

Thr Val Asn Val Ala Gly Asp His Asp Ser Glu Thr Gly Val Ser Val
            900                 905                 910

Trp Asn Ala Val Asn Gly Leu Ala Phe Asp Gln Lys Ser Pro Asn Tyr
        915                 920                 925

Asp Ala Ala Thr Lys Thr Tyr Thr Leu Val Gly Gly Ala Asn His Asp
    930                 935                 940

Phe Tyr Leu Asn Gly Lys Leu Val Gln Val Gln Asp Gly Lys Tyr Gln
945                 950                 955                 960

Val Pro Val Ser Val Asn Thr Thr Lys Phe Val Phe Ser Thr Asp Pro
                965                 970                 975

Glu Gly Gln His Val Leu Lys Asp Leu Ser Thr Val Thr Ala Lys Ala
            980                 985                 990

Phe Phe Asn Trp Gln Lys Thr Asp  Thr Phe Asp Gly Asn  Phe Gly Val
        995                 1000                1005

Thr Ile  Ser Ser Val Lys Thr  Asn Asn Pro Asn Asp  Thr Val Val
    1010                1015                1020

Gln Ala  Val Val Thr Lys Gly  Lys Asn Val Lys Ala  Tyr Ala Met
    1025                1030                1035

Asp Tyr  Phe Thr Gly Glu Val  Tyr Thr Gly Glu Val  Lys Asp Gly
    1040                1045                1050

Ile Ala  Thr Phe His Val His  Thr Ser Ile Asn Lys  Asp Ala Thr
    1055                1060                1065

Thr Gly  Val Tyr Arg Arg Ala  Leu Leu Thr Gly Trp  Thr Glu Val
    1070                1075                1080

Asp Gly  Pro Ser Phe Asn Asp  Lys Gln Glu Thr Ser  Arg Asp Gly
    1085                1090                1095

Val Ser  Ser Ser Asn His Leu  Gly Val Phe Tyr Phe  Ala Asp Ala
    1100                1105                1110

Ala Asn  Arg Pro Val Tyr Thr  Asp Arg Asn Ala Leu  Gly Val Glu
    1115                1120                1125

Ala Lys  Asp Glu Ala Ala Lys  Leu Asp Ser Phe Cys  Pro Gly Ala
    1130                1135                1140

Tyr Pro  Gly His Ala Pro Ser  Ala Leu Thr Thr Arg  Thr Asp Pro
    1145                1150                1155

Asn Pro  Asp Ile His Phe Asp  Tyr Met Asn Asp Asn  Asp Thr Thr
    1160                1165                1170

Arg Phe  Gly Gln Asn Ala Val  Thr His Gly Tyr Tyr  Asp Pro Ser
    1175                1180                1185
```

-continued

```
Thr Gln  Lys Phe Thr Val Thr  Gly Lys Val Asp Asp  Asn Val Val
    1190                 1195                 1200

Ser Leu  Thr Val Leu Gly Asp  Asn Ser Asn Glu Asn  Ala Pro Glu
    1205                 1210                 1215

Asn Gln  Val Lys Leu Gly Asn  Asp Gly Lys Phe Ser  Phe Thr Val
    1220                 1225                 1230

Thr Ala  Asn Arg Thr Gly Gln  Arg Pro Ile Ala Tyr  Ile Tyr Lys
    1235                 1240                 1245

Ala Lys  Asp Gly Gln Arg Val  Arg Gly Thr Leu Asn  Leu Ile Leu
    1250                 1255                 1260

Asp Thr  Val Ala Pro Ser Leu  Glu Val Asn Gln Val  Asn Gly Asp
    1265                 1270                 1275

Glu Leu  Glu Leu Trp Thr Asn  Asn Pro Lys Phe Thr  Leu Ser Gly
    1280                 1285                 1290

Lys Val  Asn Asp Asn Leu Asp  Gly Tyr Arg Leu Phe  Val Asn Gly
    1295                 1300                 1305

Asn Asn  Ile Tyr Arg Glu Phe  Leu Asn Ser Gly Tyr  Asn Gln Val
    1310                 1315                 1320

Ala Gly  Leu Asn Thr Asp Thr  Glu Phe Thr Asn Pro  Tyr Gly Ala
    1325                 1330                 1335

His Asp  Phe Glu Glu Val Glu  Asn Leu Asn Asp Asn  Asn Asp Gln
    1340                 1345                 1350

Pro Thr  Thr His Val Phe Thr  Val Tyr Val Val Asp  Gln Val Gly
    1355                 1360                 1365

Asn Lys  Val Glu Lys Lys Leu  Thr Val His Phe Asp  Pro Asn Tyr
    1370                 1375                 1380

Val Ala  Pro Glu Glu Val Pro  Asn Thr Asp Thr Ser  Tyr Thr Leu
    1385                 1390                 1395

Glu Asn  Pro Leu Ser Thr Thr  Thr Val Glu Asn Pro  Val Thr Asp
    1400                 1405                 1410

Val Ser  Thr Val Gln Pro Lys  Gly Glu Thr Leu Thr  Gly Lys Ser
    1415                 1420                 1425

Phe Asn  Leu Leu His Asp Ala  Tyr Ile Tyr Asn Lys  Asp Gly Gln
    1430                 1435                 1440

Val Val  Leu Ser Thr Asp Thr  Asn Lys Ser Ser Leu  Leu Lys Lys
    1445                 1450                 1455

Gly Gln  Arg Ile Thr Ala Leu  Asp Asn Gly Lys Thr  Val Val Ile
    1460                 1465                 1470

Asn Gly  Val Gln Tyr Tyr Arg  Val Gly Asp Asn Gln  Phe Val Lys
    1475                 1480                 1485

Val Thr  Asn Thr Ile Leu Gln  Ala Gly Lys Arg Leu  Gln Leu Lys
    1490                 1495                 1500

His Asn  Ala His Leu Tyr Asp  Lys Asn Gly Lys Val  Val Lys Arg
    1505                 1510                 1515

Asn Gly  Lys Pro Val Leu Leu  Arg Lys Gly Arg Trp  Ile Ser Ala
    1520                 1525                 1530

Leu Asn  Asn Ala Asp Lys Tyr  Val Ile Asn Gly Lys  Thr Phe Tyr
    1535                 1540                 1545

Lys Leu  Ala Asn Gly Glu Phe  Val Lys Val Ala Asn  Thr Lys Leu
    1550                 1555                 1560

Gln Lys  Pro Lys Ala Leu Lys  Leu Thr His Asn Ala  Phe Val Tyr
    1565                 1570                 1575
```

-continued

```
Asp Glu  Asn Gly Lys Arg Val  Lys Lys Ser Lys Val  Leu Lys Lys
    1580                 1585                 1590

Gly Gln  Thr Ile Leu Ala Glu  Asn Asn Ala Glu Lys  Phe His Ile
    1595                 1600                 1605

Lys Gly  Lys Ala Tyr Tyr Lys  Val Asn Gly His Phe  Val Lys Val
    1610                 1615                 1620

Ala Asn  Thr Leu
    1625


<210> SEQ ID NO 7
<211> LENGTH: 20
<212> TYPE: DNA
<213> ORGANISM: Artificial
<220> FEATURE:
<223> OTHER INFORMATION: Primer sequence

<400> SEQUENCE: 7

cgatgataat cctagcgagc                                                20


<210> SEQ ID NO 8
<211> LENGTH: 18
<212> TYPE: DNA
<213> ORGANISM: Artificial Sequence
<220> FEATURE:
<223> OTHER INFORMATION: Primer sequence

<400> SEQUENCE: 8

tggcagaacc tgtgccta                                                  18


<210> SEQ ID NO 9
<211> LENGTH: 18
<212> TYPE: DNA
<213> ORGANISM: Artificial Sequence
<220> FEATURE:
<223> OTHER INFORMATION: Primer sequence

<400> SEQUENCE: 9

gccaagacgc ctctggta                                                  18


<210> SEQ ID NO 10
<211> LENGTH: 21
<212> TYPE: DNA
<213> ORGANISM: Artificial Sequence
<220> FEATURE:
<223> OTHER INFORMATION: Primer sequence

<400> SEQUENCE: 10

taggtatagt ttccatcagg a                                              21


<210> SEQ ID NO 11
<211> LENGTH: 23
<212> TYPE: DNA
<213> ORGANISM: Artificial Sequence
<220> FEATURE:
<223> OTHER INFORMATION: Primer sequence

<400> SEQUENCE: 11

aargtwccwt ayggyywyaa yta                                            23


<210> SEQ ID NO 12
<211> LENGTH: 23
<212> TYPE: DNA
<213> ORGANISM: Artificial Sequence
<220> FEATURE:
<223> OTHER INFORMATION: Primer sequence
```

<400> SEQUENCE: 12
gccatdswdg trccdswcat dtk 23

<210> SEQ ID NO 13
<211> LENGTH: 30
<212> TYPE: DNA
<213> ORGANISM: Artificial Sequence
<220> FEATURE:
<223> OTHER INFORMATION: Primer sequence

<400> SEQUENCE: 13
cgaaggcgat aagtcaaact ttgataatgc 30

<210> SEQ ID NO 14
<211> LENGTH: 27
<212> TYPE: DNA
<213> ORGANISM: Artificial Sequence
<220> FEATURE:
<223> OTHER INFORMATION: Primer sequence

<400> SEQUENCE: 14
cccggttctg taagataatt tggatcg 27

<210> SEQ ID NO 15
<211> LENGTH: 20
<212> TYPE: DNA
<213> ORGANISM: Artificial Sequence
<220> FEATURE:
<223> OTHER INFORMATION: Primer sequence

<400> SEQUENCE: 15
astcwrrytt ygatratgcw 20

<210> SEQ ID NO 16
<211> LENGTH: 20
<212> TYPE: DNA
<213> ORGANISM: Artificial Sequence
<220> FEATURE:
<223> OTHER INFORMATION: Primer sequence

<400> SEQUENCE: 16
bhkyamsawa rtttggatcr 20

<210> SEQ ID NO 17
<211> LENGTH: 17
<212> TYPE: DNA
<213> ORGANISM: Artificial Sequence
<220> FEATURE:
<223> OTHER INFORMATION: Primer sequence

<400> SEQUENCE: 17
ggtgttgctc ctgaagc 17

<210> SEQ ID NO 18
<211> LENGTH: 29
<212> TYPE: DNA
<213> ORGANISM: Artificial Sequence
<220> FEATURE:
<223> OTHER INFORMATION: Primer sequence

<400> SEQUENCE: 18
actctagcac cagctaattg aacatcatg 29